United States Patent
Jessen et al.

(10) Patent No.: US 8,030,045 B2
(45) Date of Patent: Oct. 4, 2011

(54) BETA-ALANINE/ALPHA-KETOGLUTARATE AMINOTRANSFERASE FOR 3-HYDROXYPROPIONIC ACID PRODUCTION

(75) Inventors: Holly Jean Jessen, Chanhassen, MN (US); Hans H. Liao, Eden Prairie, MN (US); Steven John Gort, Apple Valley, MN (US); Olga V. Selifonova, Plymouth, MN (US)

(73) Assignee: Cargill, Incorporated, Wayzata, MN (US)

( * ) Notice: Subject to any disclaimer, the term of this patent is extended or adjusted under 35 U.S.C. 154(b) by 159 days.

(21) Appl. No.: 12/310,503

(22) PCT Filed: Aug. 17, 2007

(86) PCT No.: PCT/US2007/076252
§ 371 (c)(1),
(2), (4) Date: Feb. 26, 2009

(87) PCT Pub. No.: WO2008/027742
PCT Pub. Date: Mar. 6, 2008

(65) Prior Publication Data
US 2009/0291480 A1 Nov. 26, 2009

Related U.S. Application Data

(60) Provisional application No. 60/824,031, filed on Aug. 30, 2006.

(51) Int. Cl.
| | |
|---|---|
| *C12N 9/10* | (2006.01) |
| *C12N 9/00* | (2006.01) |
| *C12N 1/20* | (2006.01) |
| *C12N 1/00* | (2006.01) |
| *C12N 15/00* | (2006.01) |
| *C12P 7/62* | (2006.01) |
| *C12P 7/52* | (2006.01) |
| *C12P 21/06* | (2006.01) |
| *C12P 19/34* | (2006.01) |
| *C07H 21/04* | (2006.01) |

(52) U.S. Cl. ........ 435/193; 435/183; 435/135; 435/141; 435/252.3; 435/254.11; 435/254.2; 435/320.1; 435/69.1; 435/91.1; 536/23.2; 536/23.1

(58) Field of Classification Search .................. 435/193, 435/183, 135, 141, 252.3, 254.11, 254.2, 435/320.1, 69.1, 91.1; 536/23.2, 23.1
See application file for complete search history.

(56) References Cited

U.S. PATENT DOCUMENTS
7,630,836 B2 * 12/2009 Omura et al. ................... 702/19

FOREIGN PATENT DOCUMENTS
WO WO 2005/118719 A2 12/2005
WO WO2006069610 * 7/2006

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Bentley et al., "Complete Genome Sequence of the Model Actinomycete *Streptomyces coelicolor* A3(2)" *Nature 417*:141-147, 2002.
Database UniProt [Online] Accession No. Q82ER2, "Putative Aminotransferase," Jun. 1, 2003 and Database EMBL [Online] Accession No. BA000030, "*Streptomyces avermitilis* MA-4680 Genomic DNA, Complete Genome," Oct. 31, 2004.
Database UniProt [Online] Accession No. Q9XAI0, "Putative Aminotransferase," Nov. 1, 1999, and Database EMBL [Online] Accession No. AL939117, "*Streptomyces coelicolor* A3(2) Complete Genome; Segment 14/29," Oct. 25, 2002.
Database UniProt [Online] Accession No. Q05881, "4-Aminobutyrate Transaminase (EC 2.6.1.19)," Sep. 5, 2006 and Database EMBL [Online] Accession No. CP000431, "*Rhodococcus* sp. RHA1, Complete Genome," Aug. 7, 2006.
Ikeda et al., "Complete Genome Sequence and Comparative Analysis of the Industrial Microorganism *Streptomyces avermitilis*," *Nature Biotechnol. 21*:526-531, 2003.
McLeod et al., "The Complete Genome of *Rhodococcus* sp. RHA1 Provides Insights into a Catabolic Powerhouse," *Proc. Natl. Acad. Sci. USA 103*:15582-15587, 2006.
Yonaha et al., "Distribution of Omega Amino-Acid Pyruvate Transaminase EC-2.6.1.18 and Amino Butyrate Alpha Keto Glutarate Transaminase EC-2.6.1.19 in Microorganisms," *Agricult. Biol. Chem. 47*:2257-2266, 1983.

* cited by examiner

Primary Examiner — Ganapathirama Raghu

(57) ABSTRACT

The present disclosure provides novel beta-alanine/alpha ketoglutarate aminotransferase nucleic acid and protein sequences having increased biological activity. Also provided are cells containing such enzymes, as well as methods of their use, for example to produce malonyl semialdehyde and downstream products thereof, such as 3-hydroxypropionic acid and derivatives thereof.

55 Claims, 3 Drawing Sheets

FIG. 2A

```
WT BAAT     1  mtpqpnpqvgaavkaadrahvfhswsaqelidplavagaegsyfwdydgr
BAAT1       1  mtpqpnpqvgaavkaadrahvfhtwsaqelidplavagaegsyfwdydgr
BAAT2       1  mtpqpnpqvgaavkaadrahvfhtwsaqelidplavagaegsyfwdydgr
BAAT3       1  mtpqpnpqvgaavkaadrahvfhtwsaqelidplavagaegsyfwdydgr
BAATP3H     1  mthqpnpqvgaavkaadrahvfhswsaqelidplavagaegsyfwdydgr
BAAT3ML     1  mthqpnpqvgaavkaadrahvfhtwsaqelidplavagaegsyfwdydgr
BAAT5-9     1  mthqpnpqvgaavkaadrahvfhtwsaqelidplavagaegsyfwdydgr WT BAAT    51  ryldftsglvftnigyqhpkvvaaiqeqaaslttfapafavearseaarl
BAAT1      51  ryldftsglvftnigyqhpkvvaaiqeqaaslttfapafavearseaarl
BAAT2      51  ryldftsglvftnigyqhpkvvaaiqeqaaslttfapafavearseaarl
BAAT3      51  ryldftsglvftnigyqhpkvvaaiqeqaaslttfapafavearseaarl
BAATP3H    51  ryldftsglvftnigyqhpkvvaaiqeqaaslttfapafavearseaarl
BAAT3ML    51  ryldftsglvftnigyqhpkvvaaiqeqaaslttfapafavearseaarl
BAAT5-9    51  ryldftsglvftnigyqhpkvvaaiqeqaaslttfapafavearseaarl WT BAAT   101  iaertpgdldkifftnggadaiehavrmarihagrpkvlsayrsyhggtq
BAAT1     101  iaertpgdldkifftnggadaiehavrmarihagrpkvlsayrsyhggtq
BAAT2     101  iaertpgdldkilftnggadaiehavrmarihagrpkvlsayrsyhggtq
BAAT3     101  iaertpgdldkilftnggadaiehavrmarihtgrpkvlsayrsyhggtq
BAATP3H   101  iaertpgdldkifftnggadaiehavrmarihagrpkvlsayrsyhggtq
BAAT3ML   101  iaertpgdldkilftnggadaiehavrmarihtgrpkvlsayrsyhggtq
BAAT5-9   101  iaertpgdlnkilftnggadaiehavrmarihtgrpkvlsayrsyhggtq WT BAAT   151  qavnitgdprrwasdsasagvvhfwapylyrsrfyaeteqqeceralehl
BAAT1     151  qavnitgdprrwasdsasagvvhfwapylyrsrfyaeteqqeceralehl
BAAT2     151  qavnitgdprrwasdsasagvvhfwapylyrsrfyaeteqqeceralehl
BAAT3     151  qavnitgdprrwasdsasagvvhfwapylyrsrfyaeteqqeceralehl
BAATP3H   151  qavnitgdprrwasdsasagvvhfwapylyrsrfyaeteqqeceralehl
BAAT3ML   151  qavnitgdprrwasdsasagvvhfwapylyrsrfyaeteqqeceralehl
BAAT5-9   151  qavnitgdprrwasdsasagvvhfwapylyrsrfyaeteqqeceralehl WT BAAT   201  ettiafegpgtiaaivletvpgtagimvpppgylagvrelcdkygivfvl
BAAT1     201  ettiafegpgtiaaivletvpgtagimvpppgylagvrelcdkygivfvl
BAAT2     201  ettiafegpgtiaaivletvpgtagimvpppgylagvrelcdkygivfvl
BAAT3     201  ettiafegpgtiaaivletvpgtagimvpppgylagvrelcdkygivfvl
BAATP3H   201  ettiafegpgtiaaivletvpgtagimvpppgylagvrelcdkygivfvl
BAAT3ML   201  ettiafegpgtiaaivletvpgtagimvpppgylagvrelcdkygivfvl
BAAT5-9   201  ettiafegpgtiaaivletvpgtagimvpppgylagvrelcdkygivfvl WT BAAT   251  devmagfgrtgewfaadlfdvtpdlmtfakgvnsgyvplggvaisgkiae
BAAT1     251  devmagfgrtgewfaadlfdvtpdlmtfakgvnsgyvplggvaisgkiae
BAAT2     251  devmagfgrtgewfaadlfdvtpdlmtfakgvnsgyvplggvaisgkiae
BAAT3     251  devmagfgrtgewfaadlfdvtpdlmtfakgvnsgyvplggvaisgkiae
BAATP3H   251  devmagfgrtgewfaadlfdvtpdlmtfakgvnsgyvplggvaisgkiae
BAAT3ML   251  devmagfgrtgewfaadlfdvtpdlmtfakgvnsgyvplggvaisgkiae
BAAT5-9   251  devmagfgrtgewfaadlfdvtpdlmtfakgvnsgyvplggvaisgkiae
```

FIG. 2B

| | | |
|---|---|---|
| WT BAAT | 301 | tfgkraypggltysghplacaaavatinvmaeegvvenaanlgarviepg |
| BAAT1 | 301 | tfgkraypggltysghplacaaavatinvmaeegvvenaanlgarviepg |
| BAAT2 | 301 | tfgkraypggltysghplacaaavatinvmaeegvvenaanlgarviepg |
| BAAT3 | 301 | tfgkraypggltysghplacaaavatinvmaeegvvenaanlgarviepg |
| BAATP3H | 301 | tfgkraypggltysghplacaaavatinvmaeegvvenaanlgarviepg |
| BAAT3ML | 301 | tfgkraypggltysghplacaaavatinvmaeegvvenaanlgarviepg |
| BAAT5-9 | 301 | tfgkraypggltysghplacaaavatinvmaeegvvenaanlgarviepg |
| | | |
| WT BAAT | 351 | lrelaerhpsvgevrgvgmfwalelvkdretreplvpynaageanapmaa |
| BAAT1 | 351 | lrelaerhpsvgevrgvgmfwalelvkdretreplvpynaageanapmaa |
| BAAT2 | 351 | lrelaerhpsvgevrgvgmfwalelvkdretreplvpynaageanapmaa |
| BAAT3 | 351 | lrelaerhpsvgevrgvgmfwalelvkdretreplvpynaageanapmaa |
| BAATP3H | 351 | lrelaerhpsvgevrgvgmfwalelvkdretreplvpynaageanapmaa |
| BAAT3ML | 351 | lrelaerhpsvgevrgvgmfwalelvkdretreplvpynaageanapmaa |
| BAAT5-9 | 351 | lrelaerhpsvgevrgvgmfwalelvkdretreplvpynaageanapmaa |
| | | |
| WT BAAT | 401 | fgaaakanglwpfinmnrthvvppcnvteaeakeglaaldaalsvadeyt |
| BAAT1 | 401 | fgaaakanglwpfinmnrthvvppcnvteaeakeglaaldaalsvadeyt |
| BAAT2 | 401 | fgaaakanglwpfinmnrthvvppcnvteaeakeglaaldaalsvadeyt |
| BAAT3 | 401 | fgaaakanglwpfinmnrthvvppcnvteaeakeglaaldaalsvadeyt |
| BAATP3H | 401 | fgaaakanglwpfinmnrthvvppcnvteaeakeglaaldaalsvadeyt |
| BAAT3ML | 401 | fgaaakanglwpfinmnrthvvppcnvteaeakeglaaldaalsvadeyt |
| BAAT5-9 | 401 | fgaaakanglwpfinmnrthvvppcnvteaeakeglaaldaalsvadeyt |
| | | |
| WT BAAT | 451 | v- |
| BAAT1 | 451 | v- |
| BAAT2 | 451 | v- |
| BAAT3 | 451 | v- |
| BAATP3H | 451 | v- |
| BAAT3ML | 451 | v- |
| BAAT5-9 | 451 | v- |

US 8,030,045 B2

SEQUENCE LISTING

```
<160> NUMBER OF SEQ ID NOS: 59

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 1
cgggatccct aaaccgtgta ctcgtcc                                    27

<210> SEQ ID NO 2
<211> LENGTH: 29
```

```
<212> TYPE: DNA
<213> ORGANISM: Artificial sequence
<220> FEATURE:
<223> OTHER INFORMATION: Synthetic oligonucleotide primer

<400> SEQUENCE: 2
ggaattccat atgacccctc agccgaatc                                      29

<210> SEQ ID NO 3
<211> LENGTH: 1356
<212> TYPE: DNA
<213> ORGANISM: Streptomyces avermitilis

<400> SEQUENCE: 3
atgacccctc agccgaatcc ccaggtcggt gccgccgtca aggccgcgga ccgtgcgcat      60
gtcttccact cctggtcagc gcaggagctc atcgacccgc tcgccgtcgc cggtgcggag     120
gggtcgtact tctgggacta cgacggcagg cggtacctgg acttcaccag cggactcgtc     180
ttcaccaaca tcgggtacca gcaccccaag gtcgtcgccg ccattcagga gcaggccgcg     240
agcctgacca ccttcgcgcc cgccttcgcc gtcgaggcgc ggtccgaggc ggcccggctc     300
atcgccgagc ggacgcccgg agacctcgac aagatcttct tcaccaacgg cggggccgac     360
gccatcgagc acgccgtgcg catggcgcgg atacacgccg gcggcccaa ggtgctgtcc      420 gcctaccgct cctaccacgg tggcacccag caggccgtca acatcaccgg tgatccgcgc     480
cgctgggcct ccgacagcgc ctcggcgggc gtcgtgcact tctgggcgcc gtacctctac     540
cggtcgcgct tctacgcgga gaccgagcag caggagtgtg agcgggcgct ggagcacctg     600
gagacgacca tcgccttcga ggggccgggc acgatcgccg cgatcgtgct ggagaccgtt     660
ccggggaccg cggggatcat ggttccgccg cccggatatc tcgccggggt gcgtgagctg     720
tgcgacaagt acggcatcgt cttcgtcctg gacgaggtga tggccgggtt cggacggacc     780
ggtgagtggt tcgccgcgga tctcttcgac gtcacacccg acctgatgac cttcgccaag     840
ggcgtgaact ccggatatgt gccgctgggc ggtgtcgcga tctccgggaa gatcgccgag     900
accttcggga gcgggcccta cccggccggt ctgacctact ccgggcatcc gctcgcctgc     960
gccgccgccg tcgccacgat caacgtcatg gccgaggagg gggtcgtcga aacgcggcg     1020 aacctcggcg cccgggtcat cgagccgggg ctgcgcgagc tggccgagcg caccccgtcc     1080
gtgggcgagg tgcgcggtgt cggcatgttc tgggcgctgg agctggtcaa ggaccgggag     1140
acgcgggagc cgctggtgcc gtacaacgcg gcgggcgagg cgaacgcgcc gatggccgcc     1200
ttcggtgccg ccgccaaggc gaacggcctg tggccgttca tcaacatgaa ccgcacgcac     1260
gtcgtgcccc cgtgcaacgt cacggaggcc gaggccaagg aaggcctggc ggccctcgac     1320
gcggccctct cggtggcgga cgagtacacg gtttag                              1356

<210> SEQ ID NO 4
<211> LENGTH: 451
<212> TYPE: PRT
<213> ORGANISM: Streptomyces avermitilis

<400> SEQUENCE: 4

Met Thr Pro Gln Pro Asn Pro Gln Val Gly Ala Ala Val Lys Ala Ala
1               5                   10                  15

Asp Arg Ala His Val Phe His Ser Trp Ser Ala Gln Glu Leu Ile Asp
                20                  25                  30

Pro Leu Ala Val Ala Gly Ala Glu Gly Ser Tyr Phe Trp Asp Tyr Asp
            35                  40                  45
```

Gly Arg Arg Tyr Leu Asp Phe Thr Ser Gly Leu Val Phe Thr Asn Ile
    50                  55                  60

Gly Tyr Gln His Pro Lys Val Val Ala Ala Ile Gln Glu Gln Ala Ala
65                  70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Phe Phe Thr Asn Gly Gly Ala Asp Ala Ile Glu His Ala Val Arg Met
        115                 120                 125

Ala Arg Ile His Ala Gly Arg Pro Lys Val Leu Ser Ala Tyr Arg Ser
    130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
        195                 200                 205

Pro Gly Thr Ile Ala Ala Ile Val Leu Glu Thr Val Pro Gly Thr Ala
    210                 215                 220

Gly Ile Met Val Pro Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
        275                 280                 285

Leu Gly Gly Val Ala Ile Ser Gly Lys Ile Ala Glu Thr Phe Gly Lys
    290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Glu Pro Gly Leu Arg
            340                 345                 350

Glu Leu Ala Glu Arg His Pro Ser Val Gly Glu Val Arg Gly Val Gly
        355                 360                 365

Met Phe Trp Ala Leu Glu Leu Val Lys Asp Arg Glu Thr Arg Glu Pro
    370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
        435                 440                 445

Tyr Thr Val
    450

<210> SEQ ID NO 5

<211> LENGTH: 1356
<212> TYPE: DNA
<213> ORGANISM: Streptomyces avermitilis

<400> SEQUENCE: 5

```
atgacccctc agccgaatcc ccaggtcggt gccgccgtca aggccgcgga ccgtgcgcat      60
gtcttccaca cctggtcagc gcaggagctc atcgacccgc tcgccgtcgc cggtgcggag     120
gggtcgtact tctgggacta cgacggcagg cggtacctgg acttcaccag cggactcgtc     180
ttcaccaaca tcgggtacca gcaccccaag gtcgtcgccg ccattcagga gcaggccgcg     240
agcctgacca ccttcgcgcc cgccttcgcc gtcgaggcgc ggtccgaggc ggccggctc      300
atcgccgagc ggacgcccgg agacctcgac aagatcttct tcaccaacgg cggggccgac     360
gccatcgagc acgccgtgcg catggcgcgg atacacgccg gcggcccaa ggtgctgtcc      420
gcctaccgct cctaccacgg tggcacccag caggccgtca acatcaccgg tgatccgcgc     480
cgctgggcct ccgacagcgc ctcggcgggc gtcgtgcact tctgggcgcc gtacctctac     540
cggtcgcgct tctacgcgga gaccgagcag caggagtgtg agcgggcgct ggagcacctg     600
gagacgacca tcgccttcga ggggccgggc acgatcgccg cgatcgtgct ggagaccgtt     660
ccggggaccg cggggatcat ggttccgccg cccggatatc tcgccggggt gcgtgagctg     720
tgcgacaagt acggcatcgt cttcgtcctg gacgaggtga tggccgggtt cggacggacc     780
ggtgagtggt tcgccgcgga tctcttcgac gtcacacccg acctgatgac cttcgccaag     840
ggcgtgaact ccggatatgt gccgctgggc ggtgtcgcga tctccgggaa gatcgccgag     900
accttcggga agcgggccta cccgggcggt ctgacctact ccgggcatcc gctcgcctgc     960
gccgccgccg tcgccacgat caacgtcatg gccgaggagg gggtcgtcga gaacgcggcg    1020
aacctcggcg cccgggtcat cgagccgggg ctgcgcgagc tggccgagcg gcacccgtcc    1080
gtgggcgagg tgcgcggtgt cggcatgttc tgggcgctgg agctggtcaa ggaccgggag    1140
acgcgggagc cgctggtgcc gtacaacgcg gcgggcgagg cgaacgcgcc gatggccgcc    1200
ttcggtgccg ccgccaaggc gaacggcctg tggccgttca tcaacatgaa ccgcacgcac    1260
gtcgtgcccc cgtgcaacgt cacggaggcc gaggccaagg aaggcctggc ggccctcgac    1320
gcggccctct cggtggcgga cgagtacacg gtttag                              1356
```

<210> SEQ ID NO 6
<211> LENGTH: 451
<212> TYPE: PRT
<213> ORGANISM: Streptomyces avermitilis

<400> SEQUENCE: 6

Met Thr Pro Gln Pro Asn Pro Gln Val Gly Ala Ala Val Lys Ala Ala
1               5                   10                  15

Asp Arg Ala His Val Phe His Thr Trp Ser Ala Gln Glu Leu Ile Asp
            20                  25                  30

Pro Leu Ala Val Ala Gly Ala Glu Gly Ser Tyr Phe Trp Asp Tyr Asp
        35                  40                  45

Gly Arg Arg Tyr Leu Asp Phe Thr Ser Gly Leu Val Phe Thr Asn Ile
    50                  55                  60

Gly Tyr Gln His Pro Lys Val Val Ala Ala Ile Gln Glu Gln Ala Ala
65                  70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Phe Phe Thr Asn Gly Gly Ala Asp Ala Ile Glu His Ala Val Arg Met
            115                 120                 125

Ala Arg Ile His Ala Gly Arg Pro Lys Val Leu Ser Ala Tyr Arg Ser
130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Gln Gln Gln Glu
            180                 185                 190

Cys Glu Arg Ala Leu Glu His Leu Glu Thr Thr Ile Ala Phe Glu Gly
            195                 200                 205

Pro Gly Thr Ile Ala Ala Ile Val Leu Glu Thr Val Pro Gly Thr Ala
        210                 215                 220

Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
        275                 280                 285

Leu Gly Gly Val Ala Ile Ser Gly Lys Ile Ala Glu Thr Phe Gly Lys
290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Glu Pro Gly Leu Arg
            340                 345                 350

Glu Leu Ala Glu Arg His Pro Ser Val Gly Glu Val Arg Gly Val Gly
        355                 360                 365

Met Phe Trp Ala Leu Glu Leu Val Lys Asp Arg Glu Thr Arg Glu Pro
370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
        435                 440                 445

Tyr Thr Val
    450

<210> SEQ ID NO 7
<211> LENGTH: 1356
<212> TYPE: DNA
<213> ORGANISM: Streptomyces avermitilis

<400> SEQUENCE: 7
atgacccctc agccgaatcc ccaggtcggt gccgccgtca aggccgcgga ccgtgcgcat      60
gtcttccact cctggtcagc gcaggagctc atcgacccgc tcgccgtcgc cggtgcggag    120
gggtcgtact tctgggacta cgacggcagg cggtacctgg acttcaccag cggactcgtc    180

```
ttcaccaaca tcgggtacca gcaccccaag gtcgtcgccg ccattcagga gcaggccgcg      240
agcctggcca ccttcgcgcc cgccttcgcc gtcgaggcgc ggtccgaggc ggcccggctc      300
atcgccgagc ggacgcccgg agacctcgac aagatcttct tcaccaacgg cggggccgac      360
gccatcgagc acgccgtgcg catggcgcgg atacacgccg gcggcccaa  ggtgctgtcc      420 gcctaccgct cctaccacgg tggcacccag caggccgtca acatcaccgg tgatccgcgc      480
cgctgggcct ccgacagcgc ctcggcgggc gtcgtgcact tctgggcgcc gtacctctac      540
cggtcgcgct tctacgcgga gaccgagcag caggagtgtg agcgggcgct ggagcacctg      600
gagacgacca tcgccttcga ggggccgggc acgatcgccg cgatcgtgct ggagaccgtt      660
ccggggaccg cggggatcat ggttccgccg cccggatatc tcgccggggt gcgtgagctg      720
tgcgacaagt acggcatcgt cttcgtcctg gacgaggtga tggccgggtt cggacggacc      780
ggtgagtggt tcgccgcgga tctcttcgac gtcacacccg acctgatgac cttcgccaag      840
ggcgtgaact ccggatatgt gccgctgggc ggtgtcgcga tctccgggaa gatcgccgag      900
accttcggga agcgggccta cccgggcggt ctgacctaca ccgggcatcc gctcgcctgc      960
gccgccgccg tcgccacgat caacgtcatg gccgaggagg gggtcgtcga aacgcggcg     1020 aacctcggcg cccgggtcat cgggccgggg ctgcgcgagc tggccgagcg gcacccgtcc     1080
gtgggcgagg tgcgcggtgt cggcatgttc tgggcgctgg agctggtcaa ggaccgggag     1140
acgcgggagc cgctggtgcc gtacaacgcg gcgggcgagg cgaacgcgcc gatggccgcc     1200
ttcggtgccg ccgccaaggc gaacggcctg tggccgttca tcaacatgaa ccgcacgcac     1260
gtcgtgcccc cgtgcaacgt cacggaggcc gaggccaagg aaggcctggc ggccctcgac     1320
gcggccctct cggtggcgga cgagtacacg gtttag                              1356

<210> SEQ ID NO 8
<211> LENGTH: 451
<212> TYPE: PRT
<213> ORGANISM: Streptomyces avermitilis

<400> SEQUENCE: 8

Met Thr Pro Gln Pro Asn Pro Gln Val Gly Ala Ala Val Lys Ala
1               5                   10                  15

Asp Arg Ala His Val Phe His Ser Trp Ser Ala Gln Glu Leu Ile Asp
            20                  25                  30

Pro Leu Ala Val Ala Gly Ala Glu Gly Ser Tyr Phe Trp Asp Tyr Asp
        35                  40                  45

Gly Arg Arg Tyr Leu Asp Phe Thr Ser Gly Leu Val Phe Thr Asn Ile
    50                  55                  60

Gly Tyr Gln His Pro Lys Val Val Ala Ala Ile Gln Glu Gln Ala Ala
65                  70                  75                  80

Ser Leu Ala Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Phe Phe Thr Asn Gly Gly Ala Asp Ala Ile Glu His Ala Val Arg Met
        115                 120                 125

Ala Arg Ile His Ala Gly Arg Pro Lys Val Leu Ser Tyr Arg Ser
            130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
```

```
                        165                 170                 175
Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
            195                 200                 205

Pro Gly Thr Ile Ala Ala Ile Val Leu Glu Thr Val Pro Gly Thr Ala
            210                 215                 220

Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
            275                 280                 285

Leu Gly Gly Val Ala Ile Ser Gly Lys Ile Ala Glu Thr Phe Gly Lys
            290                 295                 300

Arg Ala Tyr Pro Gly Gly Leu Thr Tyr Thr Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Gly Pro Gly Leu Arg
            340                 345                 350

Glu Leu Ala Glu Arg His Pro Ser Val Gly Glu Val Arg Gly Val Gly
            355                 360                 365

Met Phe Trp Ala Leu Glu Leu Val Lys Asp Arg Glu Thr Arg Glu Pro
370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
            435                 440                 445

Tyr Thr Val
        450

<210> SEQ ID NO 9
<211> LENGTH: 1356
<212> TYPE: DNA
<213> ORGANISM: Streptomyces avermitilis

<400> SEQUENCE: 9
atgacccctc agccgaatcc ccaggtcggt gccgccgtca aggccgcgga ccgtgcgcat      60
gtcttccaca cctggtcagc gcaggagctc atcgaccgc tcgccgtcgc cggtgcggag     120
gggtcgtact tctgggacta cgacggcagg cggtacctgg acttcaccag cggactcgtc     180
ttcaccaaca tcgggtacca gcaccccaag gtcgtcgccg ccattcagga gcaggccgcg     240
agcctgacca cctcgcgcc cgccttcgcc gtcgaggcgc ggtccgaggc ggcccggctc     300
atcgccgagc ggacgcccgg agacctcgac aagatcctct tcaccaacgg cggggccgac     360
gccatcgagc acgccgtgcg catggcgcg atacacgccg gcggcccaa ggtgctgtcc     420 gcataccgct cctaccacgg tggcacccag caggccgtca acatcaccgg tgatccgcgc     480
```

```
cgctgggcct ccgacagcgc ctcggcgggc gtcgtgcact tctgggcgcc gtacctctac     540
cggtcgcgct tctacgcgga gaccgagcag caggagtgtg agcgggcgct ggagcacctg     600
gagacgacca tcgccttcga ggggccgggc acgatcgccg cgatcgtgct ggagaccgtt     660
ccggggaccg cggggatcat ggttccgccg cccggatatc tcgccggggt gcgtgagctg     720
tgcgacaagt acggcatcgt cttcgtcctg gacgaggtga tggccgggtt cggacggacc     780
ggtgagtggt tcgccgcgga tctcttcgac gtcacacccg acctgatgac cttcgccaag     840
ggcgtgaact ccggatatgt gccgctgggc ggtgtcgcga tctccgggaa gatcgccgag     900
accttcggga agcgggccta cccgggcggt ctgacctact ccgggcatcc gctcgcctgc     960
gccgccgccg tcgccacgat caacgtcatg gccgaggagg gggtcgtcga aacgcggcg    1020 aacctcggcg cccgggtcat cgagccgggg ctgcgcgagc tggccgagcg caccccgtcc    1080
gtgggcgagg tgcgcggtgt cggcatgttc tgggcgctgg agctggtcaa ggaccgggag    1140
acgcgggagc cgctggtgcc gtacaacgcg cgggcgagg cgaacgcgcc gatgccgcc    1200 ttcggtgccg ccgccaaggc gaacggcctg tggccgttca tcaacatgaa ccgcacgcac    1260
gtcgtgcccc cgtgcaacgt cacggaggcc gaggccaagg aaggcctggc ggccctcgac    1320
gcggccctct cggtggcgga cgagtacacg gtttag                              1356
```

<210> SEQ ID NO 10
<211> LENGTH: 451
<212> TYPE: PRT
<213> ORGANISM: Streptomyces avermitilis

<400> SEQUENCE: 10

```
Met Thr Pro Gln Pro Asn Pro Gln Val Gly Ala Ala Val Lys Ala Ala
1               5                   10                  15

Asp Arg Ala His Val Phe His Thr Trp Ser Ala Gln Glu Leu Ile Asp
            20                  25                  30

Pro Leu Ala Val Ala Gly Ala Glu Gly Ser Tyr Phe Trp Asp Tyr Asp
        35                  40                  45

Gly Arg Arg Tyr Leu Asp Phe Thr Ser Gly Leu Val Phe Thr Asn Ile
    50                  55                  60

Gly Tyr Gln His Pro Lys Val Val Ala Ile Gln Glu Gln Ala Ala
65                  70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Leu Phe Thr Asn Gly Gly Ala Asp Ala Ile Glu His Ala Val Arg Met
        115                 120                 125

Ala Arg Ile His Ala Gly Arg Pro Lys Val Leu Ser Ala Tyr Arg Ser
    130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
        195                 200                 205

Pro Gly Thr Ile Ala Ala Ile Val Leu Glu Thr Val Pro Gly Thr Ala
    210                 215                 220
```

```
Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
            245                 250                 255

Phe Gly Arg Thr Gly Glu Trp Phe Ala Ala Asp Leu Phe Asp Val Thr
        260                 265                 270

Pro Asp Leu Met Thr Phe Ala Lys Gly Val Asn Ser Gly Tyr Val Pro
            275                 280                 285

Leu Gly Gly Val Ala Ile Ser Gly Lys Ile Ala Glu Thr Phe Gly Lys
290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Glu Pro Gly Leu Arg
            340                 345                 350

Glu Leu Ala Glu Arg His Pro Ser Val Gly Glu Val Arg Gly Val Gly
        355                 360                 365

Met Phe Trp Ala Leu Glu Leu Val Lys Asp Arg Glu Thr Arg Glu Pro
370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Leu Asp Ala Ala Leu Ser Val Ala Asp Glu
        435                 440                 445

Tyr Thr Val
    450

<210> SEQ ID NO 11
<211> LENGTH: 1356
<212> TYPE: DNA
<213> ORGANISM: Streptomyces avermitilis

<400> SEQUENCE: 11
atgacccccc agccgaatcc ccaggtcggt gccgccgtca aggccgcgga ccgtgcgcat      60
gtcttccaca cctggtcagc gcaggagctc atcgacccgc tcgccgtcgc cggtgcggag     120
gggtcgtact tctgggacta cgacggcagg cggtacctgg acttcaccag cggactcgtc     180
ttcaccaaca tcgggtacca gcaccccaag gtcgtcgccg ccattcagga gcaggccgcg     240
agcctgacca ccttcgcgcc cgccttcgcc gtcgaggcgc ggtccgaggc ggcccggctc     300
atcgccgagc ggacgcccgg agacctcgac aagatcctct tcaccaacgg cggggccgac     360
gccatcgagc acgccgtgcg catggcgcgg atacacaccg gcggcccaa ggtgctgtcc      420 gcataccgct cctaccacgg tggcacccag caggccgtca acatcaccgg tgatccgcgc     480
cgctgggcct ccgacagcgc ctcggcgggc gtcgtgcact ctgggcgcc gtacctctac      540 cggtcgcgct tctacgcgga gaccgagcag caggagtgtg agcgggcgct ggagcacctg     600
gagacgacca tcgccttcga ggggccgggc acgatcgccg cgatcgtgct ggagaccgtt     660
ccggggaccg cggggatcat ggttccgccg cccggatatc tcgccggggt gcgtgagctg     720
tgcgacaagt acggcatcgt cttcgtcctg gacgaggtga tggccgggtt cggacggacc     780
ggtgagtggt tcgccgcgga tctcttcgac gtcacacccg acctgatgac cttcgccaag     840
```

```
ggcgtgaact ccggatatgt gccgctgggc ggtgtcgcga tctccgggaa gatcgccgag      900
accttcggga agcgggccta cccgggcggt ctgacctact ccgggcatcc gctcgcctgc      960
gccgccgccg tcgccacgat caacgtcatg gccgaggagg gggtcgtcga gaacgcggcg     1020
aacctcggcg cccgggtcat cgagccgggg ctgcgcgagc tggccgagcg gcacccgtcc     1080
gtgggcgagg tgcgcggtgt cggcatgttc tgggcgctgg agctggtcaa ggaccgggag     1140
acgcgggagc cgctggtgcc gtacaacgcg gcgggcgagg cgaacgcgcc gatggccgcc     1200
ttcggtgccg ccgccaaggc gaacggcctg tggccgttca tcaacatgaa ccgcacgcac     1260
gtcgtgcccc cgtgcaacgt cacggaggcc gaggccaagg aaggcctggc ggccctcgac     1320
gcggccctct cggtggcgga cgagtacacg gtttag                               1356
```

```
<210> SEQ ID NO 12
<211> LENGTH: 451
<212> TYPE: PRT
<213> ORGANISM: Streptomyces avermitilis

<400> SEQUENCE: 12

Met Thr Pro Gln Pro Asn Pro Gln Val Gly Ala Ala Val Lys Ala Ala
1               5                   10                  15

Asp Arg Ala His Val Phe His Thr Trp Ser Ala Gln Glu Leu Ile Asp
            20                  25                  30

Pro Leu Ala Val Ala Gly Ala Glu Gly Ser Tyr Phe Trp Asp Tyr Asp
        35                  40                  45

Gly Arg Arg Tyr Leu Asp Phe Thr Ser Gly Leu Val Phe Thr Asn Ile
    50                  55                  60

Gly Tyr Gln His Pro Lys Val Val Ala Ile Gln Glu Gln Ala Ala
65                  70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Leu Phe Thr Asn Gly Gly Ala Asp Ala Ile Glu His Ala Val Arg Met
        115                 120                 125

Ala Arg Ile His Thr Gly Arg Pro Lys Val Leu Ser Ala Tyr Arg Ser
    130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val His Phe Trp Ala
                165                 170                 175

Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
        195                 200                 205

Pro Gly Thr Ile Ala Ala Ile Val Leu Glu Thr Val Pro Gly Thr Ala
    210                 215                 220

Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
        275                 280                 285
```

```
Leu Gly Gly Val Ala Ile Ser Gly Lys Ile Ala Glu Thr Phe Gly Lys
    290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Glu Pro Gly Leu Arg
            340                 345                 350

Glu Leu Ala Glu Arg His Pro Ser Val Gly Glu Val Arg Gly Val Gly
        355                 360                 365

Met Phe Trp Ala Leu Glu Leu Val Lys Asp Arg Glu Thr Arg Glu Pro
    370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
        435                 440                 445

Tyr Thr Val
    450

<210> SEQ ID NO 13
<211> LENGTH: 1356
<212> TYPE: DNA
<213> ORGANISM: Streptomyces avermitilis

<400> SEQUENCE: 13
atgacccatc agccgaatcc ccaggtcggt gccgccgtca aggccgcgga ccgtgcgcat    60
gtcttccact cctggtcagc gcaggagctc atcgacccgc tcgccgtcgc cggtgcggag   120
gggtcgtact tctgggacta cgacggcagg cggtacctgg acttcaccag cggactcgtc   180
ttcaccaaca tcgggtacca gcaccccaag gtcgtcgccg ccattcagga gcaggccgcg   240
agcctgacca ccttcgcgcc cgccttcgcc gtcgaggcgc ggtccgaggc ggcccggctc   300
atcgccgagc ggacgcccgg agacctcgac aagatcttct tcaccaacgg cggggccgac   360
gccatcgagc acgccgtgcg catggcgcgg atacacgccg gcggcccaa ggtgctgtcc    420 gcctaccgct cctaccacgg tgcacccag caggccgtca acatcaccgg tgatccgcgc    480
cgctgggcct ccgacagcgc ctcggcgggc gtcgtgcact tctgggcgcc gtacctctac   540
cggtcgcgct tctacgcgga gaccgagcag caggagtgtg agcgggcgct ggagcacctg   600
gagacgacca tcgccttcga ggggccgggc acgatcgccg catcgtgct ggagaccgtt    660 ccggggaccg cggggatcat ggttccgccg cccggatatc tcgccgggt gcgtgagctg    720 tgcgacaagt acggcatcgt cttcgtcctg acgaggtga tggccgggtt cggacggacc    780
ggtgagtggt tcgccgcgga tctcttcgac gtcacacccg acctgatgac cttcgccaag   840
ggcgtgaact ccggatatgt gccgctgggc ggtgtcgcga tctccgggaa gatcgccgag   900
accttcggga gcgggcccta cccggcgcgt ctgacctact ccgggcatcc gctcgcctgc   960
gccgccgccg tcgccacgat caacgtcatg gccgaggagg gggtcgtcga aacgcggcg   1020 aacctcggcg cccgggtcat cgagccgggg ctgcgcgagc tggccgagcg caccgtcc    1080 gtgggcgagg tgcgcggtgt cggcatgttc tgggcgctgg agctggtcaa ggaccggag   1140
```

```
acgcgggagc cgctggtgcc gtacaacgcg gcgggcgagg cgaacgcgcc gatggccgcc    1200
ttcggtgccg ccgccaaggc gaacggcctg tggccgttca tcaacatgaa ccgcacgcac    1260
gtcgtgcccc cgtgcaacgt cacggaggcc gaggccaagg aaggcctggc ggccctcgac    1320
gcggccctct cggtggcgga cgagtacacg gtttag                              1356
```

<210> SEQ ID NO 14
<211> LENGTH: 451
<212> TYPE: PRT
<213> ORGANISM: Streptomyces avermitilis

<400> SEQUENCE: 14

```
Met Thr His Gln Pro Asn Pro Gln Val Gly Ala Ala Val Lys Ala Ala
1               5                   10                  15

Asp Arg Ala His Val Phe His Ser Trp Ser Ala Gln Glu Leu Ile Asp
            20                  25                  30

Pro Leu Ala Val Ala Gly Ala Glu Gly Ser Tyr Phe Trp Asp Tyr Asp
        35                  40                  45

Gly Arg Arg Tyr Leu Asp Phe Thr Ser Gly Leu Val Phe Thr Asn Ile
    50                  55                  60

Gly Tyr Gln His Pro Lys Val Val Ala Ala Gln Glu Gln Ala Ala
65                  70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Phe Phe Thr Asn Gly Gly Ala Asp Ala Ile Glu His Ala Val Arg Met
        115                 120                 125

Ala Arg Ile His Ala Gly Arg Pro Lys Val Leu Ser Ala Tyr Arg Ser
    130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
        195                 200                 205

Pro Gly Thr Ile Ala Ala Ile Val Leu Glu Thr Val Pro Gly Thr Ala
    210                 215                 220

Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
        275                 280                 285

Leu Gly Gly Val Ala Ile Ser Gly Lys Ile Ala Glu Thr Phe Gly Lys
    290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Glu Pro Gly Leu Arg
```

```
                  340             345             350
Glu Leu Ala Glu Arg His Pro Ser Val Gly Glu Val Arg Gly Val Gly
            355                 360                 365

Met Phe Trp Ala Leu Glu Leu Val Lys Asp Arg Glu Thr Arg Glu Pro
    370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
        435                 440                 445

Tyr Thr Val
        450

<210> SEQ ID NO 15
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 15
aaggtacata tgacccatca gccgaatccc                                        30

<210> SEQ ID NO 16
<211> LENGTH: 1356
<212> TYPE: DNA
<213> ORGANISM: Streptomyces avermitilis

<400> SEQUENCE: 16
atgacccatc agccgaatcc ccaggtcggt gccgccgtca aggccgcgga ccgtgcgcat        60
gtcttccaca cctggtcagc gcaggagctc atcgacccgc tcgccgtcgc cggtgcggag      120
gggtcgtact tctgggacta cgacggcagg cggtacctgg acttcaccag cggactcgtc      180
ttcaccaaca tcgggtacca gcaccccaag gtcgtcgccg ccattcagga gcaggccgcg      240
agcctgacca ccttcgcgcc cgccttcgcc gtcgaggcgc ggtccgaggc ggcccggctc      300
atcgccgagc ggacgcccgg agacctcgac aagatcctct tcaccaacgg cggggccgac      360
gccatcgagc acgccgtgcg catggcgcgg atacacaccg gcggcccaa ggtgctgtcc      420 gcataccgct cctaccacgg tggcacccag caggccgtca acatcaccgg tgatccgcgc      480
cgctgggcct ccgacagcgc ctcggcgggc gtcgtgcact tctgggcgcc gtacctctac      540
cggtcgcgct tctacgcgga gaccgagcag caggagtgtg agcgggcgct ggagcacctg      600
gagacgacca tcgccttcga ggggccgggc acgatcgccg cgatcgtgct ggagaccgtt      660
ccggggaccg cggggatcat ggttccgccg cccggatatc tcgccggggt gcgtgagctg      720
tgcgacaagt acggcatcgt cttcgtcctg gacgaggtga tggccgggtt cggacggacc      780
ggtgagtggt tcgccgcgga tctcttcgac gtcacacccg acctgatgac cttcgccaag      840
ggcgtgaact ccggatatgt gccgctgggc ggtgtcgcga tctccgggaa gatcgccgag      900
accttcggga agcgggccta cccgggcggt ctgacctact ccgggcatcc gctcgcctgc      960
gccgccgccg tcgccacgat caacgtcatg gccgaggagg gggtcgtcga gaacgcggcg     1020
aacctcggcg cccgggtcat cgagccgggg ctgcgcgagc tggccgagcg gcaccgtcc     1080 gtgggcgagg tgcgcggtgt cggcatgttc tgggcgctgg agctggtcaa ggaccgggag     1140
```

-continued

```
acgcgggagc cgctggtgcc gtacaacgcg gcgggcgagg cgaacgcgcc gatggccgcc    1200
ttcggtgccg ccgccaaggc gaacggcctg tggccgttca tcaacatgaa ccgcacgcac    1260
gtcgtgcccc cgtgcaacgt cacggaggcc gaggccaagg aaggcctggc ggccctcgac    1320
gcggccctct cggtggcgga cgagtacacg gtttag                              1356
```

<210> SEQ ID NO 17
<211> LENGTH: 451
<212> TYPE: PRT
<213> ORGANISM: Streptomyces avermitilis

<400> SEQUENCE: 17

```
Met Thr His Gln Pro Asn Pro Gln Val Gly Ala Ala Val Lys Ala Ala
1               5                   10                  15

Asp Arg Ala His Val Phe His Thr Trp Ser Ala Gln Glu Leu Ile Asp
            20                  25                  30

Pro Leu Ala Val Ala Gly Ala Glu Gly Ser Tyr Phe Trp Asp Tyr Asp
        35                  40                  45

Gly Arg Arg Tyr Leu Asp Phe Thr Ser Gly Leu Val Phe Thr Asn Ile
    50                  55                  60

Gly Tyr Gln His Pro Lys Val Val Ala Ala Ile Gln Glu Gln Ala Ala
65                  70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
            100                 105                 110

Leu Phe Thr Asn Gly Gly Ala Asp Ala Ile Glu His Ala Val Arg Met
        115                 120                 125

Ala Arg Ile His Thr Gly Arg Pro Lys Val Leu Ser Ala Tyr Arg Ser
    130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
        195                 200                 205

Pro Gly Thr Ile Ala Ala Ile Val Leu Glu Thr Val Pro Gly Thr Ala
    210                 215                 220

Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
        275                 280                 285

Leu Gly Gly Val Ala Ile Ser Gly Lys Ile Ala Glu Thr Phe Gly Lys
    290                 295                 300

Arg Ala Tyr Pro Gly Gly Leu Thr Tyr Ser Gly His Pro Leu Ala Cys
305                 310                 315                 320

Ala Ala Val Ala Thr Ile Asn Val Met Ala Glu Glu Gly Val Val
                325                 330                 335
```

```
Glu Asn Ala Ala Asn Leu Gly Ala Arg Val Ile Glu Pro Gly Leu Arg
                340                 345                 350

Glu Leu Ala Glu Arg His Pro Ser Val Gly Glu Val Arg Gly Val Gly
            355                 360                 365

Met Phe Trp Ala Leu Glu Leu Val Lys Asp Arg Glu Thr Arg Glu Pro
    370                 375                 380

Leu Val Pro Tyr Asn Ala Ala Gly Glu Ala Asn Ala Pro Met Ala Ala
385                 390                 395                 400

Phe Gly Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
                420                 425                 430

Lys Glu Gly Leu Ala Ala Leu Asp Ala Ala Leu Ser Val Ala Asp Glu
            435                 440                 445

Tyr Thr Val
    450

<210> SEQ ID NO 18
<211> LENGTH: 1356
<212> TYPE: DNA
<213> ORGANISM: Streptomyces avermitilis

<400> SEQUENCE: 18
atgacccatc agccgaatcc ccaggtcggt gccgccgtca aggccgcgga ccgtgcgcat      60
gtcttccaca cctggtcagc gcaggagctc atcgacccgc tcgccgtcgc cggtgcggag     120
gggtcgtact tctgggacta cgacggcagg cggtacctgg acttcaccag cggactcgtc     180
ttcaccaaca tcgggtacca gcaccctaag gtcgtcgccg ccattcagga gcaggccgcg     240
agcctgacca ccttcgcgcc cgccttcgcc gtcgaggcgc ggtccgaggc ggcccggctc     300
atcgccgagc ggacgcccgg agacctcaac aagatcctct tcaccaacgg cggggccgac     360
gccatcgagc acgccgtgcg gatggcgcgg atacacaccg gcggcgccaa ggtgctgtcc     420
gcataccgct cctaccacgg tggcacccca caggccgtca acatcaccgg cgatccgcgc     480
cgctgggcct ccgacagcgc ctcggcgggc gtcgtgcact tctgggcgcc gtacctctac     540
cggtcgcgct tctacgcgga gaccgagcag caggagtgtg agcgggcgct ggagcacctg     600
gagacgacca tcgccttcga ggggccgggc acgatcgccg cgatcgtgct ggagaccgtt     660
ccggggaccg cggggatcat ggttccgccg cccggatatc tcgccggggt gcgtgagctg     720
tgcgacaagt acggcatcgt cttcgtcctg gacgaggtga tggccgggtt cggacggacc     780
ggtgagtggt tcgccgcgga tctcttcgac gtcacacccg acctgatgac cttcgccaag     840
ggcgtgaact ccggatatgt gccgctgggc ggtgtcgcga tctccgggaa gatcgccgag     900
accttcggga agcgggccta cccgggcggt ctgacctact ccgggcatcc gctcgcctgc     960
gccgccgccg tcgccacgat caacgtcatg gccgaggagg gggtcgtcga gaacgcggcg    1020
aacctcggcg cccgggtcat cgagccgggg ctgcgcgagc tggccgagcg gcacccgtcc    1080
gtgggcgagg tgcgcggtgt cggcatgttc tgggcgctgg agctggtcaa ggaccgggag    1140
acgcgggagc cgctggtgcc gtacaacgcg gcgggcgagg cgaacgcgcc gatggccgcc    1200
ttcggtgccg ccgccaaggc gaacggcctg tggccgttca tcaacatgaa ccgcacgcac    1260
gtcgtgcccc cgtgcaacgt cacggaggcc gaggccaagg aaggcctggc ggccctcgac    1320
gcggccctct cggtggcgga cgagtacacg gtttag                              1356

<210> SEQ ID NO 19
```

```
<211> LENGTH: 451
<212> TYPE: PRT
<213> ORGANISM: Streptomyces avermitilis

<400> SEQUENCE: 19
```

| | | | | | | | | | | | | | | |
|---|---|---|---|---|---|---|---|---|---|---|---|---|---|---|
| Met | Thr | His | Gln | Pro | Asn | Pro | Gln | Val | Gly | Ala | Ala | Val | Lys | Ala | Ala |
| 1 | | | | 5 | | | | | 10 | | | | | 15 | |
| Asp | Arg | Ala | His | Val | Phe | His | Thr | Trp | Ser | Ala | Gln | Glu | Leu | Ile | Asp |
| | | | 20 | | | | | 25 | | | | | 30 | | |
| Pro | Leu | Ala | Val | Ala | Gly | Ala | Glu | Gly | Ser | Tyr | Phe | Trp | Asp | Tyr | Asp |
| | | | 35 | | | | 40 | | | | | 45 | | | |
| Gly | Arg | Arg | Tyr | Leu | Asp | Phe | Thr | Ser | Gly | Leu | Val | Phe | Thr | Asn | Ile |
| | 50 | | | | | 55 | | | | | 60 | | | | |
| Gly | Tyr | Gln | His | Pro | Lys | Val | Val | Ala | Ile | Gln | Glu | Gln | Ala | Ala | |
| 65 | | | | | 70 | | | | | 75 | | | | 80 | |
| Ser | Leu | Thr | Thr | Phe | Ala | Pro | Ala | Phe | Ala | Val | Glu | Ala | Arg | Ser | Glu |
| | | | | 85 | | | | | 90 | | | | | 95 | |
| Ala | Ala | Arg | Leu | Ile | Ala | Glu | Arg | Thr | Pro | Gly | Asp | Leu | Asn | Lys | Ile |
| | | | 100 | | | | | 105 | | | | | 110 | | |
| Leu | Phe | Thr | Asn | Gly | Gly | Ala | Asp | Ala | Ile | Glu | His | Ala | Val | Arg | Met |
| | | | 115 | | | | 120 | | | | | 125 | | | |
| Ala | Arg | Ile | His | Thr | Gly | Arg | Pro | Lys | Val | Leu | Ser | Ala | Tyr | Arg | Ser |
| | | 130 | | | | | 135 | | | | | 140 | | | |
| Tyr | His | Gly | Gly | Thr | Gln | Gln | Ala | Val | Asn | Ile | Thr | Gly | Asp | Pro | Arg |
| 145 | | | | | 150 | | | | | 155 | | | | | 160 |
| Arg | Trp | Ala | Ser | Asp | Ser | Ala | Ser | Ala | Gly | Val | Val | His | Phe | Trp | Ala |
| | | | | 165 | | | | | 170 | | | | | 175 | |
| Pro | Tyr | Leu | Tyr | Arg | Ser | Arg | Phe | Tyr | Ala | Glu | Thr | Glu | Gln | Gln | Glu |
| | | | 180 | | | | | 185 | | | | | 190 | | |
| Cys | Glu | Arg | Ala | Leu | Glu | His | Leu | Glu | Thr | Thr | Ile | Ala | Phe | Glu | Gly |
| | | | | 195 | | | | | 200 | | | | | 205 | |
| Pro | Gly | Thr | Ile | Ala | Ala | Ile | Val | Leu | Glu | Thr | Val | Pro | Gly | Thr | Ala |
| | | 210 | | | | | 215 | | | | | 220 | | | |
| Gly | Ile | Met | Val | Pro | Pro | Gly | Tyr | Leu | Ala | Gly | Val | Arg | Glu | Leu |
| 225 | | | | | 230 | | | | | 235 | | | | | 240 |
| Cys | Asp | Lys | Tyr | Gly | Ile | Val | Phe | Val | Leu | Asp | Glu | Val | Met | Ala | Gly |
| | | | | 245 | | | | | 250 | | | | | 255 | |
| Phe | Gly | Arg | Thr | Gly | Glu | Trp | Phe | Ala | Ala | Asp | Leu | Phe | Asp | Val | Thr |
| | | | 260 | | | | | 265 | | | | | 270 | | |
| Pro | Asp | Leu | Met | Thr | Phe | Ala | Lys | Gly | Val | Asn | Ser | Gly | Tyr | Val | Pro |
| | | | 275 | | | | | 280 | | | | | 285 | | |
| Leu | Gly | Gly | Val | Ala | Ile | Ser | Gly | Lys | Ile | Ala | Glu | Thr | Phe | Gly | Lys |
| | | 290 | | | | | 295 | | | | | 300 | | | |
| Arg | Ala | Tyr | Pro | Gly | Gly | Leu | Thr | Tyr | Ser | Gly | His | Pro | Leu | Ala | Cys |
| 305 | | | | | 310 | | | | | 315 | | | | | 320 |
| Ala | Ala | Ala | Val | Ala | Thr | Ile | Asn | Val | Met | Ala | Glu | Glu | Gly | Val | Val |
| | | | | 325 | | | | | 330 | | | | | 335 | |
| Glu | Asn | Ala | Ala | Asn | Leu | Gly | Ala | Arg | Val | Ile | Glu | Pro | Gly | Leu | Arg |
| | | | 340 | | | | | 345 | | | | | 350 | | |
| Glu | Leu | Ala | Glu | Arg | His | Pro | Ser | Val | Gly | Glu | Val | Arg | Gly | Val | Gly |
| | | | | 355 | | | | | 360 | | | | | 365 | |
| Met | Phe | Trp | Ala | Leu | Glu | Leu | Val | Lys | Asp | Arg | Glu | Thr | Arg | Glu | Pro |
| | | 370 | | | | | 375 | | | | | 380 | | | |
| Leu | Val | Pro | Tyr | Asn | Ala | Ala | Gly | Glu | Ala | Asn | Ala | Pro | Met | Ala | Ala |
| 385 | | | | | 390 | | | | | 395 | | | | | 400 |

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
        435                 440                 445

Tyr Thr Val
    450

<210> SEQ ID NO 20
<211> LENGTH: 897
<212> TYPE: DNA
<213> ORGANISM: Pseudomonas aeruginosa

<400> SEQUENCE: 20

```
atgaccgaca tcgcattcct cggcctgggc aacatgggtg gcccgatggc cgccaacctg     60
ctcaaggccg gccaccgggt gaatgtcttc gacttgcagc ccaaggccgt gctgggcctg    120
gtcgagcagg gcgcgcaggg cgccgatagc gccttgcagt gctgcgaagg cgccgaagtg    180
gtgatcagca tgctgccggc cgggcagcac gtggaaagcc tgtatctcgg cgacgacggc    240
ctgctcgcgc gggtcgccgg caagcccctg ctgatcgact gctcgaccat cgccccggag    300
accgcgcgca aggtcgccga ggccgccgcg gcgaagggcc tgaccctgct cgacgcgccg    360
gtttccggcg cgtcggcgg cgcccgcgcc ggcaccctga cttcatcgt cggcggcccc    420
gccgaaggct cgcgcgggc ccggccggtc tcgagaaca tgggccggaa catcttccac    480
gccggcgatc acggcgccgg ccaggtggcg aagatctgca acaacatgct cctcggcatc    540
ctcatggccg gcaccgccga ggccctggcg ctggggtga agaacggcct cgacccggcg    600
gtgctgtccg aggtgatgaa gcagagttcc ggcggcaact gggcgctgaa cctctacaac    660
ccctggcccg gggtgatgcc gcaggcgccg gcgagcaacg gctatgccgg cggtttccag    720
gtgcgcctga tgaacaagga cctcggcctg gcgctggcca acgcccaggc ggtgcaggcc    780
tcgacgccgc tcggcgcgct ggcgcgcaac ctgttcagcc tgcacgccca ggccgatgcc    840
gagcacgagg ggctggactt ctccagcatc cagaagctct accgcggcaa ggactga      897
```

<210> SEQ ID NO 21
<211> LENGTH: 298
<212> TYPE: PRT
<213> ORGANISM: Pseudomonas aeruginosa

<400> SEQUENCE: 21

Met Thr Asp Ile Ala Phe Leu Gly Leu Gly Asn Met Gly Gly Pro Met
1               5                   10                  15

Ala Ala Asn Leu Leu Lys Ala Gly His Arg Val Asn Val Phe Asp Leu
            20                  25                  30

Gln Pro Lys Ala Val Leu Gly Leu Val Glu Gln Gly Ala Gln Gly Ala
        35                  40                  45

Asp Ser Ala Leu Gln Cys Cys Glu Gly Ala Glu Val Val Ile Ser Met
    50                  55                  60

Leu Pro Ala Gly Gln His Val Glu Ser Leu Tyr Leu Gly Asp Asp Gly
65                  70                  75                  80

Leu Leu Ala Arg Val Ala Gly Lys Pro Leu Leu Ile Asp Cys Ser Thr
                85                  90                  95

Ile Ala Pro Glu Thr Ala Arg Lys Val Ala Glu Ala Ala Ala Ala Lys
            100                 105                 110

```
Gly Leu Thr Leu Leu Asp Ala Pro Val Ser Gly Val Gly Gly Ala
        115                 120                 125
Arg Ala Gly Thr Leu Ser Phe Ile Val Gly Gly Pro Ala Glu Gly Phe
    130                 135                 140
Ala Arg Ala Arg Pro Val Leu Glu Asn Met Gly Arg Asn Ile Phe His
145                 150                 155                 160
Ala Gly Asp His Gly Ala Gly Gln Val Ala Lys Ile Cys Asn Asn Met
                165                 170                 175
Leu Leu Gly Ile Leu Met Ala Gly Thr Ala Glu Ala Leu Ala Leu Gly
            180                 185                 190
Val Lys Asn Gly Leu Asp Pro Ala Val Leu Ser Glu Val Met Lys Gln
        195                 200                 205
Ser Ser Gly Gly Asn Trp Ala Leu Asn Leu Tyr Asn Pro Trp Pro Gly
    210                 215                 220
Val Met Pro Gln Ala Pro Ala Ser Asn Gly Tyr Ala Gly Gly Phe Gln
225                 230                 235                 240
Val Arg Leu Met Asn Lys Asp Leu Gly Leu Ala Leu Ala Asn Ala Gln
                245                 250                 255
Ala Val Gln Ala Ser Thr Pro Leu Gly Ala Leu Ala Arg Asn Leu Phe
            260                 265                 270
Ser Leu His Ala Gln Ala Asp Ala Glu His Glu Gly Leu Asp Phe Ser
        275                 280                 285
Ser Ile Gln Lys Leu Tyr Arg Gly Lys Asp
    290                 295

<210> SEQ ID NO 22
<211> LENGTH: 1387
<212> TYPE: DNA
<213> ORGANISM: Alcaligenes faecalis
<220> FEATURE:
<221> NAME/KEY: CDS
<222> LOCATION: (408)..(1304)

<400> SEQUENCE: 22
cattacacag gctctgcagc agtggcaggg cagtgccgac ccctggttgt cccgtgccgc      60
gcaaaccttc gccaaaggtg cgcctggttc ggctcgtttg tcctttgagc tgctggagag     120
ggtgcatcac ctgtctttgg ccgatgtttt ccgtctggaa tacattgtgt cgctgcaatg     180
tggcgtacag ggcgacttcc aggaaggcat acgggcactg ctgattgata agacaaaca     240 gccgcgctgg aatcctgcct cgctggaaca ggcggatgca cgctgggtgg aacgttttt      300 tgttcctgcc tggccggcag aaacgactca tcccttggct gacctgtaac ccaggcagac     360
cgctgcggcg ccagacggcg ccgctttcat aatgacgagg agacaaa atg agt aac       416
                                                      Met Ser Asn
                                                        1 acg att gca ttt atc ggg ctg ggc cat atg ggt aaa ccc atg gcg ctg       464
Thr Ile Ala Phe Ile Gly Leu Gly His Met Gly Lys Pro Met Ala Leu
  5                  10                  15 aat ctg ctc aaa gcc ggt cat agc ctg aac gtc ttt gac ttg aat gcg       512
Asn Leu Leu Lys Ala Gly His Ser Leu Asn Val Phe Asp Leu Asn Ala
 20                  25                  30                  35 caa gcc atg cag gaa ctg cag gca gca ggg gca cag gtg ggg gaa tcg       560
Gln Ala Met Gln Glu Leu Gln Ala Ala Gly Ala Gln Val Gly Glu Ser
                 40                  45                  50 gcg gtg caa atc gcc caa gac gcg cag atg gtc ttt acc atg ctg cct       608
Ala Val Gln Ile Ala Gln Asp Ala Gln Met Val Phe Thr Met Leu Pro
             55                  60                  65 gct ggc cgc cat gtt cgt cag gtt tac gag ggc gag aac ggc ttg ctg       656
```

```
cag act gtg gcc ccc ggt acg gtg ctg gtc gat tgc agc acc att gat      704
Gln Thr Val Ala Pro Gly Thr Val Leu Val Asp Cys Ser Thr Ile Asp
     85                  90                  95 gcg caa acc agc cag gat ctg gcg gcc aaa gcc agc aag ctg ggt ctg      752
Ala Gln Thr Ser Gln Asp Leu Ala Ala Lys Ala Ser Lys Leu Gly Leu
100                 105                 110                 115 ttc atg ctg gat gcg ccg gtc tcc ggt ggg acc ggt ggc gcc att gct      800
Phe Met Leu Asp Ala Pro Val Ser Gly Gly Thr Gly Gly Ala Ile Ala
                120                 125                 130 ggc acc ttg acc ttt atg gtc ggg ggc gag gat cag gcc ctg gaa aag      848
Gly Thr Leu Thr Phe Met Val Gly Gly Glu Asp Gln Ala Leu Glu Lys
            135                 140                 145 gcg cgc cct tac ttg gat gcc atg ggc aag aac att ttc cac gcg ggt      896
Ala Arg Pro Tyr Leu Asp Ala Met Gly Lys Asn Ile Phe His Ala Gly
        150                 155                 160 aaa gcc ggt gcg ggt cag gtt gcc aag att tgc aac aat atg ctc ttg      944
Lys Ala Gly Ala Gly Gln Val Ala Lys Ile Cys Asn Asn Met Leu Leu
165                 170                 175 ggg att ttg atg gcg ggt act gct gaa gcc ttg gct ttg ggc gtt gcc      992
Gly Ile Leu Met Ala Gly Thr Ala Glu Ala Leu Ala Leu Gly Val Ala
180                 185                 190                 195 cac ggt ctg gac cct gcc gtg ctg tcg acc atc atg gcg cgc agt tcc     1040
His Gly Leu Asp Pro Ala Val Leu Ser Thr Ile Met Ala Arg Ser Ser
                200                 205                 210 ggt cga aac tgg gca acc gag ctg tac aac ccc tgg cct ggg gtg atg     1088
Gly Arg Asn Trp Ala Thr Glu Leu Tyr Asn Pro Trp Pro Gly Val Met
            215                 220                 225 ccg gat gta ccg gct tcg cgt gat tat cag ggc ggt ttt gcg acg ggc     1136
Pro Asp Val Pro Ala Ser Arg Asp Tyr Gln Gly Gly Phe Ala Thr Gly
        230                 235                 240 ctg atg ctc aaa gac ctg ggt ctg gca gcc gat gcg gct gtc agc cag     1184
Leu Met Leu Lys Asp Leu Gly Leu Ala Ala Asp Ala Ala Val Ser Gln
245                 250                 255 aac agc gcg acg cct ttg ggc gaa ctg gca cgt aac ctg ttc gcc ttg     1232
Asn Ser Ala Thr Pro Leu Gly Glu Leu Ala Arg Asn Leu Phe Ala Leu
260                 265                 270                 275 cac gcc gca caa ggt cag aat gca ggg ctg gat ttc tcc agc att ctt     1280
His Ala Ala Gln Gly Gln Asn Ala Gly Leu Asp Phe Ser Ser Ile Leu
                280                 285                 290 aat ttg tac cgt cag aag cac taa gttctggcag tgcgtagggc aggggctgca    1334
Asn Leu Tyr Arg Gln Lys His
                295 gttccagcgc ctgtccttgc tccaattgaa actggccttg ttccaggtcc gcc          1387

<210> SEQ ID NO 23
<211> LENGTH: 298
<212> TYPE: PRT
<213> ORGANISM: Alcaligenes faecalis

<400> SEQUENCE: 23

Met Ser Asn Thr Ile Ala Phe Ile Gly Leu Gly His Met Gly Lys Pro
1               5                   10                  15

Met Ala Leu Asn Leu Leu Lys Ala Gly His Ser Leu Asn Val Phe Asp
                20                  25                  30

Leu Asn Ala Gln Ala Met Gln Glu Leu Gln Ala Ala Gly Ala Gln Val
            35                  40                  45

Gly Glu Ser Ala Val Gln Ile Ala Gln Asp Ala Gln Met Val Phe Thr
        50                  55                  60
```

Met Leu Pro Ala Gly Arg His Val Arg Gln Val Tyr Glu Gly Glu Asn
65                  70                  75                  80

Gly Leu Leu Gln Thr Val Ala Pro Gly Thr Val Leu Val Asp Cys Ser
            85                  90                  95

Thr Ile Asp Ala Gln Thr Ser Gln Asp Leu Ala Ala Lys Ala Ser Lys
        100                 105                 110

Leu Gly Leu Phe Met Leu Asp Ala Pro Val Ser Gly Thr Gly Gly
    115                 120                 125

Ala Ile Ala Gly Thr Leu Thr Phe Met Val Gly Gly Glu Asp Gln Ala
130                 135                 140

Leu Glu Lys Ala Arg Pro Tyr Leu Asp Ala Met Gly Lys Asn Ile Phe
145                 150                 155                 160

His Ala Gly Lys Ala Gly Ala Gly Gln Val Ala Lys Ile Cys Asn Asn
                165                 170                 175

Met Leu Leu Gly Ile Leu Met Ala Gly Thr Ala Glu Ala Leu Ala Leu
            180                 185                 190

Gly Val Ala His Gly Leu Asp Pro Ala Val Leu Ser Thr Ile Met Ala
        195                 200                 205

Arg Ser Ser Gly Arg Asn Trp Ala Thr Glu Leu Tyr Asn Pro Trp Pro
210                 215                 220

Gly Val Met Pro Asp Val Pro Ala Ser Arg Asp Tyr Gln Gly Gly Phe
225                 230                 235                 240

Ala Thr Gly Leu Met Leu Lys Asp Leu Gly Leu Ala Ala Asp Ala Ala
                245                 250                 255

Val Ser Gln Asn Ser Ala Thr Pro Leu Gly Glu Leu Ala Arg Asn Leu
            260                 265                 270

Phe Ala Leu His Ala Ala Gln Gly Gln Asn Ala Gly Leu Asp Phe Ser
        275                 280                 285

Ser Ile Leu Asn Leu Tyr Arg Gln Lys His
    290                 295

<210> SEQ ID NO 24
<211> LENGTH: 50
<212> TYPE: DNA
<213> ORGANISM: Artificial sequence
<220> FEATURE:
<223> OTHER INFORMATION: Synthetic oligonucleotide primer

<400> SEQUENCE: 24
tactgcggcc gcaagaagga gatatagata tgcgtattgc attcattggc            50

<210> SEQ ID NO 25
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 25
cctagtctag atcaatcctt cttgcgatac ccct                             34

<210> SEQ ID NO 26
<211> LENGTH: 888
<212> TYPE: DNA
<213> ORGANISM: Pseudomonas putida

<400> SEQUENCE: 26
atgcgtattg cattcattgg cctgggcaac atgggcgcgc ccatggcccg caacctgatc    60

-continued

```
aaggccgggc atcagctgaa cctgttcgac ctgaacaagg ccgtgctggc cgagctggca      120
gaactgggcg gcagatcag cccctcgccc aaggacgcgg cggccaacag cgagctggtg      180
atcaccatgc tgccggccgc agcccatgtg cgtagcgtgt acttgaacga ggacggcgta      240
ctggccggta ttcgtcctgg cacgccgacc gttgactgca gcaccatcga cccgcagacc      300
gcacgtgacg tgtccaaggc cgcagcggca aagggcgtgg acatggggga tgcgccggtt      360
tccggtggta ctggcggcgc ggcggccggc accctgacgt tcatggtcgg cgccagtacc      420
gagttgttcg ccagcctcaa gccggtactg gagcagatgg gccgcaacat cgtgcactgc      480
ggggaagtcg gtaccggcca gatcgccaag atctgcaaca acctgctgct cggcatttcg      540
atgatcggcg tgtccgaggc catggccctg gtaacgcgc tgggtatcga taccaaggtg      600
ctggccggca tcatcaacag ttcgaccggg cgttgctgga gctcggacac ctacaacccg      660
tggccgggca tcatcgaaac cgcacctgca tcgcgtggct acaccggtgg ctttggcgcc      720
gaactcatgc tcaaggacct ggggttggcc accgaagcgg cacgccaggc acaccaaccg      780
gtgattctcg gtgccgtggc ccagcagctg taccaggcca tgagcctgcg aggcgagggt      840
ggcaaggact ctctcggcat cgtagagggg tatcgcaaga aggattga                  888
```

<210> SEQ ID NO 27
<211> LENGTH: 295
<212> TYPE: PRT
<213> ORGANISM: Pseudomonas putida

<400> SEQUENCE: 27

```
Met Arg Ile Ala Phe Ile Gly Leu Gly Asn Met Gly Ala Pro Met Ala
1               5                   10                  15

Arg Asn Leu Ile Lys Ala Gly His Gln Leu Asn Leu Phe Asp Leu Asn
            20                  25                  30

Lys Ala Val Leu Ala Glu Leu Ala Glu Leu Gly Gly Gln Ile Ser Pro
        35                  40                  45

Ser Pro Lys Asp Ala Ala Ala Asn Ser Glu Leu Val Ile Thr Met Leu
    50                  55                  60

Pro Ala Ala His Val Arg Ser Val Tyr Leu Asn Glu Asp Gly Val
65                  70                  75                  80

Leu Ala Gly Ile Arg Pro Gly Thr Pro Thr Val Asp Cys Ser Thr Ile
                85                  90                  95

Asp Pro Gln Thr Ala Arg Asp Val Ser Lys Ala Ala Ala Lys Gly
            100                 105                 110

Val Asp Met Gly Asp Ala Pro Val Ser Gly Thr Gly Gly Ala Ala
        115                 120                 125

Ala Gly Thr Leu Thr Phe Met Val Gly Ala Ser Thr Glu Leu Phe Ala
    130                 135                 140

Ser Leu Lys Pro Val Leu Glu Gln Met Gly Arg Asn Ile Val His Cys
145                 150                 155                 160

Gly Glu Val Gly Thr Gly Gln Ile Ala Lys Ile Cys Asn Asn Leu Leu
                165                 170                 175

Leu Gly Ile Ser Met Ile Gly Val Ser Glu Ala Met Ala Leu Gly Asn
            180                 185                 190

Ala Leu Gly Ile Asp Thr Lys Val Leu Ala Gly Ile Ile Asn Ser Ser
        195                 200                 205

Thr Gly Arg Cys Trp Ser Ser Asp Thr Tyr Asn Pro Trp Pro Gly Ile
    210                 215                 220

Ile Glu Thr Ala Pro Ala Ser Arg Gly Tyr Thr Gly Gly Phe Gly Ala
225                 230                 235                 240
```

Glu Leu Met Leu Lys Asp Leu Gly Leu Ala Thr Glu Ala Ala Arg Gln
                245                 250                 255

Ala His Gln Pro Val Ile Leu Gly Ala Val Ala Gln Gln Leu Tyr Gln
                260                 265                 270

Ala Met Ser Leu Arg Gly Glu Gly Gly Lys Asp Phe Ser Ala Ile Val
            275                 280                 285

Glu Gly Tyr Arg Lys Lys Asp
        290                 295

<210> SEQ ID NO 28
<211> LENGTH: 53
<212> TYPE: DNA
<213> ORGANISM: Artificial sequence
<220> FEATURE:
<223> OTHER INFORMATION: Synthetic oligonucleotide primer

<400> SEQUENCE: 28
ggaggtattt atatgcgtat ygcwttyaty gghctgggca acatgggcgc gcc            53

<210> SEQ ID NO 29
<211> LENGTH: 888
<212> TYPE: DNA
<213> ORGANISM: Pseudomonas putida

<400> SEQUENCE: 29
atgcgtattg catttatcgg tctgggcaac atgggcgcgc ccatggcccg caacctgatc      60
aaggccgggc atcagctgaa cctgttcgac ctgaacaagg ccgtgctggc cgagctggca     120
gaactgggcg gcagatcag ccctcgccc aaggacgcgg cggccaacag cgagctggtg      180
atcaccatgc tgccggccgc agcccatgtg cgtagcgtgt acttgaacga ggacggcgta     240
ctggccggta ttcgtcctgg cacgccgacc gttgactgca gcaccatcga cccgcagacc     300
gcacgtgacg tgtccaaggc cgcagcggca aagggcgtgg acatggggga tgcgccggtt     360
tccggtggta ctggcggcgc ggcggccggc accctgacgt tcatggtcgg cgccagtacc     420
gagttgttcg ccagcctcaa gccggtactg gagcagatgg gccgcaacat cgtgcactgc     480
ggggaagtcg gtaccggcca gatcgccaag atctgcaaca acctgctgct cggcatttcg     540
atgatcggcg tgtccgaggc catggccctg gtaacgcgc tgggtatcga taccaaggtg      600
ctggccggca tcatcaacag ttcgaccggg cgttgctgga gctcggacac ctacaacccg     660
tggccgggca tcatcgaaac cgcacctgca tcgcgtggct acaccggtgg ctttggcgcc     720
gaactcatgc tcaaggacct ggggttggcc accgaagcgg cacgccaggc acaccaaccg     780
gtgattctcg gtgccgtggc ccagcagctg taccaggcca tgagcctgcg aggcgagggt     840
ggcaaggact ctctcggccat cgtagagggg tatcgcaaga aggattga                  888

<210> SEQ ID NO 30
<211> LENGTH: 747
<212> TYPE: DNA
<213> ORGANISM: Escherichia coli

<400> SEQUENCE: 30
atgatcgttt tagtaactgg agcaacggca ggttttggtg aatgcattac tcgtcgtttt      60
attcaacaag gcataaaagt tatcgccact ggccgtcgcc aggaacggtt gcaggagtta     120
aaagacgaac tgggagataa tctgtatatc gcccaactgg acgttcgcaa ccgcgccgct     180
attgaagaga tgctggcatc gcttcctgcc gagtggtgca atattgatat cctggtaaat     240
aatgccggcc tggcgttggg catggagcct gcgcataaag ccagcgttga agactgggaa     300

```
acgatgattg ataccaacaa caaaggcctg gtatatatga cgcgcgccgt cttaccgggt    360
atggttgaac gtaatcatgg tcatattatt aacattggct caacggcagg tagctggccg    420
tatgccggtg gtaacgttta cggtgcgacg aaagcgtttg ttcgtcagtt tagcctgaat    480
ctgcgtacgg atctgcatgg tacggcggtg cgcgtcaccg acatcgaacc gggtctggtg    540
ggtggtaccg agttttccaa tgtccgcttt aaaggcgatg acggtaaagc agaaaaaacc    600
tatcaaaata ccgttgcatt gacgccagaa gatgtcagcg aagccgtctg gtgggtgtca    660
acgctgcctg ctcacgtcaa tatcaatacc ctggaaatga tgccggttac ccaaagctat    720
gccggactga atgtccaccg tcagtaa                                        747
```

<210> SEQ ID NO 31
<211> LENGTH: 248
<212> TYPE: PRT
<213> ORGANISM: Escherichia coli

<400> SEQUENCE: 31

```
Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Gly Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245
```

<210> SEQ ID NO 32
<211> LENGTH: 35
<212> TYPE: DNA
<213> ORGANISM: Artificial sequence
<220> FEATURE:
<223> OTHER INFORMATION: Synthetic oligonucleotide primer

```
<400> SEQUENCE: 32
ggtagacata tgatcgtttt agtaactgga gcaac                                35

<210> SEQ ID NO 33
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 33
gttctcggat ccttactgac ggtggacatt cagtc                                35

<210> SEQ ID NO 34
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 34
ggaattccat atgcatttaa atatgttaaa atc                                  33

<210> SEQ ID NO 35
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 35
cccaagcttt agccaattgt cccgtgcttt tc                                   32

<210> SEQ ID NO 36
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 36
ggaattccat atgctgcgta ccatgttcaa gtc                                  33

<210> SEQ ID NO 37
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 37
acacaagctt taggcggtga cggcctgc                                        28

<210> SEQ ID NO 38
<211> LENGTH: 384
<212> TYPE: DNA
<213> ORGANISM: Clostridium acetobutylicum

<400> SEQUENCE: 38
atgcatttaa atatgttaaa atctaaaatt catagagcaa cagttgttca agctgattta     60
aattatgttg gaagcataac tattgataga aaccttatgg ataaagccaa tatacttgaa    120
tacgaaaagg tagagatagc aaatataaat aatggtgcta gatttgaaac ctacgtaata    180
gctggagaag ctggaagtgg aataatatgc cttaatggag ccgctgcaag atgtgcccaa    240
```

```
gctggcgata aagtaataat tatgtgctat tgcagcttaa cacctgaaga agcatcagaa    300
catagaccaa aagtcgtatt tgtaaatgat gacaatagta tatctaatgt tacagagtac    360
gaaaagcacg ggacaattgg ctaa                                          384
```

<210> SEQ ID NO 39
<211> LENGTH: 127
<212> TYPE: PRT
<213> ORGANISM: Clostridium acetobutylicum

<400> SEQUENCE: 39

```
Met His Leu Asn Met Leu Lys Ser Lys Ile His Arg Ala Thr Val Val
1               5                   10                  15

Gln Ala Asp Leu Asn Tyr Val Gly Ser Ile Thr Ile Asp Arg Asn Leu
            20                  25                  30

Met Asp Lys Ala Asn Ile Leu Glu Tyr Glu Lys Val Glu Ile Ala Asn
        35                  40                  45

Ile Asn Asn Gly Ala Arg Phe Glu Thr Tyr Val Ile Ala Gly Glu Ala
    50                  55                  60

Gly Ser Gly Ile Ile Cys Leu Asn Gly Ala Ala Arg Cys Ala Gln
65                  70                  75                  80

Ala Gly Asp Lys Val Ile Ile Met Cys Tyr Cys Ser Leu Thr Pro Glu
                85                  90                  95

Glu Ala Ser Glu His Arg Pro Lys Val Val Phe Val Asn Asp Asp Asn
            100                 105                 110

Ser Ile Ser Asn Val Thr Glu Tyr Glu Lys His Gly Thr Ile Gly
        115                 120                 125
```

<210> SEQ ID NO 40
<211> LENGTH: 420
<212> TYPE: DNA
<213> ORGANISM: Streptomyces avermitilis

<400> SEQUENCE: 40

```
atgctgcgta ccatgttcaa gtccaagatc caccgagcca ccgtcaccca ggccgacctg    60
cactacgtcg atccgtcac catcgacgcc gatcttctgg acgccgccga tctgctgccc    120
ggcgagttgg ttcatatcgt cgacatcacc aacggtgccc gcctggagac gtacgtcatc    180
gagggcgagc gtggctccgg agtcgtcggg atcaacgggg cggcggccca tctcgtccac    240
cccggcgacc tggtgatcat catcagctac gctcaggttt ccgacgccga ggcgagggca    300
ctgcggccga gggtcgtgca cgtggaccgc gacaaccgcg tcgtggccct gggcgcggac    360
ccggccgagc cggtaccggg ctcggaccag gcgcgcagcc gcaggccgt caccgcctga    420
```

<210> SEQ ID NO 41
<211> LENGTH: 139
<212> TYPE: PRT
<213> ORGANISM: Streptomyces avermitilis

<400> SEQUENCE: 41

```
Met Leu Arg Thr Met Phe Lys Ser Lys Ile His Arg Ala Thr Val Thr
1               5                   10                  15

Gln Ala Asp Leu His Tyr Val Gly Ser Val Thr Ile Asp Ala Asp Leu
            20                  25                  30

Leu Asp Ala Ala Asp Leu Leu Pro Gly Glu Leu Val His Ile Val Asp
        35                  40                  45

Ile Thr Asn Gly Ala Arg Leu Glu Thr Tyr Val Ile Glu Gly Glu Arg
    50                  55                  60
```

Gly Ser Gly Val Val Gly Ile Asn Gly Ala Ala Ala His Leu Val His
65                  70                  75                  80

Pro Gly Asp Leu Val Ile Ile Ser Tyr Ala Gln Val Ser Asp Ala
            85                  90                  95

Glu Ala Arg Ala Leu Arg Pro Arg Val Val His Val Asp Arg Asp Asn
            100                 105                 110

Arg Val Val Ala Leu Gly Ala Asp Pro Ala Glu Pro Val Pro Gly Ser
        115                 120                 125

Asp Gln Ala Arg Ser Pro Gln Ala Val Thr Ala
    130                 135

<210> SEQ ID NO 42
<211> LENGTH: 69
<212> TYPE: DNA
<213> ORGANISM: Artificial sequence
<220> FEATURE:
<223> OTHER INFORMATION: Synthetic oligonucleotide primer

<400> SEQUENCE: 42
taaacttgtt accgttatca cattcaggag atggagaacc atgaaacaag tgtaggctgg    60
agctgcttc                                                           69

<210> SEQ ID NO 43
<211> LENGTH: 69
<212> TYPE: DNA
<213> ORGANISM: Artificial sequence
<220> FEATURE:
<223> OTHER INFORMATION: Synthetic oligonucleotide primer

<400> SEQUENCE: 43
tcatggcatg tccttattat gacgggaaat gccacccttt ttaccttagc atatgaatat    60
cctccttag                                                           69

<210> SEQ ID NO 44
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 44
gggatttggt tctcgcataa tc                                            22

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 45
gtagggtcgt ctccgtaaac                                               20

<210> SEQ ID NO 46
<211> LENGTH: 65
<212> TYPE: DNA
<213> ORGANISM: Artificial sequence
<220> FEATURE:
<223> OTHER INFORMATION: Synthetic oligonucleotide primer

<400> SEQUENCE: 46
aggatacagg gctatcaaac gataagatgg ggtgtctggg gtaatgtgta ggctggagct    60

-continued

```
gcttc                                                              65

<210> SEQ ID NO 47
<211> LENGTH: 66
<212> TYPE: DNA
<213> ORGANISM: Artificial sequence
<220> FEATURE:
<223> OTHER INFORMATION: Synthetic oligonucleotide primer

<400> SEQUENCE: 47
gagcatactg acattactac gcaatgcgga atattgttcg ttcatatgta cctttctcct    60
cttaa                                                              66

<210> SEQ ID NO 48
<211> LENGTH: 65
<212> TYPE: DNA
<213> ORGANISM: Artificial sequence
<220> FEATURE:
<223> OTHER INFORMATION: Synthetic oligonucleotide primer

<400> SEQUENCE: 48
ccctgatagc ggacttccct tctgtaacca taatggaacc tcgtcgtgta ggctggagct    60
gcttc                                                              65

<210> SEQ ID NO 49
<211> LENGTH: 66
<212> TYPE: DNA
<213> ORGANISM: Artificial sequence
<220> FEATURE:
<223> OTHER INFORMATION: Synthetic oligonucleotide primer

<400> SEQUENCE: 49
gcccagaatc gggtcggcag gagcggcggt aatgttctca acatatgta cctttctcct     60 cttaa                                                              66

<210> SEQ ID NO 50
<211> LENGTH: 69
<212> TYPE: DNA
<213> ORGANISM: Artificial sequence
<220> FEATURE:
<223> OTHER INFORMATION: Synthetic oligonucleotide primer

<400> SEQUENCE: 50
ctgtacccag gttttccct ctttcacaga gcggcgagcc aaataaaaag tgtaggctgg    60
agctgcttc                                                          69

<210> SEQ ID NO 51
<211> LENGTH: 70
<212> TYPE: DNA
<213> ORGANISM: Artificial sequence
<220> FEATURE:
<223> OTHER INFORMATION: Synthetic oligonucleotide primer

<400> SEQUENCE: 51
tcaacagctg tatccccgtt gagggtgagt tttgcttttg tatcagccac atgaatatcc    60
gccttagttc                                                         70

<210> SEQ ID NO 52
<211> LENGTH: 263
<212> TYPE: DNA
<213> ORGANISM: Artificial sequence
<220> FEATURE:
<223> OTHER INFORMATION: Nucleotide sequence of a modified gltA locus
```

-continued

```
<400> SEQUENCE: 52
cagagctctg tacccaggtt ttccctctt tcacagagcg gcgagccaaa taaaaagtgt    60
aggctggagc tgcttcgaag ttcctatact ttctagagaa taggaacttc ggaataggaa   120
ctaaagcgga tattcatgtg gctgatacaa aagcaaaact caccctcaac ggggatacag   180
ctgttgaact ggatgtgctg aaaggcacgc tgggtcaaga tgttattgat atccgtactc   240
tcggttcaaa aggtgtgttc acc                                            263

<210> SEQ ID NO 53
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 53
gattcgccat ttattcgtca tc                                             22

<210> SEQ ID NO 54
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 54
ctgggtcaaa ggtgaacac                                                 19

<210> SEQ ID NO 55
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 55
gttttgcttt tgtatcagcc aca                                            23

<210> SEQ ID NO 56
<211> LENGTH: 69
<212> TYPE: DNA
<213> ORGANISM: Artificial sequence
<220> FEATURE:
<223> OTHER INFORMATION: Synthetic oligonucleotide primer

<400> SEQUENCE: 56
gagcaatatc agaacgttaa ctaaatagag gcattgtgct gtgaatcttg tgtaggctgg    60
agctgcttc                                                            69

<210> SEQ ID NO 57
<211> LENGTH: 69
<212> TYPE: DNA
<213> ORGANISM: Artificial sequence
<220> FEATURE:
<223> OTHER INFORMATION: Synthetic oligonucleotide primer

<400> SEQUENCE: 57
cgctgatttc ggtggaattc agttgcatgc tccagtcccc ttaagactgc atatgaatat    60
cctccttag                                                            69

<210> SEQ ID NO 58
<211> LENGTH: 20
<212> TYPE: DNA
```

-continued

```
<213> ORGANISM: Artificial sequence
<220> FEATURE:
<223> OTHER INFORMATION: Synthetic oligonucleotide primer

<400> SEQUENCE: 58
ctctgctgcg tactcagttc                                              20

<210> SEQ ID NO 59
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 59
gatcatttca ccctgcatac aatc                                         24
```

BETA-ALANINE/ALPHA-KETOGLUTARATE AMINOTRANSFERASE FOR 3-HYDROXYPROPIONIC ACID PRODUCTION

CROSS-REFERENCE TO RELATED APPLICATIONS

This application claims the benefit of U.S. Provisional application No. 60/824,031 filed Aug. 30, 2006, herein incorporated by reference.

ACKNOWLEDGEMENT OF GOVERNMENT SUPPORT

This invention was made with United States Government support under contract GO 13144 awarded by the Department of Energy. The United States Government has certain rights in this invention.

FIELD

This disclosure relates to improved beta-alanine/alpha-ketoglutarate aminotransferase (BAAT) nucleic acid and amino acid sequences, cells having improved BAAT activity that can be used to convert beta-alanine to malonyl semialdehyde, which in turn can be converted to 3-hydroxypropionic acid (3-HP) by a 3-HP dehydrogenase, as well as methods of using the cells to produce 3-HP and derivatives thereof.

BACKGROUND

Organic chemicals such as organic acids, esters, and polyols can be used to synthesize plastic materials and other products. To meet the increasing demand for organic chemicals, more efficient and cost-effective production methods are being developed which utilize raw materials based on carbohydrates rather than hydrocarbons. For example, certain bacteria have been used to produce large quantities of lactic acid used in the production of polylactic acid.

3-hydroxypropionic acid (3-HP) is an organic acid. Several chemical synthesis routes have been described to produce 3-HP, and biocatalytic routes have also been disclosed (WO 01/16346 to Suthers et al.). 3-HP has utility for specialty synthesis and can be converted to commercially important intermediates by known art in the chemical industry, such as acrylic acid by dehydration, malonic acid by oxidation, esters by esterification reactions with alcohols, and 1,3-propanediol by reduction.

SUMMARY

The compound 3-hydroxypropionic acid (3-HP) can be produced biocatalytically from glucose, through a beta-alanine intermediate (FIG. 1). Beta-alanine can be converted to 3-HP via malonyl semialdehyde, using beta-alanine/alpha-ketoglutarate aminotransferase (BAAT) and a 3-HP dehydrogenase (FIG. 1). However, this pathway can be inefficient.

Disclosed herein are novel beta-alanine/alpha-ketoglutarate aminotransferase (BAAT) that have an enhanced ability to convert beta alanine to malonyl semialdehyde. This increase in the activity of the BAAT enzyme led to a corresponding increase in the production of malonyl semialdehyde and downstream products such as 3-HP.

Particular examples of isolated BAAT molecules include the nucleic acid sequences shown in SEQ ID NOS: 3, 5, 7, 9, 11, 13, 16 and 18, and their corresponding amino acid sequences shown in SEQ ID NOS: 4, 6, 8, 10, 12, 14, 17 and 19, as well as variants, fragments, fusions, and polymorphisms of these sequences that retain the ability to interconvert beta-alanine to malonyl semialdehyde. The disclosed nucleic acid molecules can be operably linked to a promoter, and can be part of a vector.

The disclosed BAAT sequences can be used to transform cells, such that the transformed cells have BAAT activity, which allows the cells to produce malonyl semialdehyde from beta-alanine. In some examples, such transformed cells produce 3-HP or derivatives thereof. Binding agents that specifically bind to any of SEQ ID NOS: 4, 6, 8, 10, 12, 14, 17 or 19 are encompassed by this disclosure. One example of such binding agents is an antibody, such as a polyclonal or monoclonal antibody.

Isolated cells are provided that express an exogenous BAAT nucleic acid molecule, and thus have BAAT activity allow the cell to convert beta-alanine to malonyl semialdehyde. Such cells can be eukaryotic or prokaryotic cells, such as yeast cells, plant cells, fungal cells, or bacterial cells (for example *Lactobacillus, Lactococcus, Bacillus*, or *Escherichia* cells). Also provided are transgenic plants and organisms that include such cells. In one example, the cell is transformed with a nucleic acid molecule encoding BAAT (such as any of SEQ ID NOS: 3, 5, 7, 9, 11, 13, 16 and 18 or fragments, fusions, or variants thereof that retain BAAT activity) that confers to the transformed cells BAAT activity. The disclosed cells can be used to produce nucleic acid molecules, peptides, and organic compounds, such as malonyl semialdehyde and 3-HP or derivatives thereof (such as polymerized 3-HP, 3-HP esters, or 1,3 propanediol). 3-HP is both biologically and commercially important. For example, the nutritional industry can use 3-HP as a food, feed additive or preservative, while the derivatives mentioned above can be produced from 3-HP. The cells described herein can be used in culture systems to produce large quantities of 3-HP as well as other organic compounds such as those listed above. The peptides can be used to catalyze the formation of organic compounds or can be used as antigens to create specific binding agents.

The disclosed cells, which in addition to BAAT activity, can in some examples include other enzyme activities, such as 3-HP dehydrogenase activity (such as a nucleic acid molecule encoding a protein having at least 95% sequence identity to SEQ ID NO: 21, 23, 27, or 31), wherein the cell produces 3-HP. Cells having BAAT and 3-HP dehydrogenase activity can further include other enzyme activities, for example to produce derivatives of 3-HP. In one example, such cells also have lipase or esterase activity and produce an ester of 3-HP. In another example, such cells also have esterase activity and produce polymerized 3-HP. In yet another example, such cells also have alcohol dehydrogenase activity (EC 1.1.1.1) and aldehyde dehydrogenase activity (such as an enzyme from the 1.2.1-class) activity and produce 1,3-propanediol. The additional enzyme activity can be endogenous to the cell or exogenous (for example supplied by an exogenous nucleic acid molecule encoding the enzyme).

In some examples the disclosed cells, which in addition to BAAT activity, include other enzyme activities, such as those needed to produce beta-alanine. Such activities can be endogenous to the cell, or can be supplied by one or more exogenous nucleic acid molecules. Examples of such enzymes include PEP carboxylase (for example when producing oxaloacetate from PEP), pyruvate carboxylase (for example when producing oxaloacetate from pyruvate), aspartate aminotransferase, and aspartate decarboxylase (such as a protein having at least 95% sequence identity to SEQ ID NO: 39 or 41). In particular examples, at least one exogenous nucleic acid molecules encoding such enzymes includes a non-native promoter to enhance expression of the enzyme, such as an increase of at least 20%.

In particular examples, the disclosed cells include mutations that increase the available pyruvate to make beta-alanine. Examples of such mutations include, but are not limited to: a ΔpoxB mutation (such as one that decreases acetate formation by the cell by at least 20%), an ΔadhE or ΔatpFH mutation (or both) (such as mutations result in the cell producing at least 20% more 3-HP as compared to the absence of ΔadhE or ΔatpFH), or the expression of an exogenous nucleic acid molecule comprising at least 95% sequence identity to SEQ ID NO: 52.

A method is disclosed for producing malonyl semialdehyde from beta-alanine using the disclosed cells having BAAT activity. In one example, the cell is transfected with one or more enzymes necessary to convert malonyl semialdehyde from beta-alanine. In another example, the method includes purifying beta-alanine from the cell, then contacting the beta-alanine with polypeptides necessary to convert malonyl semialdehyde from beta-alanine.

The present disclosure also provides methods of making 3-HP or derivates thereof. In one example, the disclosed cells are cultured under conditions that permit formation of 3-HP or a derivative thereof. In another example, an enzyme needed for the production of 3-HP, such as 3-HP dehydrogenase, is first purified from the disclosed cells, and then incubated under conditions with malonyl semialdehyde to allow the formation of 3-HP. In yet another example, 3-HP is purified from the disclosed cells, and then incubated with alcohol dehydrogenase and aldehyde dehydrogenase under conditions to allow the formation of 1,3-propanediol, or incubated with esterase under conditions to allow the formation of polymerized 3-HP, or incubated with lipase or esterase under conditions to allow the formation of a 3-HP ester.

In some examples, the disclosed products are produced in vitro (outside of a cell). In other examples, products are produced using a combination of in vitro and in vivo (within a cell) methods. In yet other examples, products are produced in vivo. For methods involving in vivo steps, the cells can be isolated cultured cells or whole organisms such as transgenic plants, or single-celled organisms such as yeast and bacteria (such as *Lactobacillus, Lactococcus, Bacillus,* and *Escherichia* cells). Products produced by these cells can be organic products such as beta-alanine, malonyl semialdehyde, 3-HP, and derivatives thereof such as organic acids, polyols (such as 1,3-propanediol), as well as a BAAT enzyme described herein.

The foregoing and other aspects of the disclosure will become more apparent from the following detailed description, which proceeds with reference to the accompanying figures.

BRIEF DESCRIPTION OF THE DRAWINGS

FIGS. 2A-B show an alignment of improved beta-alanine aminotransferases (BAATs) (SEQ ID NOS: 6, 10, 12, 14, 17, and 19) as compared to the native BAAT sequence (SEQ ID NO: 4). Residues in bold are changes made relative to the native BAAT sequence (SEQ ID NO: 4).

SEQUENCE LISTING

Figure 1:
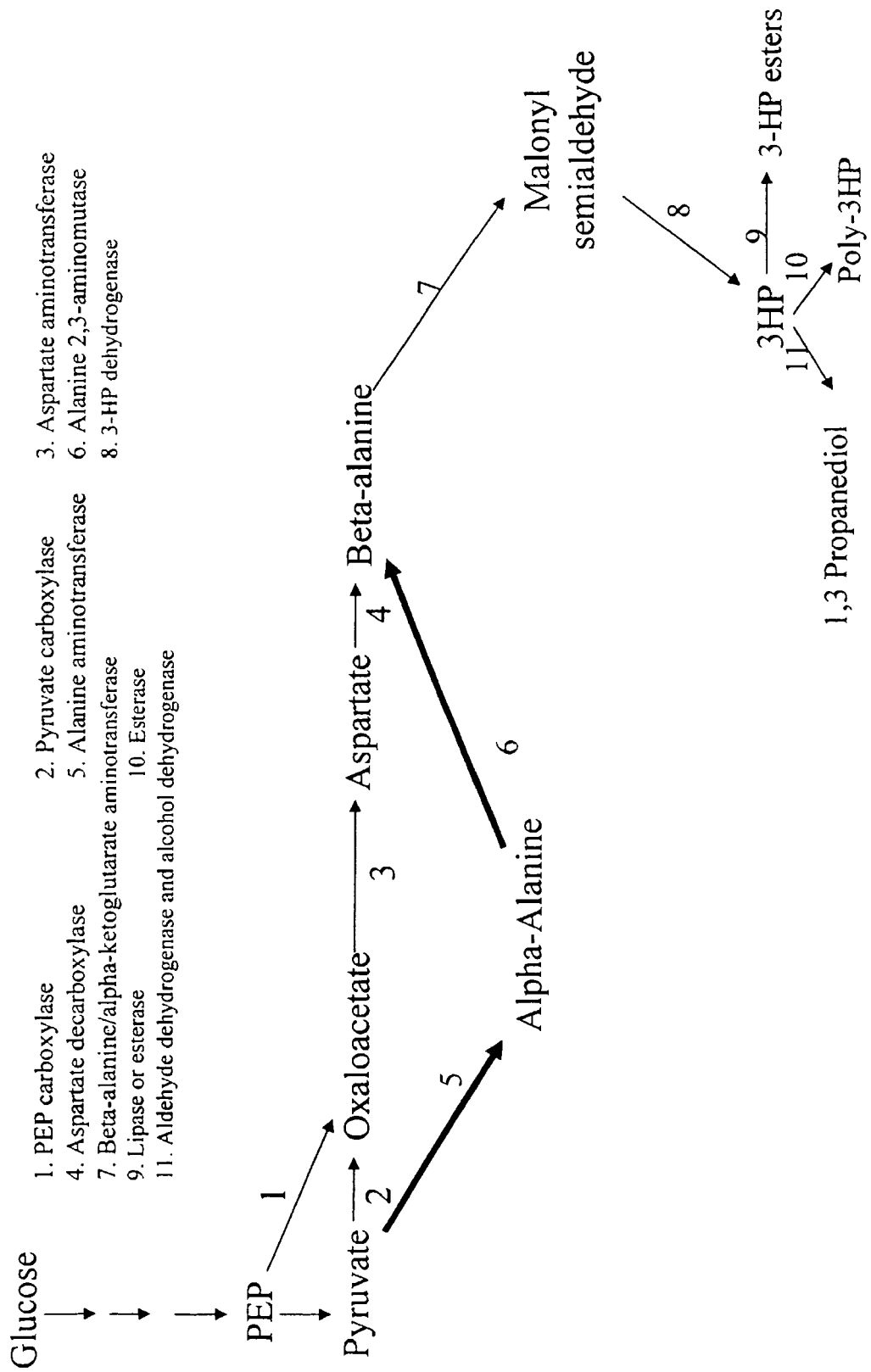
FIG. 1 is a diagram of a pathway for generating 3-HP and derivatives thereof via a beta-alanine intermediate.

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood as included by any reference to the displayed strand.

SEQ ID NOS: 1 and 2 are PCR primers used to PCR amplify an *S. avermitilis* BAAT gene.

SEQ ID NOS: 3 and 4 show a native *S. avermitilis* BAAT cDNA and protein sequence, respectively.

SEQ ID NOS: 5 and 6 show a mutated *S. avermitilis* BAAT cDNA and protein sequence, respectively, referred to herein as BAAT1. The protein includes a S24T mutation compared to the native sequence.

SEQ ID NOS: 7 and 8 show a mutated *S. avermitilis* BAAT cDNA and protein sequence, respectively, referred to herein as BAAT1b. The protein includes a T83A, S314T, and E348G mutation compared to the native sequence.

SEQ ID NOS: 9 and 10 show a mutated *S. avermitilis* BAAT cDNA and protein sequence, respectively, referred to herein as BAAT2. The protein includes a S24T and F113L mutation compared to the native sequence.

SEQ ID NOS: 11 and 12 show a mutated *S. avermitilis* BAAT cDNA and protein sequence, respectively, referred to herein as BAAT3. The protein includes a S24T, F113L and A133T mutation compared to the native sequence.

SEQ ID NOS: 13 and 14 show a mutated *S. avermitilis* BAAT cDNA and protein sequence, respectively, referred to herein as BAATP3H. The protein includes a P3H mutation compared to the native sequence.

SEQ ID NO: 15 shows the primer used to introduce the P3H mutation into BAAT2 and BAAT3 mutants.

SEQ ID NOS: 16 and 17 show a mutated *S. avermitilis* BAAT cDNA and protein sequence, respectively, referred to herein as BAAT3mL. The protein includes a P3H, S24T, F113L and A133T mutation compared to the native sequence.

SEQ ID NOS: 18 and 19 show a mutated *S. avermitilis* BAAT cDNA and protein sequence, respectively, referred to herein as BAAT5-9. The protein includes a P3H. S24T. D110N, F113L and A133T mutation compared to the native sequence. The nucleic acid sequence also includes silent mutations c207t, c381g, and t471c.

SEQ ID NOS: 20 and 21 show a *Pseudomonas aeruginosa* 3-HP dehydrogenase cDNA and protein sequence, respectively.

SEQ ID NOS: 22 and 23 show a *Alcaligenes faecalis* M3A 3-HP dehydrogenase cDNA and protein sequence, respectively.

SEQ ID NOS: 24 and 25 show amplification primers used to clone *P. putida* 3-HP dehydrogenase.

SEQ ID NOS: 26 and 27 show a *P. putida* 3-HP dehydrogenase cDNA and protein sequence, respectively.

SEQ ID NO: 28 shows the primer used to introduce mutations into the *P. putida* 3-HP dehydrogenase shown SEQ ID NO: 26.

SEQ ID NO: 29 is a mutated *P. putida* 3-HP dehydrogenase cDNA sequence, which does not change the amino acid sequence of SEQ ID NO: 27.

SEQ ID NO: 30 and 31 show an *E. coli* ydfG cDNA and protein sequence, respectively.

SEQ ID NOS: 32 and 33 are primers used to clone SEQ ID NO: 30 into the pET28b vector.

SEQ ID NOS: 34 and 35 are the forward and reverse primers, respectively, used to clone *C. acetobutylicum* aspartate decarboxylase.

SEQ ID NOS: 36 and 37 are the forward and reverse primers, respectively, used to clone *S. avermitilis* aspartate decarboxylase.

SEQ ID NOS: 38 and 39 show a *C. acetobutylicum* aspartate decarboxylase cDNA and protein sequence, respectively.

SEQ ID NOS: 40 and 41 show a *S. avermitilis* aspartate decarboxylase cDNA and protein sequence, respectively.

SEQ ID NOS: 42 and 43 are the forward and reverse primers, respectively, used to amplify the FRT-flanked kanamycin resistance marker from plasmid pKD4 for insertional deletion of the poxB gene in *Escherichia coli*.

SEQ ID NOS: 44 and 45 are the forward and reverse primers, respectively, used to confirm insertion of the FRT-flanked kanamycin resistance marker into the poxB gene.

SEQ ID NOS: 46 and 47 are the forward and reverse primers, respectively, used to amplify the FRT-flanked chloramphenicol resistance marker and $P_{lac/ara}$ promoter on pKDprom for insertion upstream of the ppc gene in *E. coli*.

SEQ ID NOS: 48 and 49 are the primers used to amplify the FRT-flanked chloramphenicol resistance marker and $P_{lac/ara}$ promoter on pKDprom for insertion upstream of the aspC gene in *E. coli*.

SEQ ID NOS: 50 and 51 are the forward and reverse primers, respectively, used to amplify the FRT-flanked chloramphenicol resistance marker on pKD3 for insertion upstream of the *E. coli* gltA gene to reduce expression of citrate synthase.

SEQ ID NO: 52 is the resulting nucleotide sequence of the modified gltA locus (KDgltA) in the resolved attenuated strain. Altered sequence nucleotides 57-138, translational start at bp 138.

SEQ ID NOS: 53-55 are primers used to test integration of the modified gltA locus.

SEQ ID NOS: 56 and 57 are the forward and reverse primers, respectively, used to amplify the FRT-flanked kanamycin resistance marker from plasmid pKD4 for insertional deletion of the atpFHgenes in *E. coli*.

SEQ ID NOS: 58 and 59 are the primers used to confirm the insertion of the FRT-flanked kanamycin resistance marker into the atpFH genes.

DETAILED DESCRIPTION

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and reference to "comprising the BAAT enzyme" includes reference to one or more BAAT enzymes and equivalents thereof known to those skilled in the art, and so forth. The term "or" refers to a single element of stated alternative elements or a combination of two or more elements, unless the context clearly indicates otherwise. For example, the phrase "alcohol dehydrogenase activity or aldehyde dehydrogenase activity" refers to alcohol dehydrogenase activity, aldehyde dehydrogenase, or a combination of both alcohol dehydrogenase activity and aldehyde dehydrogenase activity.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

3-HP: 3-hydroxypropionic acid

BAAT: beta-alanine/alpha-ketoglutarate aminotransferase adhE: The gene which encodes for alcohol dehydrogenase (EC 1.1.1.1). Also includes the protein alcohol dehydrogenase which catalyzes the reversible oxidation of primary or secondary alcohols to aldehydes using $NAD^+$ as an electron acceptor. adhE nucleic acid and protein sequences are publicly available. For example, GenBank Accession Nos: M33504, AF093749, AB008676, and CP000255 disclose adhE nucleic acid sequences and GenBank Accession Nos: AAA2342 AAC78120, BAA77747, and ABD21317 disclose adhE protein sequences.

atpFH: The genes (atpF and atpH) which encode the two proteins that couple the $F_1$ and $F_0$ components of the $F_0F_1$-ATP synthase. Also includes the proteins encoded by the genes. atpFH nucleic acid and protein sequences are publicly available. For example. GenBank Accession Nos: AB206839. AF522463, NC000913, AE009952, and CR931997 disclose atpFH nucleic acid sequences.

Antibody: A molecule including an antigen binding site which specifically binds (immunoreacts with) an antigen (such as a BAAT enzyme or fragment thereof). Examples include polyclonal antibodies, monoclonal antibodies, humanized monoclonal antibodies, or immunologically effective portions thereof. Includes immunoglobulin molecules and immunologically active portions thereof.

Monoclonal antibodies to any of the polypeptides disclosed herein can be prepared from murine hybridomas according to the classic method of Kohler & Milstein (*Nature* 256:495, 1975) or a derivative method thereof.

Polyclonal antiserum containing antibodies to the heterogeneous epitopes of any polypeptide disclosed herein can be prepared by immunizing suitable animals with the polypeptide (or fragment, fusion, or variant thereof), which can be unmodified or modified to enhance immunogenicity. An effective immunization protocol for rabbits can be found in Vaitukaitis et al. (*J. Clin. Endocrinol, Metab.* 33:988-91, 1971).

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (*Methods Enzymol.* 178:476-96, 1989), Glockshuber et al. (*Biochemistry* 29:1362-7, 1990). U.S. Pat. No. 5,648,237 ("Expression of Functional Antibody Fragments"). U.S. Pat. No. 4,946,778 ("Single Polypeptide Chain Binding Molecules"). U.S. Pat. No. 5,455,030 ("Immunotherapy Using Single Chain Polypeptide Binding Molecules"), and references cited therein.

Antibodies can be produced to a BAAT peptide (such as SEQ ID NO: 4, 6, 8, 10, 12, 14, 17 or 19 or immunogenic fragments thereof). Substantially pure polypeptides suitable for use as an immunogen can be obtained from transfected cells, transformed cells, or wild-type cells. Optimally, antibodies raised against one or more epitopes on a peptide antigen will specifically detect that peptide. That is, antibodies raised against one particular polypeptide would recognize and bind that particular polypeptide, and would not substantially recognize or bind to other polypeptides. The determination that an antibody specifically binds to a particular polypeptide is made by any one of a number of standard immunoassay methods; for instance, Western blotting "Specifically binds" refers to the ability of a particular agent (a "specific binding agent") to specifically react with a particular analyte, for example to specifically immunoreact with an antibody, or to specifically bind to a particular peptide sequence. The binding is a non-random binding reaction, for example between an antibody molecule and an antigenic determinant. Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody".

Beta-alanine/alpha-ketoglutarate aminotransferase (BAAT): An enzyme that can convert beta-alanine to malonyl semialdehyde, for example in a cell. Includes any BAAT gene, cDNA, RNA, or protein from any organism, such as a prokaryote. In particular examples, a BAAT nucleic acid sequence includes or consists of the sequences shown in SEQ ID NOS: 3, 5, 7, 9, 11, 13, 16, and 18, as well as fragments, variants, or fusions thereof that retain the ability to encode a protein having BAAT activity. In another example, a BAAT protein includes or consists of the amino acid sequence shown in SEQ ID NO: 4, 6, 8, 10, 12, 14, 17 or 19, as well as fragments, fusions, or variants thereof that retain BAAT activity. This description includes BAAT allelic variants, as well as any variant, fragment, or fusion sequence which retains the ability to convert beta-alanine to malonyl semialdehyde.

A BAAT amino acid sequence includes a full-length sequence, such as SEQ ID NO: 4, 6, 8, 10, 12, 14, 17 or 19, as well as shorter sequences or variants which retain the ability to convert beta-alanine to malonyl semialdehyde. Examples of particular substitutions that can be made to a BAAT amino sequence and retain the desired biological activity, include, but are not limited to, V53L, R104K, L200I, T312S, A400S, W411Y, or combinations thereof, in SEQ ID NO: 4, 6, 8, 10, 12, 14, 17 or 19. Exemplary fragments include amino acids 1-150, 1-140, 1-200, 1-250, 1-300, 1-350, or 1-400 of SEQ ID NO: 4, 6, 8, 10, 12, 14, 17 or 19.

BAAT activity: The ability of a BAAT enzyme to convert beta-alanine to malonyl semialdehyde. In one example, such activity occurs in a cell. In another example, such activity occurs in vitro. Such activity can be measured using any assay known in the art. For example, BAAT activity can be identified by incubating the enzyme with beta-alanine and alpha-ketoglutarate and determining the reaction products (such as malonyl semialdehyde and glutamate) by high-performance liquid chromatography (for example using the method of Abe et al. *J. Chromatography B,* 712:43-9, 1998). In a particular example, BAAT activity can be determined by measuring the production of malonyl semialdehyde from beta alanine in the presence of BAAT using a Purpald® assay (see Example 1). In a particular example, BAAT activity can be determined by measuring the production of 3-HP from beta alanine and malonyl semialdehyde intermediates in the presence of BAAT and 3-HP dehydrogenase using LC/MS (see Example 8).

In a particular example, an enzyme is said to have BAAT activity if the specific activity of an enzyme for beta-alanine is at least 0.3 U/mg (wherein U is 1 µmole/min) (for example using methods described in Example 4), such as at least 1.5 U/mg, at least 2 U/mg, at least 2.5 U/mg or at least 3 U/mg.

cDNA (complementary DNA): A piece of DNA lacking internal, non-coding segments (introns) and regulatory sequences which determine transcription. cDNA can be synthesized by reverse transcription from messenger RNA extracted from cells.

Conservative substitution: One or more amino acid substitutions (for example 1, 2, 5, 10, or 15 amino acid residues) for amino acid residues having similar biochemical properties. Typically, conservative substitutions have little to no impact on the activity of a resulting peptide. For example, a conservative substitution in a BAAT peptide that does not substantially affect the ability of the peptide to convert beta-alanine to malonyl semialdehyde. In a particular example, a conservative substitution is an amino acid substitution in a BAAT peptide, such as a conservative substitution in SEQ ID NO: 4, 6, 8, 10, 12, 14, 17, or 19, that does not significantly decrease (such as a decrease of no more than 20%, such as no more than 10%) the ability of the protein to convert beta-alanine to malonyl semialdehyde or other downstream products such as 3-HP.

An alanine scan can be used to identify amino acid residues in a peptide that can tolerate substitution. In one example, activity is not altered by more than 25%, for example not more than 20%, for example not more than 10%, when an alanine, or other conservative amino acid (such as those listed below), is substituted for one or more native amino acids.

In a particular example, BAAT activity is not substantially altered if the amount of malonyl semialdehyde produced is not reduced by more than about 25%, such as not more than about 10%, than an amount of malonyl semialdehyde production in the presence of a BAAT containing one or more conservative amino acid substitutions, as compared to an amount of malonyl semialdehyde production in the presence of a native BAAT (such as SEQ ID NO: 4).

A peptide can be produced to contain one or more conservative substitutions by manipulating the nucleotide sequence that encodes that peptide using, for example, standard procedures such as site-directed mutagenesis or PCR. Alternatively, a peptide can be produced to contain one or more conservative substitutions by using standard peptide synthesis methods.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; He or Val for Leu; Arg or Gln for Lys; Leu or Ile for Met; Met, Leu or Tyr for Phe; Thr for Ser; Ser for Thr; Tyr for Trp; Tip or Phe for Tyr; and Ile or Leu for Val.

Further information about conservative substitutions can be found in, among other locations in, Ben-Bassat et al., (*J. Bacterial.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

Deletion: The removal of one or more nucleotides from a nucleic acid molecule or one or more amino acids from a protein, the regions on either side being joined together.

Detectable: Capable of having an existence or presence ascertained. For example, production of malonyl semialdehyde from beta-alanine, or the production or 3-HP from beta-alanine, is detectable if the signal generated from malonyl semialdehyde or 3-HP, respectively, is strong enough to be measured.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a peptide. The term codon is also used for the corresponding (and complementary) sequences of three nucleotides in the mRNA into which the DNA sequence is transcribed.

Enhance or increase: To improve the quality, amount, or strength of something.

In one example, a mutant BAAT enzyme, such as a variant of SEQ ID NO: 4, can enhance, the activity of the BAAT enzyme if the activity of the enzyme is increased relative to the activity of the native BAAT enzyme (such as SEQ ID NO: 4). In a particular example, a mutant BAAT enzyme (such as SEQ ID NO: 5, 6, 8, 10, 12, 14, 17 or 19) has an increased ability to convert beta alanine to malonyl semialdehyde, such as an increase of at least 10%, at least 20%, at least 50%, at least 100%, or even at least 200%. For example, expression of an exogenous mutant BAAT enzyme (such as SEQ ID NO: 5, 6, 8, 10, 12, 14, 17 or 19) in a cell, can increase the production of downstream products such as malonyl semialdehyde, 3-HP, or derivatives thereof (if the other appropriate enzymes are expressed by the cell). Such enhancement can be measured using the methods disclosed herein, for example determining an amount of malonyl semialdehyde or 3-HP produced in the presence of the mutant BAAT enzyme using the methods disclosed in the examples below (such as Examples 1 and 8).

Exogenous: As used herein with reference to a nucleic acid molecule and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type.

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Functional Deletion: A mutation, partial or complete deletion, insertion, or other variation made to a gene sequence which reduces or inhibits production of the gene product, or renders the gene product non-functional. For example, functional deletion of poxB in *E. coli* reduces the production of acetate by pyruvate oxidase, which is encoded by the poxB gene. In another example, functional deletion of atpFH in *E. coli* reduces the production of ATP through proton translocation of the $F_0F_1$ complex.

Functionally Equivalent: Having a similar function, such as the ability of a sequence variant, fragment or fusion to have a similar function as the native sequence. In some examples, a functional equivalent has even greater biological activity than the native sequence. For example, functionally equivalent molecules of BAAT include those molecules that retain the function of BAAT, that is, the ability to convert beta-alanine to malonyl semialdehyde. For example, functional equivalents can be provided by sequence alterations in a BAAT, wherein the peptide with one or more sequence alterations (such as SEQ ID NOS: 6, 8, 10, 12, 14, 17, 19) retains a function of the unaltered peptide (such as SEQ ID NO: 4), such that it retains its ability to convert beta-alanine to malonyl semialdehyde.

Examples of sequence alterations include, but are not limited to, conservative substitutions, deletions, mutations, frameshifts, and insertions. In one example, a given peptide binds an antibody, and a functional equivalent is a peptide that binds the same antibody. Thus a functional equivalent includes peptides that have the same binding specificity as a peptide, and that can be used as a reagent in place of the peptide (such as in the production of malonyl semialdehyde, 3-HP, and derivatives thereof). In one example a functional equivalent includes a peptide wherein the binding sequence is discontinuous, wherein the antibody binds a linear epitope. Thus, if the peptide sequence is MTPQPNPQVG (amino acids 1-10 of SEQ ID NO: 4) a functional equivalent includes discontinuous epitopes, that can appear as follows (=any number of intervening amino acids): NH$_2$--MTPQPNPQV**G-COOH. In this example, the peptide is functionally equivalent to amino acids 1-10 of SEQ ID NO: 4 if the three dimensional structure of the peptide is such that it can bind a monoclonal antibody that binds amino acids 1-10 of SEQ ID NO: 4.

Hybridization: The ability of complementary single-stranded DNA or RNA to form a duplex molecule. In some examples, hybridization is used to determine the complementarity between two or more nucleotide sequences. Nucleic acid hybridization techniques can be used to obtain an isolated nucleic acid within the scope of the disclosure. Briefly, any nucleic acid molecule having some homology to a BAAT nucleic acid molecule (such as homology to SEQ ID NO: 3, 5, 7, 9, 11, 13, 16, or 18, or variants or fragments thereof) can be used as a probe to identify a similar nucleic acid molecule by hybridization under conditions of moderate to high stringency. Once identified, the nucleic acid then can be purified, sequenced, and analyzed to determine if it is a BAAT having BAAT activity.

Hybridization can be done by Southern or Northern analysis to identify a DNA or RNA sequence, respectively, that hybridizes to a probe. The probe can be labeled, for example with a biotin, a fluorophore, digoxygenin, an enzyme, or a radioisotope such as $^{32}$P. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y. Typically, a probe is at least about 20 nucleotides in length. For example, a probe including 20 contiguous nucleotides of a BAAT nucleic acid sequence (such as 20 contiguous nucleotides of SEQ ID NO: 3, 5, 7, 9, 11, 13, 16, or 18) can be used to identify an identical or similar nucleic acid. In addition, probes longer or shorter than 20 nucleotides can be used.

The disclosure also provides isolated nucleic acid sequences that are at least about 12 nucleotides in length (such as at least about 13, 14, 15, 16, 17, 18, 19, 20, 25, 30, 40, 50, 60, 100, 250, 500, 750, 1000, 1400, 2000, 3000, 4000, or 5000 nucleotides in length) and hybridize, under moderately or highly stringent hybridization conditions, to the sense or antisense strand of a BAAT nucleic acid sequence, for example SEQ ID NO: 3, 5, 7, 9, 11, 13, 16, or 18).

Moderately stringent hybridization conditions are when the hybridization is performed at about 42° C. in a hybridization solution containing 25 in M KPO$_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate.

Isolated: An "isolated" biological component (such as a nucleic acid molecule, protein, or cell) has been substantially separated or purified away from other biological components in which the component naturally occurs, such as other chromosomal and extrachromosomal DNA and RNA, and proteins. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

In one example, isolated refers to a naturally-occurring nucleic acid molecule that is not immediately contiguous with both of the sequences with which it is immediately contiguous (one on the 5' end and one on the 3' end) in the naturally-occurring genome of the organism from which it is derived. For example, an isolated nucleic acid molecule can be, without limitation, a recombinant DNA molecule of any length, provided one of the nucleic acid sequences normally found immediately flanking that recombinant DNA molecule in a naturally-occurring genome is removed or absent. Thus, an isolated nucleic acid molecule includes, without limitation, a recombinant DNA that exists as a separate molecule (for example, a cDNA or a genomic DNA fragment produced by PCR or restriction endonuclease treatment) independent of other sequences as well as recombinant DNA that is incorporated into a vector, an autonomously replicating plasmid, a virus (for example, a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

In one example, the term "isolated" as used with reference to a nucleic acid molecule also includes any non-naturally-occurring nucleic acid molecule since non-naturally-occurring nucleic acid sequences are not found in nature and do not have immediately contiguous sequences in a naturally-occurring genome. For example, non-naturally-occurring nucleic acid molecules such as an engineered nucleic acid molecule is considered to be an isolated nucleic acid molecule. Engineered nucleic acid molecules can be made using common molecular cloning or chemical nucleic acid synthesis techniques. Isolated non-naturally-occurring nucleic acid molecule can be independent of other sequences, or incorporated into a vector, an autonomously replicating plasmid, a virus (such as a retrovirus, adenovirus, or herpes virus), or the genomic DNA of a prokaryote or eukaryote. In addition, a non-naturally-occurring nucleic acid molecule can include a nucleic acid molecule that is part of a hybrid or fusion nucleic acid sequence.

Nucleic acid molecule: Encompasses both RNA and DNA including, without limitation, cDNA, genomic DNA, and mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecule can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence (such as a BAAT coding sequence) if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus placing genes in close proximity, for example in a plasmid vector, under the transcriptional regulation of a single promoter, constitutes a synthetic operon.

ORF (open reading frame): A series of nucleotide triplets (codons) coding for amino acids without any termination codons. These sequences are usually translatable into a peptide.

Peptide Modifications: The present disclosure provides novel peptides (such as novel BAAT, aspartate decarboxylases, and 3-HP dehydrogenases), as well as synthetic embodiments. In addition, analogues (non-peptide organic molecules), derivatives (chemically functionalized peptide molecules obtained starting with the disclosed peptide sequences) and variants (homologs) having alanine 2,3-aminomutase activity can be utilized in the methods described herein. The peptides disclosed herein include a sequence of amino acids that can be either L- or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide, side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this invention having detectable alanine 2,3-aminomutase activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters. "Computer-Assisted Modeling of Drugs", in Klegerman & Groves, eds., 1993, *Pharmaceutical Biotechnology*, Interpharm Press: Buffalo Grove, Ill. pp. 165-174 and *Principles of Pharmacology* Munson (ed.) 1995, Ch. 102, for descriptions of techniques used in CADD.

poxB: The gene which encodes for pyruvate oxidase. Also includes the protein pyruvate oxidase which metabolizes pyruvate to acetate and $CO_2$. poxB is primarily expressed in cultures under stress or in stationary phase under aerobic conditions. poxB nucleic acid and protein sequences are publicly available. For example, GenBank Accession Nos: AE009952, AX537387, M28208, and CR931997 disclose poxB nucleic acid sequences and GenBank Accession Nos: AAM86372, CAD57486, AAB59101, and CA136877 disclose poxB protein sequences.

Promoter: An array of nucleic acid control sequences that direct transcription of a nucleic acid molecule. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

The term includes endogenous promoter sequences as well as exogenous promoter sequences (such as those introduced into the chromosome to promote expression of a gene, such as BAAT). Particular types of promoters that can be used to practice the methods disclosed herein include, but are not limited to, constitutive promoters and inducible promoters (such as a promoter responsive or unresponsive to a particular stimulus, for example such as light, oxygen, or chemical concentration, such as a lactose, IPTG, arabinose, or tetracycline inducible promoter).

Purified: The term purified does not require absolute purity; rather, it is intended as a relative term. Thus, for example, a purified peptide preparation (such as a BAAT peptide preparation) is one in which the peptide in is more enriched than the peptide is in its environment within a cell, such that the peptide is substantially separated from cellular components (nucleic acids, lipids, carbohydrates, and other peptides) that may accompany it. In another example, a purified peptide preparation is one in which the peptide is substantially-free from contaminants, such as those that might be present following chemical synthesis of the peptide.

In one example, a peptide is purified when at least about 50% by weight of a sample is composed of the peptide, for example when at least about 60%, 70%, 80%, 85%, 90%, 92%, 95%, 98%, or 99% or more of a sample is composed of the peptide. Examples of methods that can be used to purify a peptide, include, but are not limited to the methods disclosed in Sambrook et al. (*Molecular Cloning: A Laboratory Manual*, Cold Spring Harbor, N.Y., 1989, Ch. 17). Protein purity can be determined by, for example, polyacrylamide gel electrophoresis of a protein sample, followed by visualization of a single peptide band upon staining the polyacrylamide gel; high-pressure liquid chromatography; sequencing; or other conventional methods.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994, Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: −i is set to a file containing the first nucleic acid sequence to be compared (such as C:\seq1.txt); −j is set to a file containing the second nucleic acid sequence to be compared (such as C:\seq2.txt); −p is set to blastn; −o is set to any desired file name (such as C:\output.txt); −q is set to −1; −r is set to 2; and all other options are left at their default setting. For example, the following command can be used to generate an output file containing a comparison between two sequences: C:\B12seq −i c:\seq1.txt −j c:\seq2.txt −p blastn −o c:\output.txt −q −1 −r 2.

To compare two amino acid sequences, the options of B12seq can be set as follows: −i is set to a file containing the first amino acid sequence to be compared (such as C:\seq 1.txt); −j is set to a file containing the second amino acid sequence to be compared (such as C:\seq2.txt); −p is set to blastp; −o is set to any desired file name (such as C:\output- .txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                    1                    20
Target Sequence:    ATGACCCATCAGCCGAATCC
                    | || ||| |||| |||| |
Identified Sequence: ACGAGCCAACAGCGGAATGC
```

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, at least 80%, at least 85%, at least 90%, at least 95%, at least 97%, or at least 99% sequence identity to any of SEQ ID NOS: 4, 6, 8, 10, 12, 14, 17, or 19.

When aligning short peptides (fewer than around 30 amino acids), the alignment should be performed using the Blast 2 sequences function, employing the PAM30 matrix set to default parameters (open gap 9. extension gap 1 penalties). Proteins with even greater similarity to the reference sequence will show increasing percentage identities when assessed by this method, such as at least 60%, 70%, 75%, 80%, 85%, 90%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to a BAAT gene sequence typically hybridize to a probe based on either an entire BAAT gene or selected portions of the gene, respectively, under conditions described above.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple, nucleic acid molecules that all encode, substantially the same protein. Such homologous nucleic acid sequences can, for example, possess at least 60%, at least 70%, at least 80%, at least 90%, at least 95%, at least 98%, or at least 99% sequence identity to any of SEQ ID NOS: 3, 5, 7, 9, 11, 13, 16 or 18 determined by this method.

One of skill in the art will appreciate that these sequence identity ranges are provided for guidance only; it is possible that strongly significant homologs could be obtained that fall outside the ranges provided.

An alternative (and not necessarily cumulative) indication that two nucleic acid sequences are substantially identical is that the peptide which the first nucleic acid encodes is immunologically cross reactive with the peptide encoded by the second nucleic acid.

Specific binding agent: An agent that binds substantially only to a defined target, such as a peptide target. For example, a BAAT binding agent includes anti-BAAT antibodies and other agents (such as a peptide or drug) that bind substantially to only a BAAT protein. Antibodies to a BAAT protein (or fragments thereof) can be used to purify or identify such a protein.

Transformed cell: A cell into which a nucleic acid molecule has been introduced, such as a BAAT nucleic acid molecule, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration.

Under conditions sufficient for: A phrase that is used to describe any environment that permits the desired activity.

In one example, includes culturing cells (such as bacterial cells) in growth medium and a temperature sufficient to allow the desired activity. In particular examples, the desired activity is the production of beta-alanine (or downstream product thereof, such as malonyl semialdehyde, 3-HP or derivatives thereof) by the cell.

Variants, fragments or fusions: The disclosed protein and nucleic acid sequences (such as BAAT, aspartate decarboxylase, and 3-HP dehydrogenase) include variants, fragments, and fusions thereof that retain the desired biological activity. For example, DNA sequences which encode for a BAAT protein (for example SEQ ID NO: 3, 5, 7, 9, 11, 13, 16, or 18), fusion BAAT protein, or a fragment or variant of a BAAT protein, can be engineered to allow the protein to be expressed in eukaryotic cells, bacteria, insects, or plants. To obtain expression, the DNA sequence can be altered and operably linked to other regulatory sequences. The final product, which contains the regulatory sequences and the protein, is referred to as a vector. This vector can be introduced into eukaryotic, bacteria, insect, or plant cells. Once inside the cell the vector allows the protein to be produced.

In one example, a fusion protein includes a BAAT amino acid sequence (or variant or fragment thereof), for example SEQ ID NO: 4, 6, 8, 10, 12, 14, 17 or 19, linked to other amino acid sequences that do not significantly decrease BAAT activity, for example the ability to convert beta-alanine to malonyl semialdehyde. In one example, the other amino acid sequences are no more than about 10, 12, 15, 20, 25, 30, or 50 amino acids in length, such as 5-50 amino acids. In addition, spacer sequences can be placed between the BAAT sequence and the additional amino acid sequence. Such spacers can be at least 4, at least 6, or at least 10 amino acids, such as 4-12 amino acids.

One of ordinary skill in the art will appreciate that a DNA sequence can be altered in numerous ways without affecting the biological activity of the encoded protein. For example, PCR can be used to produce variations in the DNA sequence which encodes a BAAT. Such variants can be variants optimized for codon preference in a host cell used to express the protein, or other sequence changes that facilitate expression.

Vector: A nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art.

Beta-Alanine/Alpha-Ketoglutarate Aminotransferase Sequences

The present disclosure provides novel beta-alanine/alpha-ketoglutarate aminotransferase (BAAT) protein and nucleic acid sequences that encode such proteins.

Proteins

Peptides having beta-alanine/alpha-ketoglutarate aminotransferase (BAAT) activity are disclosed herein. Using several rounds of mutagenesis followed by screening for malonyl semialdehyde production, several mutations in the BAAT amino acid sequence were identified that increased the biological activity of a native BAAT sequence (SEQ ID NO: 4). These substitutions included: P3H, S24T, D110N, F113L, and A133T, as well as combinations thereof (substitutions numbering based on SEQ ID NO: 4).

BAAT peptides have the ability to convert beta-alanine to malonyl semialdehyde, for example in a cell expressing exogenous BAAT. In particular examples, BAAT biological activity is determined by measuring the specific activity of the enzyme (for example by measuring the production of L-glutamate from beta-alanine and alpha-ketoglutarate, see Example 4). In another example. BAAT biological activity is determined by measuring the $K_m$ of the enzyme for beta-alanine (see Example 4). In specific examples, a BAAT enzyme having increased biological activity (such as a variant BAAT enzyme) is one that has a specific activity that is increased at least 2-fold relative to the native enzyme (such as SEQ ID NO: 4), such as an increase of at least 3-fold, at least 5-fold, or even at least 10-fold. In a particular example, a BAAT enzyme having increased biological activity (such as a variant BAAT enzyme) is one that has a specific activity of at least 1.5 U/mg (where U is 1 µmole/minute), such as a specific activity of at least 2 U/mg, or even a specific activity of at least 3 U/mg.

The disclosed BAAT peptides can be used to produce 3-HP, for example in combination with a 3-HP dehydrogenase (such as SEQ ID NO: 21, 23, 27, and 31) (see FIG. 1).

Particular examples of BAAT peptides are shown in SEQ ID NOS: 4, 6, 8, 10, 12, 14, 17, and 19. SEQ ID NO: 4 is a native BAAT sequence, while SEQ ID NOS: 6, 8, 10, 12, 14, 17, and 19 are variant sequences having increased BAAT biological activity.

The disclosure also encompasses variants, fusions, and fragments of SEQ ID NOS: 4, 6, 8, 10, 12, 14, 17, and 19 which retain BAAT biological activity, or even increased BAAT activity. Variant BAAT peptide sequences can be produced by manipulating the nucleotide sequence encoding a BAAT peptide using standard procedures such as site-directed mutagenesis or PCR. In particular examples, variants, fusions, and fragments of SEQ ID NOS: 4, 6, 8, 10, 12, 14, 17, and 19 have at least 90% of the BAAT activity as SEQ ID NO: 6, 8, 10, 12, 14, 17, or 19, such as at least 95%, at least 98%, at least 100%, or even at least 150% of the BAAT activity of SEQ ID NO: 6, 8, 10, 12, 14, 17, or 19.

In some examples, a BAAT peptide includes at least 80% sequence identity (such as at least 85%, at least 90%, at least 95%, at least 97%, at least 98%, or at least 99% sequence identity) to SEQ ID NO: 4, 6, 8, 10, 12, 14, 17, or 19, and includes a P3H, S24T, D110N, F113L, or A133T substitution, or combinations thereof, and retain BAAT activity. For example, such a sequence can include a P3H, S24T, D110N, F113L, or A133T substitution, both an S24T and a F113L substitution; a S24T, F113L, and A133T substitution: a P3H. S24T, F113L, and A133T substitution; or a S24T, F113L, and A133T substitution; a P3H, S24T, D110N, F113L, and A133T substitution. One skilled in the art will appreciate that other combinations are possible that will provide BAAT activity. Nucleic acid molecules encoding such proteins are also provided by this disclosure.

Variants include substitution of one or more amino acids, such as one or more conservative amino acid substitutions, one or more non-conservative amino acid substitutions, or combinations thereof. Variants also include deletion or insertion of one or more amino acids (or combinations thereof, such as a single deletion together with multiple insertions), such as addition or deletion of no more than 50 amino acids, no more than 20 amino acids, no more than 10 amino acids, no more than 5 amino acids, or no more than 2 amino acids, such as an addition or deletion of 1-5 amino acids, 1-10 amino acids, or 2-20 amino acids. In a particular example, a variant BAAT sequence includes at least 80% sequence identity to any of SEQ ID NOS: 4, 6, 8, 10, 12, 14, 17, and 19, such as at least 85%, at least 90%, at least 95%, at least 97%, at least 98% or at least 99% sequence identity to SEQ ID NOS: 4, 6, 8, 10, 12, 14, 17, or 19, as long as the peptide encoded by the amino acid sequence retains BAAT activity.

Non-conservative substitutions are those wherein the amino acids have more substantial difference, such as their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, such as serine or threonine, is substituted for (or by) a hydrophobic residue, such as leucine, isoleucine, phenylalanine, valine or alanine; (b) a cysteine or proline is substituted for (or by) any other residue; (c) a residue having an electropositive side chain, such as lysine, arginine, or histidine, is substituted for (or by) an electronegative residue, such as glutamic acid or aspartic acid; or (d) a residue having a bulky side chain, such as phenylalanine, is substituted for (or by) one not having a side chain, such as glycine. The effects of these amino acid substitutions (or other deletions or additions) can be assessed for peptides having BAAT activity by analyzing the ability of the peptide to catalyze the conversion of beta-alanine to malonyl semialdehyde using the assays disclosed herein. Ideally, non-conservative amino acid substitutions do not substantially decrease the biological activity of a BAAT, and can even increase the biological activity of BAAT (as demonstrated by SEQ ID NOS: 6, 8, 10, 12, 14, 17 and 19).

In contrast, conservative substitutions are those wherein the amino acids have similar biochemical properties. In one example, a BAAT sequence includes at least one conservative amino acid substitution in any of SEQ ID NOS: 4, 6, 8, 10, 12, 14, 17, or 19, such as at least 2, at least 3, at least 4, at least 5, at least 6, at least 8, at least 9, at least 10, at least 11, at least 12, at least 13, at least 14, at least 15, at least 16, at least 17, at least 18, at least 19, or at least 20 conservative amino acid substitutions, for example 1-5, 1-10, or 1-20 conservative amino acid substitutions. Particular examples of conservative substitutions which can be made while still retaining BAAT activity include, but are not limited to: A205S, L250V, Y52W, R50K, or S144T (amino acid number refers to any of SEQ ID NOS: 4, 6, 8, 10, 12, 14, 17, or 19).

Fragments of BAAT are provided, which can be expressed in the cells of the present disclosure, for example to produce 3-HP in vivo. The disclosure also provides BAAT peptides that contain at least 15 contiguous amino acids of SEQ ID NO: 4, 6, 8, 10, 12, 14, 17, or 19, which retain BAAT activity. BAAT peptides can also include at least 16, at least 17, at least 18, at least 19, at least 20, at least 25, at least 30, at least 50, at least 75, at least 100, at least 150, at least 200, at least 250, at least 300, at least 400, or at least 425 contiguous amino acid residues of SEQ ID NO: 4, 6, 8, 10, 12, 14, 17, or 19, as long as such fragments retain the ability to convert beta-alanine to malonyl semialdehyde.

Fusion proteins (and the corresponding nucleic acid sequences) can be generated using the disclosed BAAT sequences. Fusion sequences can include a full-length BAAT protein sequence (such as SEQ ID NO: 4, 6, 8, 10, 12, 14, 17, or 19), or a variant or fragment thereof that has BAAT activity, linked to a second amino acid sequence. In some examples, the second amino acid sequence includes at least 5 amino acids, such as at least 10 amino acids, at least 20 amino acids, at least 30 amino acids, at least 50 amino acids, at least 75 amino acids, at least 100 amino acids, at least 150 amino acids, or even at least 200 amino acids, for example 5-500 amino acids. In particular examples, the BAAT sequence and the second amino acid sequence are linked via a spacer sequence. Particular examples of spacers include on or more alanine or glycine residues, or other nonpolar amino acids or neutral polar amino acids. In some examples, spacers are no more than 50 amino acids, such as no more than 20 amino acids, no more than 10 amino acids, no more than 5 amino acids, for example 5-50 amino acids.

Nucleic Acid Molecules

Also disclosed are isolated nucleic acid molecules that encode peptides having BAAT activity, for example a sequence which includes SEQ ID NO: 3, 5, 7, 9, 11, 13, 16 or 18. However, the disclosure also encompasses variants, fusions, and fragments of SEQ ID NOS: 3, 5, 7, 9, 11, 13, 16 or 18 which retain the ability to encode a protein having BAAT activity, or even increased BAAT activity. In one example an isolated nucleic acid molecule encoding a peptide having BAAT activity is operably linked to a promoter sequence, and can be part of a vector. In particular examples, the promoter is one that enhances expresses of BAAT, such as a increase of at least 25%. The nucleic acid can be a recombinant nucleic acid that can be used to transform cells and make transformed cells or transgenic plants.

Transformed cells including at least one exogenous nucleic acid molecule which encodes a peptide having BAAT activity (such as SEQ ID NO: 3, 5, 7, 9, 11, 13, 16 or 18 or fragments, fusions, or variants thereof that retain BAAT activity), are disclosed. In one example, such a transformed cell produces malonyl semialdehyde from beta-alanine. In another example, the cell produces 3-HP (or derivates thereof such as 3-HP esters or polymerized 3-HP) or organic compounds such as 1,3-propanediol. Transformed cells can be eukaryotic or prokaryotic, such as bacterial cells, fungal cells, plant cells, or yeast cells. Specific examples of transgenic cells include *Lactobacillus, Lactococcus, Bacillus*, or *Escherichia* cells. Also provided are plants that include the disclosed BAAT nucleic acid molecules or transgenic cells expressing such BAAT nucleic acid molecules.

Nucleic acid sequences encoding a BAAT can contain an entire nucleic acid sequence encoding the enzyme, as well as portions thereof that retain the desired enzyme activity. For example, a BAAT nucleic acid molecule can contain at least 15 contiguous nucleotides of a BAAT nucleic acid sequence (such as SEQ ID NO: 3, 5, 7, 9, 11, 13, 16 or 18). It will be appreciated that the disclosure also provides isolated nucleic acid molecules that contain at least 18, at least 21, at least 27, at least 50, at least 100, at least 200, at least 500, at least 1000, or at least 1200 contiguous nucleotides of SEQ ID NO: 3, 5, 7, 9, 11, 13, 16 or 18. In some examples, fragments of SEQ ID NO: 3, 5, 7, 9, 11, 13, 16 or 18 (or the complementary strand) do not encode a protein having BAAT activity but are shorter fragments which can be used as probes or primers.

Variant BAAT nucleic acid sequences are disclosed herein. Variants can contain a single insertion, a single deletion, a single substitution, multiple insertions, multiple deletions, multiple substitutions, or any combination thereof (such as a single deletion together with multiple insertions) as long as the peptide encoded thereby retains BAAT activity (or can function as a probe or primer). Such isolated nucleic acid molecules can share at least 60%, at least 70%, at least 75%, at least 80%, at least 85%, at least 90%, at least 95%, at least 97%, at least 98%, or at least 99% sequence identity with a BAAT sequence (such as SEQ ID NO: 3, 5, 7, 9, 11, 13, 16 or 18), as long as the peptide encoded by the nucleic acid retains BAAT activity.

For example, one or more of the following variations can be made to SEQ ID NO: 3, 5, 7, 9, 11, 13, 16 or 18: the "g" at position 24 can be substituted with an "a"; the "c" at position 96 or 144 can be substituted with a "t"; the "c" at position 339 or 1110 can be substituted with a "t;" the "a" at position 816 can be substituted with a "c" "t" or "g"; the "c" at position 1200 or 1296 can be substituted with an "a" "t" or "g"; and the "g" at position 1152; can be substituted with an "a" "t" or "c"; the "g" at position 1344 can be substituted with an "a"; and the "t" at 1353 can be substituted with a "g" "a" or "c".

The coding region of a BAAT sequence can be altered by taking advantage of the degeneracy of the genetic code to alter the coding sequence in such a way that, while the nucleic acid sequence is substantially altered, it nevertheless encodes a peptide having an amino acid sequence identical or substantially similar to the native amino acid sequence. For example, codon preferences and codon usage tables for a particular species can be used to engineer isolated nucleic acid molecules that take advantage of the codon usage preferences of that particular species. Because of the degeneracy of the genetic code, alanine is encoded by the four nucleotide codon triplets: GCT, GCA, GCC, and GCG. Thus, the nucleic acid sequence of the open reading frame can be changed at an alanine position to any of these codons without affecting the amino acid sequence of the encoded polypeptide or the characteristics of the peptide. Based upon the degeneracy of the genetic code, nucleic acid variants can be derived from a nucleic acid sequence using standard DNA mutagenesis techniques as described herein, or by synthesis of nucleic acid sequences. Thus, this disclosure also encompasses nucleic acid molecules that encode the same polypeptide but vary in nucleic acid sequence by virtue of the degeneracy of the genetic code. Therefore, the BAAT sequences disclosed herein can be designed to have codons that are preferentially used by a particular organism of interest (for example as described in the Examples below).

Nucleic acids encoding variants, fusions, and fragments of a BAAT sequence (such as those disclosed above), are encompassed by this disclosure. The disclosure also provides isolated nucleic acid sequences that encode for a BAAT, wherein the sequence is at least 12 nucleotides in length (such as at least 15, at least 16, at least 17, at least 18, at least 19, at least 20, at least 25, at least 30, at least 40, at least 50, at least 60, at least 100, at least 250, at least 500, at least 750, at least 1000, or at least 1200 nucleotides in length) and hybridizes, under hybridization conditions, to the sense or antisense strand of a nucleic acid molecule encoding the enzyme. The hybridization conditions can be moderately or highly stringent hybridization conditions.

BAAT peptides and nucleic acid molecules encoding such peptides can be produced by standard DNA mutagenesis techniques, for example. M13 primer mutagenesis. Details of these techniques are provided in Sambrook et al. (ed.), Molecular Cloning: A Laboratory Manual 2nd ed., vol. 1-3, Cold Spring Harbor Laboratory Press, Cold Spring, Harbor, N.Y., 1989, Ch. 15, Nucleic acid molecules can contain changes of a coding region to fit the codon usage, bias of the particular organism into which the molecule is to be introduced.

Cells with BAAT Activity

Cells having BAAT activity, for example due to the presence of an exogenous BAAT nucleic acid or protein, are disclosed. Such cells can produce malonyl semialdehyde from beta-alanine, and in some examples also produce 3-HP (or derivatives thereof) from malonyl semialdehyde if 3-HP dehydrogenase activity is also present in the cell.

The enzyme activities expressed by the cells disclosed herein can be provided by expressing nucleic acid molecules that encode enzymes having the desired activity, or by supplying the enzyme directly. Methods of introducing exogenous nucleic acid sequences (such as those in a vector) into a cell are routine.

In one example, cells have BAAT activity due to expression of an exogenous BAAT nucleic acid molecule, such as a variant molecule that increases BAAT activity (for example as compared to a native BAAT sequence, such as SEQ ID NOS: 3 and 4). Examples of such variant molecules are provided herein (for example a nucleic acid sequence having at least 90% or at least 95% sequence identify to SEQ ID NO: 5, 7, 9, 11, 13, 16 or 18). In some examples, increased BAAT activity results in increased production of malonyl semialdehyde from beta-alanine by the cells, and may also result in increased production of 3-HP (or derivatives thereof) from malonyl semialdehyde if the cell also has 3-HP dehydrogenase activity. In particular examples, the production or yield of malonyl semialdehyde or a downstream product such as 3-HP (or derivatives thereof) is increased by at least 20%, such as at least 50%, at least 75%, at least 100%, or at least 150%. The increased production of malonyl semialdehyde or 3-HP can be relative to a cell of the same type that expresses a native BAAT sequence (whether exogenous or not, such as SEQ ID NOS: 3 and 4). Methods of measuring such production are known in the art and particular non-limiting examples are provided herein.

Cells including BAAT activity can be eukaryotic or prokaryotic. Examples of such cells include, but are not limited to bacterial cells (such as *Lactobacillus, Lactococcus, Bacillus, Escherichia, Geobacillus, Corynebacterium*, or *Clostridium*), fungal cells (such as *Aspergillus* or *Rhizopus* cells), plant cells (such as corn, wheat, rice, or soybean cells), and yeast cells. In one example, a cell is a microorganism. The term "microorganism" refers to any microscopic organism including, but not limited to, bacteria, algae, fungi, and protozoa. Thus. *E. coli, B. subtilis, B. licheniformis, S. cerevisiae, Kluveromyces lactis, Candida blankii, Candida rugosa,* and *Pichia pastoris* are microorganisms and can be used. In another example, the cell is part of a larger organism, such as a plant, such as a transgenic plant. Examples of plants that can be used to make 3-HP or other organic compounds from beta-alanine include, but are not limited to, genetically engineered plant crops such as corn, rice, wheat, and soybean.

In one example, cells having BAAT activity are transformed cells. Such cells can include at least one exogenous nucleic acid molecule that encodes a BAAT, for example a sequence that includes SEQ ID NO: 3, 5, 7, 9, 11, 13, 16 or 18 or variants, fragments, or fusions thereof that retain the ability to encode a protein having BAAT activity (see discussion of BAAT nucleic acid molecules above). In some examples, at least two different exogenous BAAT molecules are expressed, such as two or more of SEQ ID NOS: 3, 5, 7, 9, 11, 13, 16 and 18.

In one example, the exogenous nucleic acid molecule is a mutated BAAT, wherein the mutated BAAT (such as SEQ ID NOS: 5, 7, 9, 11, 13, 16 or 18) increases BAAT activity in the cell, and can increase the production of malonyl semialdehyde from beta-alanine. For example, the mutated BAAT can in some examples increase production of malonyl semialdehyde from beta-alanine in the cell by at least 3-fold relative to an amount of production of malonyl semialdehyde from beta-alanine in the presence of a native BAAT (such as SEQ ID NOS: 3 and 4), such as an increase of at least 4-fold, at least 5-fold, at least 6-fold, at least 8-fold, or even at least 10-fold.

Cells are disclosed which include BAAT activity as well as other enzyme activities. Such cells can be used to produce beta-alanine, malonyl semialdehyde, 3-HP, polyols such as 1,3-propanediol, polymerized 3-HP, co-polymers of 3-HP and esters of 3-HP. The other enzyme activities can be native to the cell, or can be exogenous due to the introduction of a nucleic acid molecule encoding the desired enzyme(s). In particular examples, operons that encode two or more desired enzymes, such as three of more desired enzymes, are introduced into the cell. For example, operons that include nucleic acid molecules encoding two or more of BAAT, 3-HP dehydrogenase, and aspartate decarboxylase can be expressed by the cell.

Cells are provided herein that have exogenous BAAT activity (for example due to expression of at least one of the BAAT molecules disclosed herein) as well as one or more endogenous or exogenous nucleic acid molecules that permit production of a downstream products of malonyl semialdehyde, such as 3-HP and derivates thereof. The presence of 3-HP can be determined using routine methods, such as described in Sullivan and Clarke (*J. Assoc. Offic. Agr. Chemists,* 38:514-8, 1955). For example, cells having BAAT and 3-HP dehydrogenase activity (3-hydroxypropionate dehydrogenase activity, EC 1.1.1.59) (for example due to expression of a nucleic acid sequence that encodes a protein having at least 95% sequence identity to SEQ ID NO: 21, 23, 27, or 31 such as SEQ ID NO: 20, 22, 26, 29, or 30). Such cells are capable of producing 3-HP from beta-alanine and malonyl semialdehyde intermediates. Similarly, cells having aspartate aminotransferase activity, aspartate decarboxylase activity (for example due to expression of a nucleic acid sequence that encodes a protein having at least 95% sequence identity to SEQ ID NO: 39 or 41, such as SEQ ID NO: 38 or 40), PEP carboxlase activity, exogenous BAAT activity (for example due to expression of at least one of the BAAT molecules disclosed herein), and 3-HP dehydrogenase activity (for example due to expression of SEQ ID NO: 20, 22, 26 or 29) are capable of producing 3-HP from glucose or pyruvate. In these examples, the cells can be used to produce 3-HP.

The cells described above that produce 3-HP can further contain lipase or esterase activity, for example due to expression of an exogenous nucleic acid molecule encoding a lipase or esterase (EC 3.1.1.-). Such cells can be used to produce an ester of 3-HP, such as methyl 3-hydroxypropionate, ethyl 3-hydroxypropionate, propyl 3-hydroxypropionate, butyl 3-hydroxypropionate, or 2-ethylhexyl 3-hydroxypropionate. The cells described above that produce 3-HP can further contain esterase activity, for example due to expression of an exogenous nucleic acid molecule encoding an esterase. Such cells can be used to produce polymerized 3-HP. The cells described above that produce 3-HP can further contain alcohol dehydrogenase activity (EC 1.1.1.1), aldehyde dehydrogenase activity (EC 1.2.1.-), or both, for example due to expression of an exogenous nucleic acid molecule encoding an alcohol dehydrogenase, aldehyde dehydrogenase, or both. Such cells can be used to produce 1,3 propanediol.

In particular examples, an exogenous nucleic acid molecule encoding the desired enzyme activity in the cell includes a non-native promoter that enhances expression of the desired enzyme. Such increased expression of desirable precursors can result in increased production of downstream products, such as beta-alanine, pyruvate, oxaloacetate, malonyl semialdehyde, as well as 3-HP and derivatives thereof. In particular examples, expression of one or more of these downstream products is increased by at least 20%, at least 50%, or even at least 100%, for example as compared to an amount of expression with a native promoter.

For example, promoters such as the lac promoter inducible with lactose or IPTG, the ara promoter inducible with arabinose, or the tet promoter inducible with tetracycline, or a constitutive promoter, can be substituted for an enzyme's native promoter using routine molecular biology methods. Such non-native or synthetic promoters are operably-linked to the coding sequence of the enzyme. In particular examples, such non-native promoters can increase expression of an enzyme by at least 20%, such as at least 50%, as compared to the enzyme's native promoter. Increased expression of the enzyme (at the nucleic acid or protein level) can be detected using routine methods such as Southern blotting, northern blotting, RT-PCR, polyacrylamide gel electrophoresis, western blotting or flow cytometry. In one example, the cells of the present disclosure that include exogenous BAAT activity also include one or more exogenous nucleic acid molecules encoding a PEP carboxylase, aspartate aminotransferase, aspartate decarboxylase, pyruvate carboxylase, BAAT, or 3-HP dehydrogenase (such as 2, 3, 4, 5, or 6 of these enzymes), wherein one or more of these enzymes are expressed from a non-native promoter.

The disclosed cells having exogenous BAAT activity (such as those that produce 3-HP) can also include mutations (such as a functional deletion of one or more genes) that increase the available pyruvate to serve as a precursor for downstream products such as beta-alanine and 3-HP. The increased availability of pyruvate can increase the production of desirable downstream products such as 3-HP and derivatives thereof, such as an increase of at least 20%, or at least 50%. For example, functional mutations in the poxB gene (ΔpoxB) reduce acetate formation by the cell (such as a reduction of at least 20%, or at least 50%), and can increase pyruvate in the cell. In another example, functional mutations in the adhE or ΔatpFH genes (ΔadhE or ΔatpFH) can increase pyruvate in the cell and thereby increased production of beta-alanine, malonyl semialdehyde, 3-HP (or combinations thereof), by at least 20%, or at least 50% (for example as compared to the presence of functional adhE or ΔatpFH genes). Methods of functionally deleting genes are routine in the art.

The disclosed cells having exogenous BAAT activity (such as those that produce 3-HP) can also include mutations in citrate synthase genes (such as a functional deletion of such genes) that significantly reduce the biological activity of the citrate, synthase. Such mutations can increase the amount of oxaloacetate available as substrate for the aspartate aminotransferase reaction (FIG. 1), thereby increasing the production of downstream products such as beta-alanine and 3-HP. The increased amount of oxaloacetate can increase the production of desirable downstream products such as 3-HP and derivatives thereof, such as an increase of at least 20%, or at least 50%. For example, expression of SEQ ID NO: 52 (a mutated gltA), can increase the production of 3-HP.

One skilled in the art will appreciate that the disclosed isolated cells can include multiple combination of desirable elements, such as non-native promoters operably linked to one or more of the desired enzymes (wherein the promoter increases expression of the enzyme relative to the native promoter), mutations that increase the available pyruvate, and mutations that decrease expression of citrate synthase.

In some examples, the desired product (such as beta-alanine, malonyl semialdehyde, and 3-HP or derivatives thereof) is secreted from the cell, reducing or eliminating the need to disrupt cell membranes to retrieve the desired compound. In one example, the cell produces the desired product(s) at a concentration of at least 1 mg per L (such as at least 1 mg/L, at least 5 mg/L, at least 10 mg/L, at least 50 mg/L, at least 100 mg/L, at least 200 mg/L, at least 500 mg/L, at least 1 g/L, at least 2 g/L, at least 5 g/L, or at least 10 g/L). When determining the yield of the product, such as 3-HP or derivatives thereof, for a particular cell, any method can be used. See, for example. *Applied Environmental Microbiology* 59(12):4261-5 (1993). A cell within the scope of the disclosure can utilize a variety of carbon sources. In another example, the radical SAM enzyme product (or downstream organic chemical thereof) is not secreted from the cell, in such examples, the cell membrane can be disrupted using methods known in the art to retrieve the organic compound.

Methods of Producing Malonyl Semialdehyde, 3-HP, and Derivatives Thereof

Methods and materials related to producing malonyl semialdehyde from beta-alanine, via the disclosed BAAT sequences and the disclosed cells having BAAT activity are disclosed. In addition, methods and materials related to producing 3-HP from malonyl semialdehyde, as well as organic compounds such as 1,3-propanediol, polymerized 3-HP, co-polymers of 3-HP and other compounds such as butyrates, valerates and other compounds, and esters of 3-HP, are disclosed. Specifically, the disclosure provides BAAT nucleic acid molecules (such as SEQ ID NO: 3, 5, 7, 9, 11, 13, 16, and 18), peptides (such as SEQ ID NO: 4, 6, 8, 10, 12, 14, 17 and 19), host cells, and methods and materials for producing malonyl semialdehyde from beta-alanine, which can be used to more efficiently make malonyl semialdehyde and 3-HP as well as derivatives thereof such as 1,3-propanediol, polymerized 3-HP, and esters of 3-HP. Although particular methods and enzymes are provided for producing beta-alanine and downstream chemicals, one skilled in the art will appreciate that similar methods and variant enzymes can be used.

Several metabolic pathways can be used to produce organic compounds from malonyl semialdehyde which has been produced from beta-alanine (FIG. 1). 3-HP can be made from beta-alanine by use of a peptide having BAAT activity which generates malonyl semialdehyde from beta-alanine. The malonyl semialdehyde can be converted into 3-HP with a peptide having 3-HP dehydrogenase activity (EC 1.1.1.59 or 0.31). The resulting 3-HP can be converted into polymerized 3-HP by a peptide having esterase activity. 3-HP can be converted into 1,3-propanediol by peptides having aldehyde dehydrogenase (EC 1.2.1.-) activity and alcohol dehydrogenase activity (EC 1.1.1.1). The resulting 3-HP can be converted into an ester of 3-HP by a polypeptide having lipase or esterase activity (EC 3.1.1.-).

The present disclosure also provides methods of increasing the production of beta-alanine, malonyl semialdehyde, 3-HP (and derivatives thereof). In particular examples, use of the variant BAAT sequences provided herein having increased BAAT activity, for example in combination with use of non-native promoters to express enzymes and increasing available pyruvate, production of beta-alanine, malonyl semialdehyde, and 3-HP can be increased, such as an increase of at least 20%, at least 40%, or even at least 50% or at least 100%. The increased production of the desired product can be relative to a cell of the same type that does not express an improved BAAT, does not express one or more enzymes from a non-native promoter, or does not include mutations that increase available pyruvate. For example, the increase can be relative to a reference value of product expected when a native BAAT is expresses (such as SEQ ID NO: 3). In another example, the increase can be relative to an experimental sample containing a native BAAT. Methods for measuring production of the desired product are known in the art, and particular non-limiting examples are disclosed herein.

The disclosed methods can be performed in vivo, in vitro, or combinations thereof. For example, a cell or microorganism provided herein can be used to perform one or more of the steps provided in FIG. 1, or an extract containing peptides having the indicated enzymatic activities can be used to perform one or more of the steps provided in FIG. 1. In one example, the method can include culturing the disclosed cells having BAAT and other desired enzyme activities under conditions sufficient for the cell to make the desired product (such as malonyl semialdehyde, 3-HP, or and derivatives thereof). For methods involving in vivo steps, the cells can be isolated cultured cells or whole organisms such as transgenic plants, or single-celled organisms such as yeast and bacteria (for example *Lactobacillus, Lactococcus, Bacillus,* and *Escherichia* cells). Such cells can be referred to as production cells. Products produced by these production cells can be organic products such as beta-alanine, malonyl semialdehyde, and 3-HP (or derivatives thereof).

In another example, in vitro methods (or a combination of in vivo and in vitro methods) are used. For example, malonyl semialdehyde can be produced by the cells having BAAT activity disclosed herein, purified, and then incubated with a 3-HP dehydrogenase in vitro under conditions that permit formation of 3-HP. One skilled in the art will appreciate that the in vitro synthesis step or steps can be via chemical reaction or enzymatic reaction. For example, chemical treatments can be used to perform the conversions provided in FIG. 1. In one example, 3-HP can be converted into a 3-HP ester by trans esterification, or into 1,3-propanediol by hydrogenation. Hydrogenating an organic acid such as 3-HP can be performed using any method such as those used to hydrogenate succinic acid or lactic acid. For example, 3-HP can be hydrogenated using a metal catalyst. In another example, 3-HP can be dehydrated to form acrylic acid. Any method can be used to perform a dehydration reaction. For example, 3-HP can be heated in the presence of a catalyst (such as a metal or mineral acid catalyst) to form acrylic acid.

Producing Malonyl Semialdehyde and 3-HP and Derivatives Thereof In Vivo

Methods and materials related to producing malonyl semialdehyde and downstream products such as 3-HP (and derivatives thereof) in vivo are provided. For example, malonyl semialdehyde and 3-HP can be produced in a cell, such as the cells provided herein. The cells can be isolated cultured cells or whole organisms such as transgenic plants, or single-celled organisms such as yeast and bacteria (for example *Lactobacillus, Lactococcus, Bacillus,* and *Escherichia* cells). In particular examples, the method includes culturing the cell under conditions sufficient for the desired product to be produced. For example, a cell can be transfected with one or more nucleic acid molecules that express the appropriate enzymes to generate the desired product, and then cultured under conditions sufficient to make the desired product. The desired product can be extracted from the cells, or can be recovered from the extracellular medium if the product is secreted by the cell. One skilled in the art will appreciate that the exogenous nucleic acid molecules encoding the appropriate enzymes can be part of one or more vectors, and can include other nucleic acid sequences.

Methods and materials related to producing malonyl semialdehyde front beta-alanine in vivo are provided. In one example, the method includes culturing disclosed cells having BAAT activity under conditions that permit the cell to make malonyl semialdehyde from beta-alanine. In particular examples, the BAAT activity is due to the presence of an exogenous nucleic acid molecule that encodes a BAAT enzyme (such as an enzyme having at least 95% sequence identity to SEQ ID NO: 6, 8, 10, 12, 14, 17 or 19). In some examples, the cell also includes an exogenous nucleic acid molecule encoding for other enzyme activities, such as those needed to produce beta-alanine from PEP, pyruvate, or both. Examples of such enzymes include, but are not limited to: PEP carboxylase, aspartate aminotransferase, and pyruvate carboxylase, aspartate decarboxylase. In one example, the cell includes an exogenous nucleic acid molecule that encodes an aspartate decarboxylase (such as an exogenous nucleic acid molecule encoding an aspartate decarboxylase having at least 95% sequence identity to SEQ ID NO: 38 or 40). The cell can also include mutations that increase available pyruvate. Examples of such mutations include, but are not limited to: a ΔpoxB mutation (such as those that decrease acetate formation by the cell by at least 20%), an ΔadhE or ΔatpFH mutation (for examples those that increase production of malonyl semialdehyde by at least 20% as compared to the absence of ΔadhE or ΔatpFH), or a mutation that decreases production of citrate synthase (such as expression of an exogenous nucleic acid molecule having at least 95% sequence identity to SEQ ID NO: 52).

Methods and materials related to producing 3-HP from malonate semialdehyde in vivo are disclosed. 3-HP can be used in the nutritional industry as a food, feed additive or preservative. In addition, 3-HP can be used to produce derivatives thereof, such as 1,3-propanediol, esters of 3-HP, acrylate or acrylic acid, polymerized acrylate, esters of acrylate, polymerized 3-HP, co-polymers of 3-HP and other compounds such as butyrates, valerate. In one example, the method includes culturing a disclosed cell having BAAT activity (for example those described above) and 3-HP dehydrogenase activity (EC 1.1.1.59) under conditions that permit the cell to make 3-HP from malonyl semialdehyde. In particular examples, the 3-HP dehydrogenase activity is due to the presence of an exogenous nucleic acid molecule that encodes a 3-HP dehydrogenase (such as an enzyme having at least 95% sequence identity to SEQ ID NO: 21, 23, 27, or 31).

Derivatives of 3-HP can be made in vivo from 3-HP generated from malonyl semialdehyde as described above. Derivatives of 3-HP, such as an ester of 3-HP, polymerized 3-HP, or 1,3 propanediol, can be generated from 3-HP in vivo by using cells that express the appropriate enzymes (see FIG. 1). In one example, these enzymes are supplied to the cell by transfecting the cell with one or more nucleic acid molecules that can express a protein having the necessary enzyme activity. For example, cells further having lipase or esterase activity (EC 3.1.1.-) can be used to convert 3-HP to an ester of 3-HP (such as methyl acrylate, ethyl acrylate, propyl acrylate, or butyl acrylate, for example methyl 3-hydroxypropionate, ethyl 3-hydroxypropionate, propyl 3-hydroxypropionate, butyl 3-hydroxypropionate, or 2-ethylhexyl 3-hydroxypropionate). Cells further having aldehyde dehydrogenase activity (EC 1.2.1.-) and alcohol dehydrogenase activity (EC 1.1.1.1) can be used to convert 3-HP to 1,3-propanediol. Cells further having esterase activity (EC 3.1.1.-) can be used to convert 3-HP to polymerized 3-HP.

Producing 3-HP and Derivatives Thereof Using In Vivo and In Vitro Methods

In particular examples, methods for producing a product such as 3-HP or derivatives thereof, are performed using a combination of in vivo and in vitro methods. For example, to generate 3-HP from malonyl semialdehyde, the malonyl semialdehyde can be generated in vivo in a cell (which in some examples is subsequently isolated or purified from the cell or culture medium), and the malonyl semialdehyde contacted with other enzymes or chemicals in vitro to generate the 3-HP or a derivative thereof. Although particular enzymes and methods are provided, the disclosure is not limited to such enzymes or methods.

For example, malonyl semialdehyde can be generated in vivo in a cell that has increased BAAT activity (for example due to expression of a BAAT having increased biological activity), and subsequently purified using standard methods known in the art. The malonyl semialdehyde is then contacted or incubated with the appropriate enzymes to generate the desired downstream organic chemical in vitro. For example, to generate 3-HP from malonyl semialdehyde, malonyl semialdehyde can be contacted with a peptide having 3-hydroxypropionyl dehydrogenase activity to make 3-HP.

Derivatives of 3-HP, such as an ester of 3-HP, polymerized 3-HP, or 1.3 propanediol, can be generated from 3-HP in vitro. For example, 3-HP can be produced in vitro as described above, or produced in vivo and then isolated. The resulting 3-HP can be incubated in the presence of the appropriate enzymes (see FIG. 1 and the present disclosure). In one example, all of these enzymes are incubated with malonyl semialdehyde and the reactions allowed to proceed in vitro. In another example, purified 3-HP is treated with a chemical to generate the desired derivative. For example, 3-HP can be converted into a 3-HP ester by trans esterification, into 1,3-propanediol by hydrogenation, or dehydrated to form acrylic acid.

Production of Malonyl Semialdehyde and 3-HP and Derivatives Thereof In Vitro

Purified peptides having the desired enzymatic activity can be used to produce malonyl semialdehyde or 3-HP (or derivatives thereof such as 1,3-propanediol, acrylic acid, polymerized acrylate, esters of acrylate, esters of 3-HP, and polymerized 3-HP). For example, a preparation including a substantially pure peptide having BAAT activity can be used to catalyze the formation of malonyl semialdehyde from beta-alanine.

Further, cell-free extracts containing a peptide having the desired enzymatic activity can be used alone or in combination with purified peptides or cells to produce 3-HP or derivatives thereof. For example, a cell-free extract that includes a peptide having BAAT activity and 3-HP dehydrogenase activity can be used to form 3-HP from beta-alanine. Any method can be used to produce a cell-free extract. For example, osmotic shock, sonication, or a repeated freeze-thaw cycle followed by filtration or centrifugation can be used to produce a cell-free extract from intact cells.

A purified peptide or cell-free extract can be used to produce 3-HP that is, in turn, treated chemically to produce another compound. For example, a chemical process can be used to modify 3-HP into a derivative such as 1,3-propanediol, acrylic acid, polymerized acrylate, esters of acrylate, esters of 3-HP, and polymerized 3-HP.

Fermentation of Cells to Produce Organic Acids

Methods are provided for producing malonyl semialdehyde and 3-HP (as well as derivatives thereof) that include in vivo methods (for example alone or in combination with vitro methods). The in vivo methods can include culturing the cell (such as a microorganism) having the appropriate enzyme activities in culture medium such that desired product is produced. In general, the culture media or culture conditions can be such that the cells grow to an adequate density and produce the product efficiently. For large-scale production processes, any method can be used such as those described elsewhere (Manual of Industrial Microbiology and Biotechnology, $2^{nd}$ Edition, Editors: Demain and Davies, ASM Press; and Principles of Fermentation Technology, Stanbury and Whitaker, Pergamon).

Briefly, a tank (such as a 1 gallon, 5 gallon, 10 gallon, 50 gallon, 100 gallon, 200 gallon, 500 gallon, or more tank) containing appropriate culture medium with, for example, a glucose carbon source is inoculated with one or more of the disclosed cells (such as microorganism). After inoculation, the cells are incubated to allow biomass to be produced. Once a desired biomass is reached, the broth containing the cells can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose, while the second tank contains medium with glucose.

Once transferred, the cells can be incubated to allow for the production of beta-alanine, malonyl semialdehyde, 3-HP or 3-HP derivatives. Once produced, any method can be used to isolate the formed product. For example, common separation techniques can be used to remove the biomass from the broth, and common isolation procedures (such as extraction, distillation, and ion-exchange procedures) can be used to obtain the desired product from the cell-free broth. Alternatively, the product can be isolated while it is being produced, or it can be isolated from the broth after the product production phase has been terminated. In some examples, the cells are isolated and the desired product extracted from the cells.

Enzymes

The disclosed cells can include one or more of the following enzymes. Such enzymes can be endogenous, exogenous, or combinations thereof. The term "peptide having enzymatic activity" refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as PEP carboxylase, pyruvate carboxylase, aspartate aminotransferase, aspartate decarboxylase, BAAT, 3-HP dehydrogenase, lipase, esterase, aldehyde dehydrogenase, and alcohol dehydrogenase.

Peptides having PEP carboxylase activity as well as nucleic acid encoding such peptides can be obtained from various species including, but not limited to, *Streptomyces coelicolor, Thermosynecliococcus vulcamis*, and *E. coli*. PEP carboxylase activity refers to the ability to convert PEP to oxaloacetate. For example, PEP carboxylase nucleic acids and proteins are disclosed in GenBank Accession Nos: AB057454, AF177946, or X05903 (nucleic acids) and BAB64533, AAD53311, or CAA29332 (proteins). It will be appreciated that publicly available sequences can contain variations as long as the peptide retains PEP carboxylase activity.

Peptides having pyruvate carboxylase activity as well as nucleic acid encoding such peptides can be obtained from various species including, but not limited to, *Rhizobium etli, Corynebacterium glutamicum*, and *Bacillus stearothermophilus*, and *E. coli*. Pyruvate carboxylase activity refers to the ability to convert pyruvate to oxaloacetate. For example, pyruvate carboxylase nucleic acids and proteins are disclosed in GenBank Accession Nos: U51439, AF038548 or D83706 (nucleic acids) and AAC44388, AAB92588, or BAA12072 (proteins). It will be appreciated that publicly available sequences can contain variations as long as the peptide retains pyruvate carboxylase activity.

Peptides having aspartate aminotransferase activity as well as nucleic acid encoding such peptides can be obtained from various species including, but not limited to, *Rhizobium meliloti, Thermus thermophilus*, and *E. coli*. Aspartate aminotransferase activity refers to the ability to convert oxaloacetate to aspartate. For example, aspartate aminotransferase nucleic acids and proteins are disclosed in GenBank Accession Nos: L05064, D38459, or X03629 (nucleic acids) and AAA26245, BAA07487, or CAA27279 (proteins). It will be appreciated that publicly available sequences can contain variations as long as the peptide retains aspartate aminotransferase activity.

Peptides having aspartate decarboxylase activity as well as nucleic acid encoding such peptides can be obtained from various species including, but not limited to, *Corynebacterium glutamicum, Mesorhizobium loti, Clostridium acetobutylicum, Streptomyces avermitilis*, and *E. coli*. Aspartate decarboxylase activity refers to the ability to convert aspartate to beta-alanine. For example, aspartate decarboxylase nucleic acids and proteins are disclosed in GenBank Accession Nos: AF116114, AF311738, L17086 as well as SEQ ID NOS: 38 and 40 (nucleic, acids), and GenBank Accession Nos: AAD28430, AAG47796, AAA24271, as well as SEQ ID NOS: 39 and 41 (proteins). It will be appreciated that publicly available sequences can contain variations as long as the peptide retains aspartate decarboxylase activity.

Peptides having BAAT activity as well as nucleic acid encoding such peptides can be obtained from various species including, but not limited to, *Pseudomonas aeruginosa, Pseudomonas putida*, and *E. coli*. BAAT activity refers to the ability to convert beta-alanine to malonyl semialdehyde. For example, BAAT nucleic acids and proteins are disclosed in GenBank Accession Nos: AE004091 or AE015451 as well as SEQ ID NOS: 3, 5, 7, 9, 11, 13, 16 and 18 (nucleic acids), and GenBank Accession Nos: AAG08698 or P28269 as well as SEQ ID NOS: 4, 6, 8, 10, 12, 14, 17, and 19 (proteins). It will be appreciated that publicly available sequences can contain variations as long as the peptide retains BAAT activity.

Peptides having 3-HP dehydrogenase activity as well as nucleic acid encoding such peptides can be obtained from various species including, but not limited to, *Rhodobacter sphaeroides, Pseudomonas aeruginosa. Pseudomonas putida*, and *E. coli*. 3-HP dehydrogenase activity refers to the ability to convert malonyl semialdehyde to 3-HP. For example, 3-HP dehydrogenase nucleic acids and proteins are disclosed in GenBank Accession Nos: AF316325, M84911, NC002516. AE015451 as well as SEQ ID NOS: 20, 22, 26, 29 and 30 (nucleic acids), and GenBank Accession Nos: AAL26884, AAA25892, NP_252259. AAN70239, as well as SEQ ID NOS: 21, 23, 27, and 31 (proteins). It will be appreciated that publicly available sequences can contain variations as long as the peptide retains 3-HP dehydrogenase activity. For example, nucleic acid that encodes a peptide having 3-HP dehydrogenase activity can be obtained from the 3-hydroxyisobutyrate dehydrogenase (mmsB) gene of *Pseudomonas aeruginosa* and can have a sequence as set forth in GenBank accession number M84911 (with a corresponding protein sequence shown in GenBank accession number AAA25892.1).

Peptides having lipase activity as well as nucleic acid encoding such peptides can be obtained from various species including, without limitation, *Candida rugosa, Candida tropicalis*, and *Candida albicans*. Lipase activity refers to the ability to catalyze the hydrolysis or formation of ester bonds, in particular, between 3-HP and an alcohol. For example, lipase nucleic acids and proteins are disclosed in GenBank Accession Nos: A81171, Z30945, AF188894 (nucleic acids) and Z30945 and AF188894 (proteins). It will be appreciated that publicly available sequences can contain variations as long as the peptide retains lipase activity.

Peptides having esterase activity as well as nucleic acid encoding such peptides can be obtained from various species including, without limitation, *Candida rugosa, Candida tropicalis*, and *Candida albicans*. Esterase activity refers to the ability to catalyze the hydrolysis or formation of ester bonds, in particular, to form an ester linkage between two molecules of 3-HP or between one molecule of 3-HP and a polymer of 3-HP, or between two polymers of 3-HP. For example, esterase nucleic acids and proteins are disclosed in GenBank Accession Nos: Z30945 and AF188894 (nucleic acids) and CAA83122 and AAF35171 (proteins). It will be appreciated that publicly available sequences can contain variations as long as the peptide retains esterase activity.

Peptides having aldehyde dehydrogenase (EC 1.2.1.-) activity as well as nucleic acid encoding such peptides can be obtained from various species including, without limitation, *Pseudomonas putida, E. coli*, and *S. cerevisiae*. Aldehyde dehydrogenase activity refers to the ability to reduce a carboxylic group to an aldehyde group, using NADH or NADPH as the reductant. For example, aldehyde dehydrogenase nucleic acids and proteins are disclosed in GenBank Accession Nos: AB100375, L40742, and Z17314 (nucleic acids) and BAD07372, AAC36938, and CAA78962 (proteins). It will be appreciated that publicly available sequences can contain variations as long as the peptide retains aldehyde dehydrogenase activity.

Peptides having alcohol dehydrogenase activity (EC 1.1.1.1) as well as nucleic acid encoding such peptides can be obtained from various species including, without limitation, *Pseudomonas putida, Z. mobilis*, and *S. cerevisiae*. Alcohol dehydrogenase activity refers to the ability to reduce an aldehyde group to an alcohol group, using NADH or NADPH as the reductant. For example, alcohol dehydrogenase nucleic acids and proteins are disclosed in GenBank Accession Nos: AB100375, M32100, and M38457 (nucleic acids) and BAD07371, AAA27682, and AAA34411 (proteins). It will be appreciated that publicly available sequences can contain variations as long as the peptide retains alcohol dehydrogenase activity.

Although particular examples of enzymes that can be used are disclosed, one skilled in the art will appreciate that a nucleic acid molecule encoding a peptide having the desired enzymatic activity can be identified and obtained using methods known in the art. For example, nucleic acid molecules that encode a peptide having the desired enzymatic activity can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known enzymatic peptides. Sequence alignment software such as MEGALIGN (DNASTAR, Madison, Wis., 1997) can be used to compare various sequences. Further, nucleic acid and amino acid databases (such as GenBank and EMBL) can be used to identify a nucleic acid sequence that encodes a peptide having the desired enzymatic activity. Briefly, any amino acid sequence having at least 80% homology to a peptide having the desired enzymatic activity (such as a PEP carboxylase), or any nucleic acid sequence having at least 50% homology to a sequence encoding a peptide having the desired enzymatic activity can be used as a query to search GenBank. The identified peptides then can be analyzed to determine whether or not they exhibit the desired enzymatic activity.

Nucleic acid hybridization techniques can also be used to identify and obtain a nucleic acid molecule that encodes a peptide having the desired enzymatic activity. Briefly, a nucleic acid molecule that encodes a known enzymatic peptide, or fragment thereof, can be used as a probe to identify similar nucleic acid molecules by hybridization under conditions of moderate to high stringency. Such similar nucleic acid molecules then can be isolated, sequenced, and analyzed to determine whether the encoded peptide has the desired enzymatic activity.

Expression cloning techniques also can be used to identify and obtain a nucleic acid molecule that encodes a peptide having the desired enzymatic activity. For example, a substrate known to interact with a particular enzyme can be used to screen a phage display library containing that enzyme. Phage display libraries can be generated as described (Burritt et al., *Anal. Biochem.* 238:1-13, 1990), or can be obtained from commercial suppliers such as Novagen (Madison, Wis.).

Peptide sequencing techniques can also be used to identify and obtain a nucleic acid molecule that encodes a peptide having the desired enzymatic activity. For example, a purified peptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid encoding the polypeptide by PCR. Once obtained, the nucleic acid can be sequenced, cloned into an appropriate expression vector, and introduced into a microorganism.

Recombinant Expression of Proteins

The enzymes described herein (such as the enzymes listed in FIG. 1) can be produced individually or in combination in a cell. Methods for producing recombinant proteins are well known in the art, and therefore, the scope of this disclosure includes recombinant expression of any enzyme disclosed herein. For example, recombinant nucleic acid molecules can be used to generate the cells and practice the methods disclosed herein. In particular examples, the disclosed cells (or methods that use such cells) include at least one exogenous nucleic acid molecule.

With the disclosed and publicly available enzyme nucleic, acid and amino acid enzyme sequences, such as PEP carboxylase, pyruvate carboxylase, aspartate aminotransferase, aspartate decarboxylase, BAAT, 3-HP dehydrogenase, lipase, esterase, aldehyde dehydrogenase, and alcohol dehydrogenase (as well as variants, fragments and fusions thereof that retain the desired enzyme activity), the expression or purification of such proteins by standard laboratory techniques is enabled. One skilled in the art will understand that peptides can be produced recombinantly in any cell or organism of interest, and purified prior to use, for example prior to production of 3-HP or derivatives thereof.

The peptides having a particular enzymatic activity can be a peptide that is either naturally-occurring or non-naturally-occurring. A naturally-occurring peptide is any peptide having an amino acid sequence as found in nature, including wild-type and polymorphic peptides. Naturally-occurring peptides can be obtained from any species including, but not limited to, yeast, plant, fungal, and bacterial species. A non-naturally-occurring peptide is any peptide having an amino acid sequence not found in nature (such as SEQ ID NOS: 5-14, and 16-19). Thus, a non-naturally-occurring peptide can be a mutated version of a naturally-occurring peptide, or an engineered peptide. For example, a non-naturally-occurring peptide having increased BAAT activity can be a mutated version of a naturally-occurring BAAT peptide. A peptide can be mutated by, for example, sequence additions, deletions, substitutions, or combinations thereof using methods known in the art.

Transformed cells can be used to perform one or more steps of the steps in the pathways described herein or the transformed cells can be used to produce the disclosed peptides for subsequent use in vitro. For example, an individual microorganism can contain exogenous nucleic acid(s) encoding each peptide needed to perform the steps depicted in FIG. 1, such as the enzymes needed to produce beta-alanine, malonyl semialdehyde, or 3-HP (or derivatives thereof). Such cells can contain any number of exogenous nucleic acid molecules. For example, a particular cell can contain at least one, at least two, at least three, or at least four different exogenous nucleic acid molecules with each one encoding the peptide(s) necessary to convert PEP or pyruvate into beta-alanine (or a later product such as malonyl semialdehyde or 3-HP) as shown in FIG. 1, or a particular cell can endogenously produce peptides for converting pyruvate into beta-alanine while containing exogenous nucleic acid molecules that encode the peptides for converting beta-alanine into 3-HP.

Nucleic acid molecules encoding the enzymes described herein can be introduced into a cell using standard molecular biology methods. A single nucleic acid molecule can encode more than one enzyme or other desired molecule. For example, operons including two or more nucleic acid sequences, such as two, three, four, five, six, or even seven sequences, can be used. For example, each nucleic acid sequence, can encode a PEP carboxylase, pyruvate carboxylase, aspartate aminotransferase, aspartate decarboxylase, BAAT, 3-hydroxypropionate dehydrogenase, lipase, esterase, aldehyde dehydrogenase, or alcohol dehydrogenase. In a particular example, the recombinant nucleic acid sequence includes a sequence encoding one or more of PEP carboxylase, pyruvate carboxylase, aspartate aminotransferase, aspartate decarboxylase, BAAT, 3-hydroxypropionate dehydrogenase, lipase, esterase, aldehyde dehydrogenase, and alcohol dehydrogenase.

Recombinant nucleic acid sequences can include a regulatory element that promotes the expression of the nucleic acid sequence encoding the enzyme. Typically, regulatory elements are DNA sequences that regulate, the expression of other DNA sequences at the level of transcription. Thus, regulatory elements include, without limitation, promoters, enhancers, and the like. For example, one or more promoter sequences can be used to promote expression of a coding sequence by placing the promoter upstream of the cDNA sequence. In one example, a non-native promoter that enhances expression of the coding sequence relative to the native promoter is used. Examples of promoters include, without limitation, constitutive promoters, and promoters responsive or unresponsive to a particular stimulus (such as light, oxygen, chemical concentration). The disclosed nucleic acid molecules can be incorporated into a vector, which can be used to transform a cell, or be incorporated into the genome of the cell, or both. For example, a cDNA encoding the desired enzyme, is ligated into an expression vector, such as a bacterial expression vector. Other cloning vehicles, such as other plasmids, bacteriophages, cosmids, animal viruses and yeast artificial chromosomes can be used. These vectors can be introduced into a variety of hosts including simple or complex organisms, such as bacteria, fungi, or plants, which are rendered transgenic by the introduction of the heterologous cDNA.

A single exogenous nucleic acid molecule can encode one, or more than one peptide. For example, a single exogenous nucleic acid molecule can contain sequences that encode two, three, or even four different peptides, such as at least two of the following: PEP carboxylase, pyruvate carboxylase, aspartate aminotransferase, aspartate decarboxylase, BAAT, 3-HP dehydrogenase, lipase, esterase, aldehyde dehydrogenase, and alcohol dehydrogenase. Further, the cells described herein can contain a single copy, or multiple copies (such as at least 5, at least 10, at least 20, at least 35, at least 50, at least 75, at least 100 or at least 150 copies), of a particular exogenous nucleic acid molecule. The cells described herein can contain more than one particular exogenous nucleic acid. For example, a particular cell can contain about 15 copies of exogenous nucleic acid molecule X as well as about 25 copies of exogenous nucleic acid molecule Y.

Any method can be used to introduce an exogenous nucleic acid molecule into a cell. The transfer of DNA into eukaryotic cells is a conventional technique. Non-limiting exemplary methods for introducing a nucleic acid molecule into cells include heat shock, lipofection, electroporation, conjugation, fusion of protoplasts, precipitation with calcium phosphate or strontium phosphate, DEAE dextran, microinjection, and biolistic delivery (for example see Ito et al., *J. Bacterol.* 153:163-8, 1983; Durrens et al., *Curr. Genet.* 18:7-12, 1990; Sambrook et al., Molecular cloning: A laboratory manual, Cold Spring Harbour Laboratory Press, New York, USA, second edition, 1989; and Becker and Guarente, *Methods in Enzymology* 194:182-7, 1991). In one example, cDNA can be introduced by infection with virus vectors, for example retroviruses (Bernstein et al. 1985, *Gen. Engrg.* 7:235) such as adenoviruses (Ahmad et al., 1986, *J. Virol.* 57:267) or Herpes (Spaete et al., 1982, *Cell* 30:295).

An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant.

EXAMPLE 1

Purification and Cloning of Beta-Alanine Aminotransferase

This example describes methods used to clone a native beta-alanine aminotransferase (BAAT) from *Streptomyces griseus*. One skilled in the art will appreciate that similar methods can be used to clone BAAT from any desired organism.

*Streptomyces griseus* (ATCC21897; American Type Culture Collection, Manassas, Va.) were grown in medium containing 1% glucose, 0.1% $K_2HPO_4$, 0.1% peptone, 0.05% yeast extract, 0.01% $MgSO_4.7H_2O$, and 0.2% beta-alanine. The cultures were grown in 1 L volumes in a 2.8 L flask at 26° C. with shaking at 250 rpm. After overnight growth the cells were harvested by centrifugation and washed with 0.2 volumes of 0.85% NaCl, and the cell pellet (~10 g of cells from 2 L media) was stored at −80° C. until use.

The cell pellet was thawed on ice. The cell paste was transferred to a mortar and ground with ~2 g sea sand. The cell/sand mixture was resuspended in ~30 ml buffer A (20 mM potassium phosphate pH 7.2, 20 μM pyridoxal phosphate, 0.01% beta-mercaptoethanol), transferred to a glass tube, and sonicated to lyse the cells. Cell debris and sand was removed by centrifugation (30,000×g for 30 minutes). The supernatant was applied to a DEAE sepharose column that had been equilibrated with buffer A, and protein was eluted with a step gradient (0%, 30%, 50%, 100%) with buffer B (buffer A+1 M NaCl). The beta-alanine aminotransferase activity eluted at the 50% step.

The fractions with activity were collected, concentrated and applied to a Superdex75 column equilibrated with buffer A+150 mM NaCl. Fractions with beta-alanine aminotransferase activity were pooled, desalted using a PD-10 column with 1 mM potassium phosphate pH 7.2, 20 μM pyridoxal phosphate, 0.01% beta-mercaptoethanol as the buffer, and the desalted fraction was applied to a hydroxyapatite column that was equilibrated with buffer HA (20 μM pyridoxal phosphate, 0.01% beta-mercaptoethanol) and 1% buffer HB (100 mM potassium phosphate, 20 ~M pyridoxal phosphate, 0.01% beta-mercaptoethanol). The protein was eluted with a stepwise gradient of buffer HB (1%, 10%, 20%, 100%). The beta-alanine aminotransferase activity eluted at the 100% step. The protein was concentrated and stored at −80° C.

The purified protein was run on an SDS polyacrylamide gel and the band at ~48,000 daltons excised and sequenced. Because the genome nucleotide sequence of *S. griseus* is not publicly available, the resulting peptide fragments were used to search the published *S. avermitilis* genome sequence using the BLAST software and to identify a homologous gene. Primers were designed to amplify the predicted open reading frame from *S. avermitilis* genomic DNA (ATCC#31267D): CGGGATCCCTAAACCGTGTACTCGTCC (SEQ ID NO: 1) and GGAATTCCATATGACCCCTCAGCCGAATC (SEQ ID NO: 2).

PCR was performed with the GC-Rich PCR system (Roche), and the resulting PCR fragment was digested with NdeI and BamHI and ligated using the Quick Ligation Kit (Roche) into pET28b that had been digested with NdeI and BamHI to construct pET28b/SaBAAT.

The native *S. avermitilis* BAAT cDNA and protein sequences are shown in SEQ ID NO: 3 and 4, respectively.

EXAMPLE 2

Selection of BAAT with Increased Biological Activity

This example describes methods used to isolate BAAT proteins (and the nucleotides that encode them) having increased activity towards beta-alanine. Similar methods can be used to identify other BAAT molecules.

Briefly, the selection method involves growing cells containing mutagenized libraries of BAAT on media with beta-alanine as the sole nitrogen source. Under these conditions, only cells that can convert beta-alanine to a central metabolite can grow. For example, the BAAT can convert beta-alanine and alpha-ketoglutarate to malonyl semialdehyde and glutamate, respectively, with glutamate entering central metabolism and supporting cell growth.

Mutagenic PCR was conducted based on the protocol of Cadwell and Joyce (*PCR Methods Appl.* 2:28-33, 1992). This method uses various dilutions of a mutagenic buffer containing 21.2 mM $MgCl_2$, 2.0 mM $MnCl_2$, 3.2 mM dTTP, and 3.2 mM dCTP, 6.3 and 9.4% (v/v) of mutagenic buffer were added to separate PCR reactions (each of final volume 100 μL), in addition to 1× Taq PCR buffer with 1.5 mM $MgCl_2$, 0.25 μM of forward and reverse vector primers, 200 μM of each dNTP, 5 ng of pET28b/SaBAAT DNA as template, 5% DMSO, and 10 units of Taq DNA polymerase (Roche). The PCR program consisted of an initial denaturation at 94° C. for 2 minutes; 30 cycles of 94° C. for 30 seconds, 54° C. for 45 seconds, and 72° C. for 2.25 minutes; and a final extension at 72° C. for 7 minutes.

The PCR product was digested with restriction enzymes BamHI and NdeI, ligated into the vector pPRONde similarly digested, and transformed into *E. coli* Electromax™ DH10B™ cells (Invitrogen, Carlsbad, Calif.). Plasmid pPRONde is a derivative of pPROLar.A122 (Clontech Laboratories, Inc., Palo Alto, Calif.) in which an NdeI site was constructed at the initiator ATG codon by oligonucleotide-directed mutagenesis using the QuikChange Site-Directed Mutagenesis kit from Stratagene. Plasmid DNA was isolated from randomly-chosen single colonies and sequenced to obtain an estimate of the mutation rate (3 changes per 1000 nucleotides). Multiple transformations were plated to LB media containing 25 μg/mL kanamycin to obtain approximately 90,000 colonies. Colonies were scrapped from plates and plasmid DNA prepared using a MiniSpin Plasmid procedure (Qiagen, Valencia, Calif.). The pooled plasmid DNA was concentrated by ethanol precipitation.

The mutagenized *S. avermitilis* BAAT plasmid library was transformed into electrocompetent cells of a ΔgabT strain of *E. coli* BW25113 (Datsenko and Wanner, *Proc. Natl. Acad. Sci. USA* 97:6640-5, 2000). The gabT gene deletion was used to prevent any possible activity on beta-alanine by the host 4-aminobutyrate aminotransferase encoded by this gene. Transformants were grown for 1.5 hour in SOC, media, centrifuged, washed with 0.85% NaCl, and resuspended in 0.75 mL of NaCl to remove traces of nitrogen sources. 200 μL was used to inoculate 25 mL of M9 minimal medium without $NH_4Cl$, supplemented with 0.5% glycerol, 50 μM pyridoxine-HCl, 100 μM IPTG, 100 mM MOPS pH 7.0, 40 μg/mL kanamycin, and 5 mM beta-alanine. After 5 days of aerobic growth, 1 mL of culture was used to inoculate 25 mL of fresh media. After 6 days of growth, 12,000 colonies were plated on rich media and plasmid DNA was isolated from the combined colonies.

Approximately 700 ng of DNA was transformed into naïve cells of *E. coli* ΔgabT. Transformants were recovered one hour in SOC media, centrifuged, washed with 0.85% NaCl, and used to inoculate 25 mL of the above media. After 3 days, the culture was subcultured into fresh media. Two days later, platings were done to obtain 20,000 colonies on LB media containing 25 μg/mL kanamycin. Plasmid DNA was isolated from these combined colonies and precipitated with ammonium acetate and ethanol. This library was used for screening in Example 3. The subculture was also diluted and plated on minimal media with 5 mM beta-alanine to obtain individual colonies. The largest individual colonies were patched to fresh media and those showing the best growth were patched to minimal media with 5 mM beta-alanine, 50 μg/mL water-soluble paranitrosaniline, and 250 μg/mL $NaHSO_4$.

Plasmid DNA was isolated from three, colonies that showed good color development on the dye media, and was transformed into naïve competent cells of the *E. coli* ΔgabT strain. The retransformed colonies were tested in a liquid growth test in the M9 minimal media given above supplemented with either 5 mM beta-alanine or 5 mM glutamate. Improved clones isolated by this selection method were sequenced and multiple clones were shown to carry a mutation resulting in the change of serine at position 24 to threonine (S24T). This variant is referred to as BAAT1 (SEQ ID NO: 5 and 6). A set of other improved clones, although with less activity than the S24T mutants, carried the mutations T83A, S314T, and E348G (BAAT1b; SEQ ID NOS: 7 and 8).

Purpald® Assays

Clones were also tested directly for malonyl semialdehyde production using the Purpald® (Aldrich) aldehyde trapping dye. The reaction mixture included 50 mM Na borate buffer, pH 8.0, 0.035% beta-mercaptoethanol, 10 mM alpha-ketoglutarate, 0.5 mM pyridoxal phosphate, 50 mM beta-alanine, and 50-500 μg cell extract or approximately 20 μg purified protein. Alternatively, a 100 mM K phosphate pH 8 buffer can be used in place of the borate buffer and beta-mercaptoethanol.

The reaction was incubated at 37° C. for 30 minutes and then stopped by addition of an equal volume of 10 mg/mL Purpald® in 1N NaOH. Once a purple color began to develop, the absorbance of the reactions were read spectrophotometrically at 535 nm.

Second Round of Mutagenesis

A mutagenic library was made using the two different first-round mutants (SEQ TD NOS: 5 and 7) and wildtype *S. avermitilis* beta-alanine aminotransferase (SEQ ID NO: 4) as template. The library was constructed as described above with the exception that 3.9% and 5.5% mutagenic buffer and templates were cloned in the pPRONde vector. The PCR program included an initial denaturation at 94° C. for 2 minutes; 30 cycles of 94° C. for 30 seconds, 55° C. for 45 seconds, and 72° C. for 2 minutes; and a final extension at 72° C. for 5 minutes. The PCR product was gel-purified and cloned as described above with the addition of a DpnI digestion step to eliminate any residual template.

The ligation utilized equal amounts of DNA from the three templates. Multiple transformations of the ligation were made into the BW25113 ΔgabT strain. The transformations were recovered in SOC media for 2 hours, pooled, washed, and resuspended in 1 mL of 0.85% NaCl. 300 μL of the resuspension was used to inoculate flasks containing 25 mL of selection media, as described above, containing either 1 mM, 5 mM, or 20 mM beta-alanine. After cultures had grown at 37° C. to $OD_{600}$ 0.5-1.8, approximately 6,000 colonies of each culture were plated on 2 plates of LB containing 25 μg/mL kanamycin. Colonies were scrapped from plates and plasmid DNA prepared using a MiniSpin Plasmid procedure, separately for each concentration of beta-alanine. Plasmid DNA was precipitated to obtain concentrations of 350-372 ng/uL. Two μL of each sublibrary were retransformed into the BW25113ΔgabT strain, in order to reduce the contribution of host mutations to culture growth on beta-alanine.

Transformations were recovered for one hour in SOC media, washed, and resuspended in 0.85% NaCl. The resuspension was used to inoculate liquid selection media with 1 mM, 5 mM, or 20 mM beta-alanine, and also to plate distributed colonies onto plates of the same selection media. Several colonies that grew well in the distributed platings were streaked for purification and further tested in liquid growth tests. These liquid growth tests utilized 3 mL of selection media in glass culture tubes. Approximately equal amounts of inoculum were used to inoculate the cultures, and plasmid DNA was isolated from promising cultures and retransformed into naïve BW25113ΔgabT, and retransformants were retested in a liquid growth test. Retransformants that looked promising were grown in rich media and induced with 1 mM IPTG at 30 C for 4 hours. Cell extract was obtained using BugBuster extraction reagent (Novagen, Madison, Wis.) and assayed using the previously-described Purpald® reagent.

The highest performing mutant, isolated from the 5 mM beta-alanine selection, carried an F113L mutation in addition to the S24T mutation from the first round of mutagenesis and selection; this variant is referred to as BAAT2 (SEQ ID NOS: 9 and 10), and was cloned into pET28b to allow protein purification and kinetic analyses of purified protein.

Third Round of Mutagenesis

BAAT2 (SEQ ID NO: 9) was used as template for a third round of mutagenesis. Mutagenesis was conducted as described above, using 3.9 and 5.5% mutagenic buffer. The mutated PCR product was cloned into the pPRONde vector, and the ligation reaction was transformed into the BW25113ΔgabT strain and subjected to growth in selection media containing 2 and 5 mM beta-alanine. Subcultures into fresh selection media were made every two days. The third subcultures were plated on selection media to achieve approximately 250 colonies per plate. The largest colonies were patched to fresh selection plates and the fastest growing colonies were tested in liquid growth tests using selection media. Plasmid DNA was isolated from the fastest growing clones and retransformed into the selection host. The retransformed clones were retested in a liquid growth test and with the Purpald® assay as described above.

The best variant (BAAT3, SEQ ID NOS: 11 and 12) derived from the third round of mutagenesis contained an additional A133T mutation, and was from the 5 mM beta-alanine selection. This mutant was cloned into pET28b to allow protein purification and kinetic analyses of purified protein.

Directed Mutagenesis of P3H Mutation into BAAT2 and BAAT3 Mutants

A high-throughput screen for improved beta-alanine aminotransferases, based on increased activity with the Purpald® reagent, is described in Example 3. This screen resulted in the isolation of a variant with the additional change of P3H (SEQ ID NOS: 13 and 14, nucleic acid and protein sequence, respectively), and this mutation was transferred to the BAAT2 (SEQ ID NO: 9) and BAAT3 (SEQ ID NO: 11) variants using the Quikchange® Multi Site-Directed Mutagenesis Kit (Stratagene). The primer used for mutagenesis had the sequence: 5'Phos-AAGGTACATATGACCCATCAGC-CGAATCCC-3' (SEQ ID NO: 15).

The DpnI-treated reaction was transformed directly into the BW25113ΔgabT strain. Colonies containing the desired mutation were identified by PCR and confirmed by sequencing. Assays with the Purpald reagent on extracts from induced cells confirmed an approximate 2.5 fold increase in aldehyde production attributable to the P3H mutation with 50 mM substrate. The variant carrying the mutations from the third round of mutagenesis and selection and the P3H change is denoted BAAT3mL (SEQ ID NOS: 16 and 17).

Fifth Round of Mutagenesis

BAAT3ML (SEQ ID NO: 16) was used as template for a fifth round of mutagenesis. Mutagenesis was conducted as described above, using 3.9 and 5.5% mutagenic buffer. The mutated PCR product was cloned into the vector pCEK/Pgaam8-1/PpmmsB/Spaat, where Pgaam8-1 is the gene encoding an alanine 2,3-aminomutase. PpmmsB is the gene encoding Pseudomomas putida methyl-malonyl semialdehyde dehydrogenase (see Example 5), and Spaat is the gene encoding a Schizosaccharomyces pombe glutamate-pyruvate aminotransferase. Cleaned ligation reaction was transformed into E. coli Electromax™ DH10B™ cells and a library was constructed by preparing plasmid DNA from a pool of approximately 78,000 colonies. 2.3 ug of the library was transformed into BW25113ΔgabT or a BW25113 strain with a promoter integrated in front of the ydfG gene (BW25113ΔgabT/$P_{lac/ara}$ydfG). This latter strain was used to reduce possible toxic effects of malonyl semialdehyde production, as the ydfG gene product can reduce malonyl semialdehyde to 3-hydroxy propionic acid (Example 5).

After recovery, transformations were subjected to growth in selection media (M9 minimal medium without $NH_4Cl$, supplemented with 1 mM beta-alanine, 1% glucose, 50 μM pyridoxine-HCL, 500 μM IPTG, 100 mM MOPS pH 7.0, 40 μg/mL kanamycin). After 2-3 subcultures into fresh selection media, colonies were plated on selection media to achieve approximately 400 colonies per plate. The largest colonies were patched to fresh selection plates and the fastest growing colonies were tested in liquid growth tests using selection media.

Plasmid DNA was isolated from the fastest growing clones and retransformed into the BW25113ΔgabT/$P_{lac-ara}$ydfG host. The retransformed clones were retested in a liquid growth test and the plasmid isolated from the retransformants to confirm plasmid stability. The best mutant was cloned into pET28b to allow protein purification and kinetic analyses of purified protein The best variant derived from the fifth round of mutagenesis is designated BAAT5-9 (SEQ ID NOS: 18 and 19, nucleic acid and protein sequence, respectively) and contained the additional coding mutation D110N and the silent mutations c207t, c381g, and t471c.

FIGS. 2A-B show an amino acid sequence alignment of the improved beta-alanine aminotransferases (SEQ ID NOS: 6, 10, 12, 14, 17, and 19) as compared to the native sequence (SEQ ID NO: 4).

EXAMPLE 3

Screening for Improved Beta-Alanine Aminotransferases

This example describes a high-throughput screen used to identify amino acid changes that can increase BAAT biological activity.

Single colonies each carrying a clone from the first round PCR-mutagenized library from Example 2 were grown in single wells of 384-well microtiter plates with a transparent bottom to allow densitometric reading. The medium was LB containing kanamycin (50 μg/ml) and IPTG (1 mM). Plates with the inoculated colonies were covered with a lid and put on a rotation device for 24 hours in an incubator at 37° C. A robotic handling system (Beckman-Coulter Biomeck with an ORCA arm running with internally developed software and equipped with an interfaced spectrophotometer) was used to identify colonies with an $OD_{600}$ above a fixed threshold, and 45 μl of these cultures were then transferred into 96 well plates.

Five μl of Popculture® (Novagen) solution (100 μl Popculture®, 10 μl rLyso (dil. 1/750) and 2 μl benzonase) were added to each well and mixed twice. After an incubation of 30 minutes, 100 μl of a substrate mix (0.13 mM pyridoxal phosphate, 66.5 mM K phosphate, 13.3 mM alpha-ketoglutarate, 26.6 mM beta-alanine) were added. Plates were then removed from the robot carousel, sealed with an aluminum self-adhesive film and mixed at 200 rpm at 37° C.

After two hours, the aluminum seal was removed, the plates were put back onto the robot carousel and 140 μl of a solution of Purpald® (Aldrich) (10 mg Purpald® in 1 ml 2M NaOH) were added to detect the aldehyde. Plates were incubated for 45 minutes at room temperature for color development. Possible bubbles, created during Purpald® incubation, were removed by adding 10 μl of 95% EtOH. Robotized colorimetric test readings were done at 540 nm.

Clones identified as producing increased amounts of aldehyde were recovered, their plasmids purified, and the beta-alanine aminotransferase genes sequenced. These clones carried a mutation resulting in the additional change of a proline at position 3 to histidine (P3H) (SEQ ID NOS: 13 and 14, nucleic acid and protein sequence, respectively).

EXAMPLE 4

Assay of Beta-Alanine Aminotransferase Activity

This example describes an in vitro method that was used to measure BAAT biological activity. Such an assay can be used to determine if particular BAAT variants, fusions, or fragments retain the desired BAAT biological activity.

Beta-alanine aminotransferases (SEQ ID NOS: 3, 5, 9, 11, 16 and 18) cloned into pET28b were purified using metal affinity chromatography as described by the manufacturer (Novagen). The enzymatic activity of the purified enzymes was measured by following the production of L-glutamate from beta-alanine and alpha-ketoglutarate. Reaction mixtures contained 50 mM HEPPS, pH 8.0, 10 mM alpha-ketoglutarate, 0.2 mM pyridoxal 5-phosphate, and varying amounts of beta-alanine and enzyme. Incubations were carried out at 25° C., and aliquots of 0.05 mL were removed at intervals of 30 seconds and added to 0.15 mL of reaction quench buffer (50% formic acid/50%50 mM HEPPS pH 8). L-glutamate was determined by high-pressure ion exchange chromatography on an AMINOSep-511 column (Transgenomic) developed using mobile phases of pH 3.28 and pH 7.48 buffers from Pickering, followed by post-column derivatization with O-phthalaldehyde and fluorometric detection.

The specific activities of the improved BAATs and their $K_m$ for beta-alanine are shown in Table 1.

TABLE 1

Properties of improved beta-alanine aminotransferases

| Enzyme (mutations) | Specific Activity ($U^a$/mg) | $K_m^b$ (mM) |
|---|---|---|
| Wildtype BAAT | 0.3 | 2.5 |
| BAAT1 (S24T) | 1.6 | 7.3 |
| BAAT2 (S24T, F113L) | nd$^c$ | nd |
| BAAT3 (S24T, F113L, A133T) | 1.2 | 14.7 |
| BAAT3ML (P3H, S24T, F113L, A133T) | 2.5 | 21 |
| BAAT5-9 (P3H, S24T, D110N, F113L, A133T) | 3.3 | 25 |

$^a$1 U = 1 μmole/min
$^b$for beta-alanine
$^c$not determined

EXAMPLE 5

Cloning of 3-HP Dehydrogenases

This example describes methods of cloning 3-HP dehydrogenases that can be used to convert malonyl semialdehyde to 3-HP, for example in a cell.

A gene (SEQ ID NO: 20) encoding a protein having 3-HP dehydrogenase activity (PammsB) was isolated from *Pseudomonas aeruginosa* as described in Gokarn et al., US 2004/0076982. The purified enzyme (SEQ ID NO: 21) had a specific activity of 70 U/mg and a $K_m$ for malonyl semialdehyde of 4.5 mM; NADH is the preferred reductant.

Another gene (SEQ ID NO: 22) encoding a protein having 3-HP dehydrogenase activity (SEQ ID NO: 23) was isolated from *Alcaligenes faecalis* M3A as described in Liao et al. PCT WO 03/062173 A2.

Yet another gene encoding a protein having 3-HP dehydrogenase activity was cloned by amplification of the mmsB gene from genomic DNA (ATCC 47054D) of *P. putida* strain KT2440. The amplification primers allowed cloning of the (PpmmsB), and provided an introduced ribosomal binding site, into NotI and XbaI sites of a pPRONde vector containing the BAAT3mL beta-alanine aminotransferase.

(SEQ ID NO: 24)
5'-TACTGCGGCCGCAAGAAGGAGATATAGATATGCGTATTGCATTCATT
GGC-3'
and (SEQ ID NO: 25)
5'-CCTAGTCTAGATCAATCCTTCTTGCGATACCCCT-3'

SEQ ID NO: 26 and 27 are the nucleotide and protein sequences, respectively, of the *P. putida* 3-HP dehydrogenase gene. This enzyme showed higher production compared to the *P. aeruginosa* 3-HP dehydrogenase (SEQ ID NO: 21) and allowed more growth on beta-alanine as a sole nitrogen source in an *E. coli* BW25113 ΔydfG host carrying BAAT3ML.

To enhance protein production, a library containing various combinations of codons 2-7, as designed by the Proteoexpert program, was constructed in a pET28b/BAAT5-9 vector. A primer was utilized that contained degenerate nucleotides incorporating changes suggested by the Proteoexpert software (48 combinations).

(SEQ ID NO: 28):
5'-GGAGGTATTTATATGCGTATYGCWTTYATYGGHCTGGGCAACATGGG CGCGCC-3'

The primer also included 20 bases of sequence on either end of the degenerate region. Gene fragments immediately upstream and downstream of, but not containing, the degenerate region were amplified separately. The template used to make these fragments contained the BAAT5-9 gene, with the PpmmsB gene cloned downstream of it into BamHI and NheI restriction sites. The upstream fragment included a portion of the BAAT5-9 gene and ended with the 20 nucleotides upstream of the degenerate region. The downstream fragment began with the 20 bases downstream of the degenerate region and contained the 3' end of PpmmsB. The degenerated primer was then used to bridge these two fragments in a second DNA amplification using primers homologous to the 5' and 3' fragment ends. The PpmmsB gene, containing a library of degenerate codons for amino acid residues 3-7, was cut from the second round product with BamHI and NheI and cloned into the BamHI and NotI sites in the pET28B/BAAT5-9 vector.

After transformation into the strain BW25113 ΔpanD (DE3), random colonies were transferred to LB with 100 μM IPTG for induction. Colonies that grow well were transferred to selection media containing 5 mM beta-alanine and to selection media containing both beta-alanine and an aldehyde-trapping dye (pararosaniline chloride, Sigma P-3750). Selection media contained M9 salts without $NH_4Cl$, 100 mM MOPS pH 8.0, 100 μM pyridoxine-HCl, 1% glucose, 5 mM beta-alanine, 40 μg/mL kanamycin, 500 μM IPTG, and trace elements. A handful of colonies grew better than average on the selection media. Of these, colony number 31 was darker in color than the rest. Two colonies, including colony 31, were lighter in color on the dye media, as expected if the malonyl semialdehyde were quickly converted to 3-HP.

Several clones were tested in a biotransformation of beta-alanine to 3-HP. Clones were grown at 37° C. overnight in LB media containing 25 μg/mL kanamycin, and subcultured 1:24 into 12 mL of 2YT media containing 25 μg/mL kanamycin and 10 μM pantothenate. Cultures were grown at 37° C. and induced at OD 0.4-0.6 with 100 μM IPTG for 5 hours at 34° C. A culture volume having a total OD of 7200 was spun down and resuspended in 1.7 mL of biotransformation media. 1.5 mL of the resuspension was transferred to a 2 mL glass HPLC tube and placed at 34° C. with shaking at 225 rpm. Biotransformation media contained M9 salts without $NH_4Cl$, 100 mM MOPS pH 8.0, 100 μM pyridoxine-HCl, 1% glucose, 5 mM beta-alanine and 20 μM $Ca^{2+}$pantothenate. Samples collected after 17 hours were acidified by adding a 5% volume of 90% formic acid and were tested for 3-HP concentration by LC/MS. Colony 31 gave the highest percent conversion of beta-alanine to 3-HP (35 mg/L 3HP vs. 2 mg/L for the wild-type PpmmsB control) and also showed the highest expression of PpmmsB protein as judged by band density in an SDS polyacrylamide gel.

SEQ ID NO: 29 is the nucleotide sequence of PpmmsB31; the protein sequence is identical to SEQ ID NO: 27. The BAAT5-9/PpmmsB31 sequence was incorporated into several different operons for the production of 3-HP using standard cloning. DNA amplification, or directed mutagenesis techniques.

In another example, a genomic library screen was used to identify proteins that enhance expression of the BAAT by removing the potentially deleterious malonyl semialdehyde. This was performed by cloning the genomic library into a vector containing an active BAAT and selecting on minimal media containing beta-alanine as the only nitrogen source. Cells with inserts coding for proteins that enhance activity of the BAAT will grow more efficiently and thus be larger in size when grown on the selective media. The activity of the BAAT could be enhanced, for example, by increased uptake of beta-alanine, decreased secretion of beta-alanine, enhanced cofactor utilization, or increased processing of malonyl semialdehyde.

Genomic DNA of E. coli ΔgabT was digested with restriction endonuclease Sau3AI and fragments of 1 to 3 Kb in size were gel-purified using a kit from Qiagen (Valencia. Calif.). The purified DNA was ligated into pPRONde vector containing an improved beta-alanine aminotransferase (BAAT2, SEQ ID NO: 9) and transformed into cells of E. coli ΔgabT. The transformation reaction was recovered for one hour in 1 mL of SOC media, centrifuged, washed with 0.85% NaCl, and resuspended in 1 mL of 0.85% NaCl. Twenty μL of the resuspension was plated on LB media containing 25 μg/ml kanamycin to obtain a colony count. The remaining transformation reaction was plated on M9 minimal media to obtain approximately 600 colonies per plate. This M9 media is based on standard M9 media except that $NH_4Cl$ is omitted, and supplemented with 0.5% glycerol, 50 μM pyridoxine-HCL, 100 μM IPTG, 100 mM MOPS pH 7.0, 40 μg/mL kanamycin, and 2 mM beta-alanine.

After two days of growth, 8 large colonies (from a total of ~7,000) were seen that were several-fold larger than the other colonies on the plate. These colonies were colony-purified, their plasmids were isolated, and the insert fragments compared by restriction enzyme digestion. Of the 8 colonies, 6 carried unique-sized inserts. The insert DNA fragments from these clones were sequenced and the sequence results were compared against the E. coli genome database using the BLAST software. All of the six clones were homologous to the same region of the E. coli genome. One of the genes contained within all of the inserts was the ydfG gene (SEQ ID NO: 30 and 31), which is annotated as a potential dehydrogenase. Hence the growth enhancing effect of increased expression of this gene due to its presence on multicopy plasmids may be due to its ability to convert malonyl semi-aldehyde to 3-HP, and thus either alleviate the potential toxicity of malonyl semialdehyde, or increase the rate of incorporation of nitrogen from beta-alanine to L-glutamate by removing one of the products of the reaction catalyzed by the improved beta-alanine aminotransferase.

Based on these results, the ydfG-encoded protein can be used in combination with BAAT to enhance 3-HP production. For example, a nucleic acid molecule expressing ydfG can be expressed in a cell along with BAAT to enhance production of 3-HP by the cell.

The ydfG gene was cloned into the pET28b vector (Novagen, Madison, Wis.) to allow purification and kinetic studies on purified protein. The primers used for this cloning had restriction sites added to allow cloning into NdeI and BamHI sites. GGTAGACATATGATCGTTTTAGTAACTG-GAGCAAC (SEQ ID NO: 32) and GTTCTCGGATCCT-TACTGACGGTGGACATTCAGTC (SEQ ID NO: 33). Fragment amplification was performed using Pfu DNA polymerase to minimize amplification errors, and used an annealing temperature of 58° C. A PCR product band of approximately 750 bp was gel-purified, digested with NdeI and BamHI, and ligated, using an NEB Quick Ligation method (New England BioLabs, Waverly Mass.), into pET28B vector that had been digested with the same enzymes. The ligation reaction was transformed into *E. coli* Electromax™ DH10B™ cells and plated on LB medium containing 25 µg/ml kanamycin. Plasmid DNA from a colony showing the correct insert size was sequenced and shown to be identical to the ydfG sequence from *E. coli* MG1655. The purified enzyme has a specific activity of 48.5 U/mg, and a $K_m$ of 3.7 mM for malonyl semialdehyde; NADPH is the only cofactor used by this enzyme and no activity is obtained with NADH.

Examples where the cofactor preference of a dehydrogenase was expanded or changed are known in the art, and these approaches can be applied to the development of a variant ydfG protein that utilizes NADH. Selection for growth on minimal media with beta-alanine as the sole nitrogen source, in the presence of a BAAT and a mutagenized ydfG gene, in a host whose intrinsic ydfG function is deleted (such as a ΔydfG *E. coli* strain), is one approach to the identification of an NADH-utilizing dehydrogenase.

EXAMPLE 6

Synthetic Operons Containing BAAT and 3-HP Dehydrogenase

This example describes operons that include a BAAT and a 3-HP dehydrogenase. Such operons can be transformed into a cell to permit production of 3-HP or derivatives thereof in a cell, for example by integrating the operon into the chromosome of the cell. Although particular BAAT and 3-HP dehydrogenases are described, one skilled in the art will appreciate that similar methods can be used with other BAATs (such as SEQ ID NOS: 5, 7, 9, 13, 16 or 19) and 3-HP dehydrogenases (such as SEQ ID NOS: 20, 22, or 30).

Integration of synthetic operons that include a BAAT (SEQ ID NO: 11) and a 3-HP dehydrogenase (SEQ ID NO: 27) was accomplished using Tn5-based system as described in Purvis et al. (*Appl. Environ. Microbiol.* 71:3761-9, 2005). Plasmid pCEK-BAAT3ML-PpmmsB was digested with restriction endonucleases XhoI and AvrII and the DNA fragment carrying the $P_{lac/ara}$ promoter and BAAT3ML-PpmmsB genes was ligated to plasmid pLOI3472 digested with XhoI and SpeI. The resultant construct, pLOI-Bm3, was then digested with PacI and the fragment carrying the $P_{lac/ara}$ promoter, BAAT3ML-PpmmsB genes, and kanamycin resistance marker flanked by FRT sites was ligated to pLOI3469 digested with the same endonuclease such that the entire fragment from pLOI-Bm3 is flanked by the outside end (OE) and inside end (IE) recognition sites for the Tn5 transposase present on pLOI3469. The ligation mixture was transformed into *E. coli* strain BW25141 (Datsenko and Wanner, *Proc. Natl. Acad. Sci. USA* 97:6640-5, 2000; BW25141 is a pir+ strain that supports replication of plasmids with an origin of replication derived from R6K such as pLOI3469). The resultant plasmid, pInt-Bm3, can be introduced into a non-pir+ target strain by transformation or conjugation, and action of the transposase causes the fragment from pLOI-Bm3 to be inserted at random sites in the target strain's chromosome, whereas pLOI-Bm3 itself is unable to replicate in this host.

In one example, pINT-Bm3 was transformed into *E. coli* 11303 ΔldhA Δpan(C-D) KIfld (where the genetic marker KIfld denotes the insertion of a synthetic $P_{lac/ara}$ promoter in front of the fldA gene). Selection for transformants with resistance to kanamycin but sensitivity to ampicillin (indicating loss of pLOI-Bm3 plasmid) resulted in strains in which the BAAT3ML-PpmmsB construct was integrated in the chromosome; strains carrying the integrated genes are designated INT(BAAT3ML/PpmmsB). The presence of these genes was demonstrated by growth on beta-alanine as the sole nitrogen source, as in Example 2, by production of 3-HP when beta-alanine is present, by observing the presence of the BAAT3ML and PpmmsB protein bands on SDS-polyacrylamide gel electrophoresis, or by enzymatic assay of extracts.

A similar construct carrying the improved variants BAAT5-9 (SEQ ID NO: 18) and PpmmsB31 (SEQ ID NO: 29) was also generated and integrated as described.

The integrated BAAT-mmsB genes were introduced into other strains of *E. coli* by P1-based transduction using the kanamycin-resistance marker to monitor incorporation of the genes into the recipient chromosome.

EXAMPLE 7

Cloning Aspartate Decarboxylase Genes

This example describes methods used to clone aspartate decarboxylase from *Clostridium acetobutylicum* and *Streptomyces avermitilis*. Aspartate decarboxylases can be used to convert aspartate to beta-alanine (see FIG. 1), for example in a cell in which an exogenous aspartate decarboxylase is expressed. One skilled in the art will appreciate that similar methods can be used to clone aspartate decarboxylase from other desired species, such as the species of cell in which 3-HP production is desired.

Genes encoding aspartate decarboxylase (encoded by the panD gene) were cloned from *C. acetobutylicum* and *S. avermitilis* as follows. Cells of *C. acetobutylicum* (ATCC 824) were grown anaerobically in 5 ml Reinforced *Clostridium* medium (Oxoid CM149) and the genomic DNA isolated using the Genomic "Puregene" DNA isolation kit (Gentra Systems; Minneapolis, Minn.). *S. avermitilis* genomic DNA was obtained from ATCC (ATCC 31267D). Both genomic DNAs were used as templates for amplification of respective panD genes.

The following primers were designed for the *C. acetobutylicum* panD: 5'-GGAATTCCATATGCATTTAAATATGT-TAAAATC-3' (CapanNdeF; SEQ ID NO: 34), and 5'-AC-CCAAGCTTTAGCCAATTGTCCCGTGCTTTTC-3' (CapanHdR; SEQ ID NO: 35). *C. acetobutylicum* was amplified in 100 µl PCR with 100 ng genomic DNA, CapanNdeF, CapanHdR primers and Pfu Turbo polymerase (Stratagene, La Jolla, Calif.). PCR conditions were 2 minutes at 94° C.; 10 cycles of 94° C. for 30 seconds, 48° C. for 30 seconds, and 72° C. for 45 seconds; 15 cycles of 94° C. for 30 seconds, 50° C. for 30 seconds, and 72° C. for 45 seconds, and at the end 7 minutes final extension at 72° C.

Primers for *S. avermitilis* panD were: 5'-GGAATTC-CATATGCTGCGTACCATGTTCAAGTC-3' (SapanNdeF; SEQ ID NO: 36), and 5'-ACACAAGCTTTAGGCGGT-GACGGCCTGC-3' (SapanHdR; SEQ ID NO: 37). *S. avermitilis* DNA was amplified in 100 µl PCR with 100 ng genomic DNA, SapanNdeF, SapanHdR primers and a mix of 2 ul rTth polymerase (Applied Biosystems, Foster City, Calif.) and 0.5 ul Pfu Turbo polymerase (Stratagene, La Jolla, Calif.). PCR conditions were: 2 minutes at 94° C.; 10 cycles of 94° C. for 30 seconds, 52° C. for 30 seconds, and 70° C. for 45 seconds; followed by 15 cycles of 94° C. for 30 seconds, 56° C. for 30 seconds, and 70° C. for 45 seconds, and at the end 7 minutes at 70° C.

The resulting PCR products were purified using Qiagen PCR purification kit (Qiagen, Inc., Valencia, Calif.) according to the manufacturer's instructions. Purified PCR products and pPRONde vector were digested overnight with NdeI and HindIII restriction enzymes at 37° C. pPRONde vector was then treated for an hour with Calf intestinal alkaline phosphatase (New England BioLabs, Ipswich, Mass.) according to the manufacturer's instruction and gel-purified using Qiagen Gel Extraction kit. PCR products digested with NdeI and HindIII were heated at 75° C. for 30 minutes to inactivate the restriction enzymes and used directly in a Quick ligation reaction (New England Biolabs) with gel-purified vector. After a 5-minute ligation the reaction mix was subjected to buffer exchange with the Qiagen PCR purification kit and 1 μl ligation reaction was used for transformation of electrocompetent E. coli DH10B cells. The transformed cells were plated on LB plates supplemented with 25 μg/ml kanamycin and resulting colonies were tested for the presence of panD genes.

Positive clones were sequenced to verify accuracy and retransformed into E. coli 11303 ΔldhA ΔpanC-D KIfld. Resulting clones were used for biotransformations and aspartate decarboxylase enzyme assays. SEQ ID NO: 38 and 39 depict the nucleotide and protein sequences, respectively, of the aspartate decarboxylase gene of C. acetobutylicum (CapanD). SEQ ID NO: 40 and 41 depict the nucleotide and protein sequences, respectively, of the aspartate decarboxylase gene of S. avermitilis (SapanD).

For biotransformations, the cells carrying pPROCapanD and pPROSapanD plasmids were grown in 2YT medium supplemented with 25 μg/ml kanamycin to $OD_{600}$~0.6-0.8 and induced with 1 mM IPTG for 6 hours. After induction the cells were pelleted, and resuspended to an $OD_{600}$ of ~4 either in M9 medium supplemented with 10 g/L glucose, 100 mM MOPS pH 8.0, 100 μM pyridoxine HCL, and 10 μM pantothenate or in M9 medium without nitrogen supplemented with 0.4 g/L glucose, 20 mM aspartate, 100 mM MOPS and 10 μM pantothenate. The biotransformation was performed in 1 ml medium in 14 ml Falcon tubes (Catalog number 2059) at 37° C., 225 rpm, for 20 hours. At the end of the biotransformation the cells were pelleted, the supernatants were acidified by addition of formic acid to 5%, filtered and analyzed by HPLC as described in Example 4 for production of beta-alanine from glucose alone or both glucose and aspartate.

As shown in Table 2, the production of beta-alanine from glucose alone was about 2 mM. The addition of aspartate to the biotransformation medium increased production of beta-alanine 2-3-fold.

TABLE 2

Production of beta-alanine by aspartate decarboxylases

| Plasmid | Medium | beta-alanine (mM) |
|---|---|---|
| pPROCapanD | Glucose | 2.1 |
| pPROSapanD | Glucose | 1.9 |
| pPROCapanD | Glucose + aspartate | 7.6 |
| pPROSapanD | Glucose + aspartate | 4.9 |

Aspartate decarboxylase activity in crude extracts was assayed by measuring the conversion of aspartate to beta-alanine. The cells carrying plasmids pPROEcpanD, pPROCapanD and pPROSapanD were grown in 2YT medium to $OD_{600}$~0.4-0.6 and induced with 1 mM IPTG and 0.2% arabinose for 6 hours. After induction the cells were pelleted and resuspended in 50 mM HEPPS (pH=8.0) buffer. The cells were disrupted using a French press. The standard reaction mixture contained 1.2 mM aspartate, 50 mM HEPPS (pH=8.0) and 0.4 mg of crude extract in a final volume of 1 mL. After incubation at 37° C., 50 μl of the reaction mixture was removed at timed intervals and quenched with 150 μl of stop solution (10% formic acid). Precipitated protein was removed by centrifugation, and the beta-alanine in each sample was quantified as described.

The specific activities of the aspartate decarboxylase activities in the crude extracts are shown in Table 3.

TABLE 3

Activity of aspartate decarboxylase in crude extracts

| Plasmid | Specific activity (U/mg[a]) |
|---|---|
| pPROEcpanD | 0.004 |
| pPROSapanD | 0.074 |
| pPROCapanD | 0.048 |

[a]1 U = 1 μmol/min

By replacing the p15a origin of replication of plasmid pPROSapanD, which has an average copy number per cell of 15, with an origin of replication from ColE1, which has an average copy number per cell of 30~50, to generate pCECSapanD, the specific activity of the aspartate decarboxylase in cell extracts increased to 0.54 U/mg.

EXAMPLE 8

Production of 3-HP by Cells Expressing panD, BAAT and 3-HP Dehydrogenase

This example describes methods used to produce 3-HP in vivo, by expressing exogenous aspartate decarboxylase, beta-alanine aminotransferase, and 3-HP dehydrogenase in the cell. Although particular enzyme sequences were used, one skilled in the art will appreciate that other such sequences known in the art or disclosed herein can be used.

Cells expressing an exogenous panD gene (SEQ ID NO: 40), exogenous BAAT5-9 gene (SEQ ID NO: 18), and exogenous PpmmsB31 gene (SEQ ID NO: 29), either integrated into the chromosome or present in one or more plasmids, are capable of producing 3-HP from glucose (FIG. 1). In one example of such cells, the host with the BAAT5-9-PpmmsB31 genes integrated into the chromosome is transformed with plasmid pCECSapanD. The host is derived from E. coli strain ATCC 11303 (a B strain) and additionally carries the genetic markers Δpan(C-D) ΔldhA KIfld ΔpoxB.

Transformants were grown in LB medium plus chloramphenicol to maintain the plasmid for 6 h at 30° C. then diluted 100-fold into Overnight Express medium (Novagen/EMD Biosciences, Madison Wis.) as described by the manufacturer except the carbon source (Solution 1 in the Overnight Express kit) is replaced by 0.1% (w/v) glucose, 2% L-arabinose, and additionally has 30 μg/ml chloramphenicol, 20 μM $Ca^{2+}$ pantothenate, and 1 mM IPTG. The cells were grown at 30° C. for approximately 18 hours, then 0.25-ml portions were diluted with 0.75 ml of Biotransformation Medium (M9 salts, 0.1 M MOPS, pH 8.0, 133 μM pyridoxine, 2.67% glucose, 13.3 mM $NaHCO_3$) and incubation continued at 30° C. for 23 hours. The culture supernatant was recovered by centrifugation, and acidified with 0.05 volumes of 90% formic acid (final concentration ~1 M).

3-HP in the supernatant was quantified by LC/MS as described in WO 2005/118719 A2. Briefly, chromatography was performed on a Waters 2690 liquid chromatography system using a 2.1 mm×250 mm Phenomenex Aqua $C_{18}$ reversed-phase chromatography column with isocratic elution at 45° C. using 1% methanol:aqueous containing 0.1% (v/v) formic acid as the mobile phase at a flow rate of 0.18 ml/min. Parameters for the Micromass ZQ quadrupole mass spectrometer operating in negative, electrospray ionization mode (-ESI) were set as the following; capillary: 2.0 kV; cone: 25 V; extractor: 4 V; RF lens: 1 V; source temperature: 120° C.; desolvation temperature: 380° C.; desolvation gas: 600 L/h; cone gas: Off; low mass resolution: 15.0: high mass resolution: 15.0; ion energy: 0.2; multiplier: 650. A selected ion monitoring MS parameter was set up to allow selection of m/z 89, corresponding to the deprotonated molecular ion. [M–H]$^-$, of 3-HP.

Cells carrying the aspartate decarboxylase gene on pCEC-SapanD, and with BAAT and 3-HP dehydrogenase genes integrated in the chromosome under the expression control of the synthetic P$_{lac/ara}$ promoter, accumulated 2.7 g/L 3-HP.

EXAMPLE 9

Effect of Acetate and Pyruvate on Beta-Alanine Aminotransferase

This example describes methods used to determine the effect of acetate and pyruvate on the biological activity of beta-alanine aminotransferase, as determined by 3-HP production. Acetate and pyruvate are natural products of *E. coli* metabolism, and in some examples it is desirable to reduce or eliminate them because they can drain precursors and inhibit enzymes in the 3-HP pathway.

Acetate reduced the in vivo biological activity of BAAT under both anaerobic and aerobic conditions. A culture of *E. coli* 11303 Δpta ΔadhE ΔfrdABCD ΔldhA Δpan(C-D) ΔpoxB INT(BAAT5-9/PpmmsB31) carrying the vector pCEC/SapanD was grown in LB media with chloramphenicol at 30° C. This culture was used to inoculate 20 mL modified Overnight Express media (Novagen) to an initial OD$_{600}$ of 0.05 in a 125 mL flask. Modification to the media included the replacement of Solution 1 with glucose at a concentration of 0.1% and arabinose at 2%, and addition of 20 uM Ca$^{2+}$ pantothenate, 25 ug/mL chloramphenicol, 100 uM pyridoxine-HCl and 1 mM IPTG. After growth in induction media for 17 hours, the OD$_{600}$ was 8.4. A total of 32,500 OD units (OD/ml multiplied by ml) were spun down and resuspended in 7.313 mL of either glucose or beta-alanine biotransformation media. Glucose biotransformation consisted of M9 salts, 100 mM MOPS pH 8, 1% glucose, 500 uM IPTG, and 50 uM pyridoxine-HCl. Beta-alanine biotransformation medium contained 16 mM beta-alanine in addition to the components of glucose biotransformation medium.

For aerobic biotransformations, 900 uL of the resuspended culture was aliquoted to a 14 mL Falcon tube and the volume was brought to 1 mL with water and/or sodium acetate (pH 7). For anaerobic biotransformations, 1.35 mL of the resuspended culture was aliquoted to a 1.8 mL glass vial and the volume was brought to 1.5 mL with water and/or sodium acetate (pH 7). Final concentrations of sodium acetate added were 0, 20 mM, and 100 mM, and biotransformation incubations were al 30° C. with shaking at 225 rpm. Samples were obtained after 3 hours of biotransformation for aerobic cultures from beta-alanine, after 6.5 hours for anaerobic cultures from beta-alanine and aerobic cultures from glucose, and after 28 hours for anaerobic cultures from glucose. Culture supernatants were acidified with 0.05 volumes of 90% formic acid, centrifuged, filtered, and analyzed for 3-HP production as described in Example 8.

Under aerobic conditions, 20 mM acetate caused a 22% reduction in 3-HP from beta-alanine and a 28% reduction from glucose. 100 mM acetate caused a 47% reduction in 3HP from beta-alanine and a 52% reduction from glucose under the same conditions (Table 3). The reduction in 3-HP seen under anaerobic conditions ranged from 8-29% and may have been less due to the presence of acetate as a natural fermentation product in all cultures, including the control without added acetate. Although this biotransformation was performed in a strain with both the poxB and pta genes deleted, acetate production is still observed under certain culture conditions.

TABLE 4

Effect of acetate on 3-HP production

| Substrate | Condition | Acetate added (mM) | 3-HP produced (mg/L) |
|---|---|---|---|
| beta-alanine | Aerobic | 0 | 180 |
| | | 20 | 140 |
| | | 100 | 95 |
| | anaerobic | 0 | 71 |
| | | 20 | 65 |
| | | 100 | 61 |
| glucose | aerobic | 0 | 88 |
| | | 20 | 63 |
| | | 100 | 42 |
| | anaerobic | 0 | 38 |
| | | 20 | 30 |
| | | 100 | 22 |

The effect of acetate on the in vitro biological activity of BAAT enzymes in cell extracts was also measured using a coupled assay in which the malonyl semialdehyde product of the reaction catalyzed by BAAT was reduced by a 3-HP dehydrogenase. An extract of cells carrying the integrated BAAT5-9/PpmmsB31 was made by resuspending cells collected by centrifugation with Bugbuster (EMD/Novagen, Madison Wis.) as described by the manufacturer. Reaction mixtures of final volume 200 µl were formed in wells of a Costar 3635 UV-transparent 96-well flat bottom plate (Corning Incorporated, Corning N.Y.) and contained 50 mM K phosphate, pH 8.0, 100 µM pyridoxal phosphate, 7.5 mM alpha-ketoglutarate, 20 mM beta-alanine, 1 mM NADH, 0.4 mg cell extract protein. The progress of the reaction was monitored as the decrease in A$_{340}$ due to oxidation of the NADH. The effect of acetate or pyruvate was determined by adding up to 20 mM of either compound (as the neutral Na$^+$ salt).

Using this in vitro assay, the activity of the BAAT-3-HP dehydrogenase system was reduced by approximately 50% in the presence of 10 mM acetate or pyruvate.

Based on these, observations, reducing the presence of acetate or pyruvate when producing 3-HP in vivo by a cell expressing BAAT increases the production of 3-HP.

EXAMPLE 10

Host Mutations that Increase 3-HP Production by Reducing Acetate Production

This example describes methods of reducing acetate production, thereby increasing 3-HP production, for example in a cell expressing exogenous BAAT.

The results obtained in Example 9 indicate that 3-HP production is increased in when acetate production is reduced or absent. This can be accomplished by fermentation process controls, such as described in Vemuri et al. (*Appl. Environ. Microbiol.* 72:3653-61, 2006), or by using strains in which the production of acetate is reduced due to the absence of genes encoding enzymatic activities that catalyze the production of acetate, or a combination of both approaches.

Any method of reducing acetate production, whether through genetic manipulation or through control of media and/or growth conditions, or both, could increase 3-HP production from any pathway utilizing the beta-alanine aminotransferase. One method of reducing acetate production by an E. coli strain is to delete the poxB gene, which encodes for pyruvate oxidase. Pyruvate oxidase metabolizes pyruvate to acetate and $CO_2$ and is primarily expressed in cultures under stress or in stationary phase under aerobic conditions. The other major pathway to acetate production is the ack-pta pathway from acetyl CoA, which is primarily active under anaerobic conditions.

The following example illustrates a method whereby a gene in E. coli, such as the poxB gene, can be disrupted. The following primers are used to amplify the FRT-flanked kanamycin marker from plasmid pKD4 (Datsenko and Wanner, Proc. Natl. Acad. Sci. USA 97:6640-5, 2000): 5'-TAAACT-TGTTACCGTTATCACATTCAGGAGATG-GAGAACCATGAAACAAGTGTAGGCTG-GAGCTGCTTC-3' (poxBkoF; SEQ ID NO: 42), and 5'-TCATGGCATGTCCTTATTATGACGG-GAAATGCCACCCTTTTTACCTTAG-CATATGAATATCCTCCTTAG-3' (poxBkoR; SEQ ID NO: 43).

The amplification was done using rTth DNA polymerase XL (Applied Biosystems) as per the manufacturer's instructions, using eight cycles with an annealing temperature of 52° C. and 22 cycles with an annealing temperature of 60° C. and a 2 minute extension at 68° C. The amplification product was gel purified (Qiagen), digested for 3 hours with restriction endonuclease DpnI, and cleaned using a Qiagen PCR purification column. Purified DNA (100 ng) was transformed into BW25115 competent cells carrying the induced Red helper plasmid pKD046 (Datsenko and Wanner, 2000) and transformed cells were plated on LB media containing 25 μg/mL kanamycin.

Resulting colonies were restreaked for purification and single colonies were tested for the desired integration using primers upstream (poxBupF) and downstream (poxBdnR) of the replaced region: 5'-GGGATTTGGTTCTCGCATAATC-3' (poxBupF; SEQ ID NO: 44) and 5'-GTAGGGTCGTCTC-CGTAAAC-3' (poxBdnR; SEQ ID NO: 45).

A P1 phage lysate was made from the BW25113Δ poxB:: kan strain and used to transfer the mutation into the E. coli ATCC11303 carrying Δpta ΔadhE ΔfrdABCD ΔldhA Δpan (C-D). The kanamycin marker was removed according to the procedures outlined in Datsenko and Wanner (2000), with the exception that the pCP20 transformants were selected at 30° C. in liquid media containing carbenicillin and were purified twice non-selectively at 42° C.

Biotransformations from glucose to 3-HP were conducted in shake flasks to test the effect of the ΔpoxB deletion. Two replications each of the strains without and with ΔpoxB carrying the vector pPRONde/CapanD/BAAT5-9/PpmmsB31 were grown in LB media with kanamycin. These cultures were used to inoculate 15 mL 2YT media containing 25 μg/mL kanamycin and 10 uM $Ca^{2+}$ pantothenate in a 125 mL flask. Cells were induced at $OD_{600}$ of 0.53 with 1 mM IPTG and 0.2% arabinose for 6 hours. A total of 4.000 OD units (OD/ml multiplied by ml) was spun down for each culture and was resuspended in 1 mL of biotransformation media, consisting of M9 salts, 100 mM MOPS, pH 8, 1% glucose, 500 uM IPTG, and 100 uM pyridoxine-HCl. Both induction and biotransformation cultures were grown at 30° C. with shaking at 225 rpm. Samples of supernatant taken after 22.5 hours were acidified with 0.05 volumes of 90% formic acid, centrifuged, filtered and analyzed for 3-HP as described in Example 8. Non-acidified supernatant was analyzed for organic acids on a BioRad Aminex HPX 87H ion exchange column (BioRad cat#125-0140), run at 60° C. 0.6 ml/min flow rate with 0.01 N sulfuric acid as the system mobile phase. Acetic acid detection was by refractive index and quantitated against a known concentration standard.

The strains with ΔpoxB showed a 25% increase in 3-HP per OD compared to the control without the ΔpoxB, and produced no detectable acetate compared to 0.64 g/L acetate produced by the control. Thus reducing the metabolic production or presence of acetate leads to increased production of 3-HP by the pathway that involves BAAT, such as a increase, of at least 20%, or at least 25%.

Alternative genetic approaches can be used to reduce the production of acetate, such as by deletion of the pta and/or ack genes.

EXAMPLE 11

Host Mutations that Increase 3-HP Production by Increasing Precursors or Reducing Competing Pathways This example describes additional or alternative methods by which 3-HP production can be increased, for example in a cell expressing exogenous BAAT. Production of 3-HP can be increased by increasing the availability of precursors in the pathways or reducing the drainage of intermediates into other metabolic products.

ppc, phosphoenol pyruvate carboxylase

The availability of a precursor can be increased, for example, by the choice of promoter. For example, a strain was constructed in which the activity of PEP carboxylase, catalyzing the formation of oxaloacetate from phosphoenol pyruvate and $CO_2$, was increased by placing a synthetic promoter in front of the chromosomally-encoded gene, ppc, that encodes this function. A modification of the method for the insertion of PCR-generated fragments in specific sites in the E. coli genome (Datsenko and Wanner, Proc. Natl. Acad. Soc. USA 97:6640-5, 2000) was used. A novel plasmid, pKDprom, was constructed by insertion of the $P_{lac/ara}$ promoter region of pPRONde into plasmid pKD3 of Datsenko and Wanner.

Plasmid pKDprom carries the chloramphenicol-resistance marker between two FRT regions (to allow excision of the marker by the FLP protein) immediately adjacent to the $P_{lac/ara}$ promoter. This segment comprising the marker and promoter on pKDprom was amplified using the following primers that carried 5' extensions homologous to regions immediately upstream of the ppc gene: 5'-AGGATA-CAGGGCTATCAAACGATAAGATGGGGT-GTCTGGGGTAATGTGTAGGCTGGAGCTGCTTC (SEQ ID NO: 46), and 5'-GAGCATACTGACATTACTACGCAAT-GCGGAATATTGTTCGTTCATATGTAC-CTTTCTCCTCTTTAA (SEQ ID NO: 47). The PCR product was recombined into the ppc site in the E. coli BW 25113 genome by the lambda phage Red recombinase functions as described by Datsenko and Wanner (2000). Insertion was followed by selection for chloramphenicol resistance, and confirmed by PCR.

A strain carrying the artificial promoter and chloramphenicol resistance cassette in front of the ppc gene is designated as KIppc::cam, and strains carrying the artificial promoter before the ppc gene, from which the chloramphenicol-resistance marker was excised, are designated KIppc. The KIppc:: cam was transferred by P1 phage transduction into E. coli ATCC 11303 carrying Δpta ΔadhE ΔfrdABCD ΔldhA Δpan (C-D) ΔpoxB 2×INT(BAAT5-9/Ppmmsb31) which contains two copies of the improved beta-alanine aminotransferase (SEQ ID NO: 18) and *P. putida* 3-HP dehydrogenase (SEQ ID NO: 29) integrated into the genome. The resistance markers were resolved from the KIppc strain, and it was transformed with the vector pCEC/SapanD. This strain was compared to the control strain without the KIppc marker in a biotransformation measuring the production of 3-HP from glucose.

Cultures grown in LB media containing chloramphenicol were used to inoculate 9 mL modified Overnight Express media (Novagen) to an initial OD of 0.05-0.07 in a 125 mL flask. Modification to the media included the replacement of Solution 1 with glucose at a concentration of 0.1% and L-arabinose at 2%, and addition of 20 µM $Ca^{2+}$ pantothenate, 25 µg/mL chloramphenicol, 5 µM pyridoxine-HCl, and 10 mM $NaHCO_3$. IPTG was added to a concentration of 1 mM after 2 hours of growth. After growth in induction media for 19 hours. $OD_{600}$ ranged from 8.3 (for the KIppc strain) to 13.8 (control). A total of 32,000 OD units of each strain was centrifuged and resuspended in 8 mL of biotransformation media. Biotransformation media consisted of M9 salts, 100 mM MOPS pH 8, 1% glucose, 500 uM IPTG, 5 uM pyridoxine-HCl, and 10 mM $NaHCO_3$. Both induction and biotransformation cultures were grown at 30° C. with shaking at 225 rpm. Samples were taken after induction and after 7.5 and 23 hours of biotransformation, and were acidified with 0.05 volumes of 90% formic acid, centrifuged, filtered and analyzed for 3-HP, beta-alanine and aspartate as described in Examples 8 and 4.

After 23 hours of biotransformation, all the glucose had been utilized, only trace amounts of beta-alanine remained and the strain carrying the KIppc produced 2.4 times as much 3-HP per OD as the control (Table 5). Therefore, the increase in activity of PEP carboxylase provides increased precursor oxaloacetate for the 3-HP production pathway. Alternative embodiments to increasing formation of oxaloacetate include cloning and expression PEP carboxylase on a plasmid, or cloning and expression pyruvate carboxylase, which converts pyruvate plus $CO_2/HCO_3^-$ to oxaloacetate with the consumption of ATP.

TABLE 5

Effect of increased expression of ppc on 3-HP production

| Strain | Time point (h) | 3-HP (mg/L per OD) | beta-alanine (mg/L per OD) |
|---|---|---|---|
| Control[a] | ONEX[b] | 27 | 114 |
|  | 7.5 | 38 | 30 |
|  | 23 | 92 | 1 |
| KIppc | ONEX | 41 | 126 |
|  | 7.5 | 40 | 84 |
|  | 23 | 218 | 0.8 |

[a]*E. coli* ATCC 11303 Δpta ΔadhE ΔfrdABCD ΔldhA Δpan(C-D) ΔpoxB 2XINT(BAAT5-9/Ppmmsb31/pCECSapanD
[b]ONEX = 3-HP and beta-alanine present in supernatants of cultures in Overnight Express before centrifugation.

aspC, Aspartate Aminotransferase

Another example of a genetic construct whereby the availability of a precursor is increased, is a strain in which the activity of aspartate aminotransferase, catalyzing the formation of aspartate from oxaloacetate and glutamate (FIG. 1), was increased by placing a synthetic promoter in front of the chromosomally-encoded gene, aspC, that encodes this function. The segment comprising the chloramphenicol resistance marker and promoter on pKDprom was amplified using the following primers that carried 5' extensions homologous to regions immediately upstream of the aspC gene: 5'-CCCT-GATAGCGGACTTCCCTTCTGTAACCAT-AATGGAACCTCGTCGTGTAGGCTGGAGCTGCTTC (SEQ ID NO: 48), and 5'-GCCCAGAATCGGGTCGGCAG-GAGCGGCGGTAATGTTCTCAAACATATG-TACCTTTCTCCTCTTTAA (SEQ ID NO: 49).

The PCR product was recombined into the aspC site in the *E. coli* BW 25113 genome by the lambda phage Red recombinase functions as described by Datsenko and Wanner (2000). Insertion was followed by selection for chloramphenicol resistance, and confirmed by PCR. A strain carrying the artificial promoter and chloramphenicol resistance cassette in front of the aspC gene is designated as KIaspC::cam, and trains carrying the artificial promoter before the aspC gene, from which the chloramphenicol-resistance marker was excised, are designated KIaspC. The KIaspC::cam was transferred by P1 phage transduction into *E. coli* ATCC 11303 carrying ΔldhA Δpan(C-D) KIppc 2×INT(BAAT5-9/Ppmmsb31) which contains two copies of the improved beta-alanine aminotransferase (SEQ ID NO: 18) and *P. putida* 3-HP dehydrogenase (SEQ ID NO: 29) integrated into the genome. The resistance markers were resolved from the KIaspC strain, and it was transformed with the vector pCEC/SapanD. This strain was compared to the control strain without the KIaspC marker in a biotransformation measuring the production of 3-HP from glucose.

Cultures grown in LB media containing chloramphenicol were used to inoculate 7 mL modified Overnight Express media (Novagen). Modification to the media included the replacement of Solution 1 with glucose at a concentration of 0.1% and L-arabinose at 2%, and addition of 10 µM $Ca^{2+}$ pantothenate, 30 µg/mL chloramphenicol, and 5 µM pyridoxine-HCl. IPTG was added to a concentration of 1 mM after 3 hours of growth. After growth in induction media for 19 hours, 2.5 ml of each culture was diluted with 7.5 ml of biotransformation media consisting of M9 salts. 100 mM MOPS pH 8, 1% glucose, 100 uM pyridoxine-HCl. Both induction and biotransformation cultures were grown at 30° C. with shaking at 225 rpm. Samples were taken after 21 hours of biotransformation and were acidified with 0.05 volumes of 90% formic acid, centrifuged, filtered and analyzed for 3-HP as described in Example 8.

The strain with the KIaspC produced 441 mg/L.OD, a 2.5-fold increase over the amount of 175 mg/L.OD produced by the control strain. Therefore the increase in activity of aspartate aminotransferase provides increased precursor aspartate for the 3-HP production pathway. Alternative embodiments whereby production of aspartate can be increased include expressing aspartate aminotransferase (for example on a plasmid).

gltA, Citrate Synthase

Expression of citrate synthase was modulated to elevate the levels of oxaloacetate available as substrate for the aspartate aminotransferase reaction, of acetyl-CoA to act as a positive activator of pyruvate carboxylase and/or PEP carboxylase, and to reduce the amount of carbon that is lost to carbon dioxide in the citric acid cycle. The production of citrate synthase was reduced by changing the ATG translational start codon to GTG and the ribosomal binding site to a less ideal sequence for *E. coli*, but can also be done using other mutations to these regions, mutations in the promoter or coding regions, incorporation of rare codons or secondary structure, or RNA interference technology. The mutations used in this example, shown underlined below, were incorporated in the downstream primer used in the Wanner gene knockout technique (Datsenko and Wanner, 2000). The forward primer (gltAKDF) was designed so that once the resistance marker was resolved, the remaining "scar" replaced an equivalent number of nucleotides in the upstream region. This region did not contain any other known genes and is downstream of the predicted gltA promoter. 5'-CTGTACCCAGGTTTTC-CCCTCTTTCACAGAGCGGCGAGC-CAAATAAAAAGTGTAGGCTGGAGCTGCTTC-3' (gl-tAKDF; SEQ ID NO: 50), and 5'-TCAACAGCTGTATCCCCGTTGAGGGT-GAGTTTTGCTTTTGTATCAGCCACATGAATATCC GCCTTAGTTC-3' (gltAKDR; SEQ ID NO: 51).

SEQ ID NO: 52 is the resulting sequence of the of modified gltA locus (KDgltA) in the resolved attenuated strain.

The gltAKDF and gltAKDR primers were used to amplify the FRT-flanked kanamycin marker from plasmid pKD4 (Datsenko and Wanner, 2000). The amplification was done using rTth DNA polymerase XL (Applied Biosystems) as per the manufacturer's instructions, using eight cycles with an annealing temperature of 52° C. and 22 cycles with an annealing temperature of 60° C., and a 2.25 minute extension at 68° C. The amplification product was gel purified (Qiagen), digested for 2 hours with restriction enzyme DpnI, and cleaned using a Qiagen PCR purification column. Purified DNA (100 ng) was transformed into BW25115 competent cells carrying the induced Red helper plasmid pKD046 and transformed cells were plated on LB media containing 25 µg/mL kanamycin.

Resulting colonies were restreaked for purification and single colonies were tested for the desired integration using primers upstream (gltAupF; 5'-GATTCGCCATTTATTCGT-CATC-3'; SEQ ID NO: 53) and downstream (gltAdwnR; 5'-CTGGGTCAAAGGTGAACAC-3'; SEQ ID NO: 54) of the replaced region, or with the upstream primer and a primer specific to the altered nucleotides (gltAtestR; 5'-GTTTTGCTTTTGTATCAGCCACA-3'; SEQ ID NO: 55). Using an annealing temperature of 59.5° C., the gltAupF/gltAtestR primers failed to produce a PCR product with wild-type gltA template but produced a product of the expected size with the purified transformants.

A P1 phage lysate was then made of the modulated gltA strain and was used to transfer the mutation into *E. coli* ATCC11303 carrying Δpta ΔadhE ΔfrdABCD ΔldhA Δpan(C-D) ΔpoxB and one copy of the BAAT5-9/PpmmsB31 integration. The kanamycin marker was resolved according to the procedures outlined in Datsenko and Wanner (2000), with the exception that the pCP20 transformants were selected at 30° C. in liquid media containing carbenicillin and were purified twice non-selectively at 42° C.

Biotransformations from glucose to 3HP were conducted in shake flasks to test the effect of the gltA modulation (KDgltA). Cultures of the strains 11303 carrying Δpta ΔadhE ΔfrdABCD ΔldhA Δpan(C-D) ΔpoxB INT and 11303 carrying Δpta ΔadhE ΔfrdABCD ΔldhA Δpan(C-D) ΔpoxB INT KDgltA, both carrying the vector pCEC/SapanD, were grown in LB media with chloramphenicol. These cultures were used to inoculate 10 mL modified Overnight Express media (Novagen) to an initial OD of 0.05-0.10 in a 125 mL flask. Modification to the media included the replacement of Solution 1 with glucose at a concentration of 0.1% and arabinose at 2%, and addition of 20 µM $Ca^{2+}$ pantothenate, 25 µg/mL chloramphenicol, 50 µM pyridoxine-HCl, and 10 mM $NaHCO_3$. IPTG at a concentration of 1 mM was added after 1.25 hours of growth. After growth in induction media for 18 hours. $OD_{600}$ ranged from 4.5 (KDgltA) to 11.2 (control). A total of 32,000 OD units (OD/ml multiplied by ml) was centrifuged and resuspended in 8 mL of biotransformation media. Biotransformation media consisted of M9 salts, 100 mM MOPS pH 8, 1% glucose, 500 µM IPTG, 50 µM pyridoxine-HCl, and 10 mM $NaHCO_3$. Both induction and biotransformation cultures were grown at 30° C. with shaking at 225 rpm. Samples were taken after induction and after 6 and 24 hours of biotransformation, and were analyzed for 3HP and beta-alanine as described in Examples 8 and 4.

The strain with the modulated KDgltA showed a 2.5 to 3.7-fold increase in 3-HP per OD compared to the control (Table 6), indicating that reducing metabolic flow through the citrate synthase step is beneficial for the production of 3-HP.

TABLE 6

Effect of modulation of citrate synthase production

| Strain | Time point (h) | 3-HP (mg/L per OD) | beta-alanine (mg/L per OD) |
|---|---|---|---|
| Control[a] | ONEX[b] | 26 | 106 |
|  | 6 | 22 | 57 |
|  | 24 | 90 | 0 |
| KDgltA | ONEX[b] | 95 | 159 |
|  | 6 | 77 | 34 |
|  | 24 | 222 | 22 |

[a]*E. coli* ATCC 11303 Δpta ΔadhE ΔfrdABCD ΔldhA Δpan(C-D) ΔpoxB INT(BAAT5-9/Ppmmsb31)/pCECSapanD
[b]ONEX = 3-HP and beta-alanine present in supernatants of cultures in Overnight Express before centrifugation.

atpFH, $F_1$ and $F_0$ Components of the $F_0F_1$-ATP Synthase

The atpFH genes encode two proteins that couple the $F_1$ and $F_0$ components of the $F_0F_1$-ATP synthase. A strain with a deletion of these two genes is unable to synthesize ATP through proton translocation through the complex and instead possesses a cytoplasmic $F_1$-ATPase. ATP mutants are dependent on substrate level phosphorylation to regenerate ATP from ADP. Flux is increased through both glycolytic pathway to produce ATP via phosphotransacetylase (acetate production) and through the TCA cycle to produce GTP/ATP via succinyl-CoA synthase. The increased flux through these pathways leads to increased production of NADH. The cytoplasmic ATPase activity provides ADP for glycolysis, and the decreased growth rate of the mutant reduces pyruvate utilization for cell growth. Causey et al. (*Proc. Natl. Acad. Sci. USA* 101(8): 2235-40, 2004) showed that a deletion of the atpFH gene (ΔatpFH) led to pyruvate accumulation because the increase in glycolytic flux was greater than the capacity of the acetate pathway.

In the aspartate pathway to 3-HP, the combination of the ΔatpFH mutation with overexpression of pyruvate or PEP carboxylase would increase carbon flow from pyruvate to oxaloacetate and the NADH could be used by the 3-HP dehydrogenase to drive the pathway. Other mutations that increase the pool of available pyruvate are ΔldhA, Δack-pta, ΔfrdABCD, ΔpoxB, and ΔadhE. The atpFH deletion can be used in combination with the citrate synthase attenuation to reduce flux through the TCA cycle, although NADH itself is an allosteric inhibitor of citrate synthase.

The following primers were used to construct the deletion of the atpFH gene: 5'-GAGCAATATCAGAACGTTAAC-TAAATAGAGGCATTGTGCTGTGAATCT-TGTGTAGGCTGGAGCTGCTTC-3' (atpFHkoF; SEQ ID NO: 56), and 5'-CGCTGATTTCGGTGGAATTCAGTTG-CATGCTCCAGTCCCCTTAAGACTG-CATATGAATATCCTCCTTAG-3' (atpFHkoR; SEQ ID NO: 57). These primers were used to amplify the FRT-flanked kanamycin marker from plasmid pKD4 (Datsenko and Wanner, 2000). The amplification was done using rTth DNA polymerase XL (Applied Biosystems) as per the manufacturer's instructions, using eight cycles with an annealing temperature of 52° C. and 22 cycles with an annealing temperature of 60° C., and a two minute extension at 68° C. The amplification product was gel purified (Qiagen), digested for three hours with restriction endonuclease DpnI, and cleaned using a Qiagen PCR purification column. Purified DNA (100 ng) was transformed into BW25115 competent cells carrying the induced lambda Red helper plasmid pKD046 and transformed cells were plated on LB media containing 25 ug/mL kanamycin. Resulting colonies were restreaked for purification and single colonies were tested for the desired integration using primers upstream (atpFHupF: 5'-CTCTGCTGCG-TACTCAGTTC-3'; SEQ ID NO: 58) and downstream (atpF-HdnR; 5'-GATCATTTCACCCTGCATACAATC-3'; SEQ ID NO: 59) of the replaced region. A P1 phage lysate was then made from the BW25113ΔatpFH strain and was used to transfer the mutation into E. coli ATCC 11303 Δpta ΔadhE ΔfrdABCD ΔldhA Δpan(C-D). The kanamycin marker was resolved according to the procedures outlined in Datsenko and Wanner (2000), with the exception that the pCP20 transformants were selected at 30° C. sequentially in liquid and on solid media containing ampicillin and were purified twice non-selectively at 42° C.

Biotransformations from glucose to 3HP were conducted in shake flasks to test the effect of the atpFH knockout. Cultures of the strains 11303 Δpta ΔadhE ΔfrdABCD ΔldhA Δpan(C-D) (control) and 11303 Δpta ΔadhE ΔfrdABCD ΔldhA Δpan(C-D) ΔatpFH, both carrying the vectors pPRONde/SapanD/BAAT5-9/PpmmsB31 and pPRONde/CapanD/BAAT5-9/PpmmsB31 were grown in LB media with kanamycin, allowing more time for growth of the slower-growing ΔatpFH strains. Cultures were used to inoculate 20 mL 2YT media containing 25 μg/mL kanamycin and 10 μM Ca$^{2+}$ pantothenate in a 125 mL flask. Cells were induced at OD$_{600}$ of 0.29 (ΔatpFH) or 0.65 (control) with 0.1 mM IPTG and 0.2% arabinose for both 6 hours and 22.5 hours. 4,000 OD units (OD/ml multiplied by ml) was spun down and resuspended in 1 mL of biotransformation media. Biotransformation media consisted of M9 salts, 100 mM MOPS pH 8.1% glucose, 500 μM IPTG, and 50 μM pyridoxine-HCl. Both induction and biotransformation cultures were grown at 30° C. with shaking at 225 rpm. Samples were taken after approximately 23 hours and were analyzed for 3HP as described in Example 8.

The strain carrying the ΔatpFH showed a 2 to 3.4-fold increase in 3-HP per OD compared to the control (Table 7).

TABLE 7

Effect of ΔatpFH on 3-HP production

| Strain | panD | Time point (h) | 3-HP (mg/L per OD) |
|---|---|---|---|
| Control[a] | Ca | 6 | 15 |
| | | 22.5 | 8 |
| | Sa | 6 | 23 |
| | | 22.5 | 23 |
| ΔatpFH | Ca | 6 | 32 |
| | | 22.5 | 16 |
| | Sa | 6 | 60 |
| | | 22.5 | 79 |

[a]E. coli ATCC 11303 Δpta ΔadhE ΔfrdABCD ΔldhA Δpan(C-D)/pPRONde/SapanD/BAAT5-9/PpmmsB31 or pPRONde/CapanD/BAAT5-9/PpmmsB31

Biotransformations were also done to measure the production of beta-alanine from glucose by E. coli 11303 Δpta ΔadhE ΔfrdABCD ΔldhA Δpan(C-D) and 11303 Δpta ΔadhE ΔfrdABCD ΔldhA Δpan(C-D) ΔatpFH strains carrying the plasmid pCEC/SapanD. Cultures grown in LB media with chloramphenicol were used to inoculate 10 mL modified Overnight Express media (Novagen) to an initial OD$_{600}$ of 0.05-0.15 in a 125 mL flask. Modification to the media included the replacement of Solution 1 with glucose at a final concentration of 0.1% and arabinose at 2%, addition of 20 μM Ca$^{2+}$ pantothenate, 25 μg/mL chloramphenicol, 50 μM pyridoxine-HCl, and 10 mM NaHCO$_3$. IPTG at a concentration of 1 mM was added after 1.25 hours of growth. After growth in induction media for 20 hours, ODs ranged from 1.8 (ΔatpFH) to 13.2 (control). 10,000 OD units (OD/ml multiplied by ml) was spun down and resuspended in 2.5 mL of biotransformation medium. Biotransformations were done using 1 and 1.5 mL of resuspended culture in 14 mL Falcon tubes. Biotransformation medium consisted of M9 salts, 100 mM MOPS pH 8, 1% glucose, 500 μM IPTG, 50 μM pyridoxine-HCl, and 10 mM NaHCO$_3$. Both induction and biotransformation cultures were grown at 30° C. with shaking at 225 rpm. Samples were taken after induction and after 24 hours of biotransformation and were analyzed for beta-alanine as described in Example 4.

The 11303Δpta ΔadhE ΔfrdABCD ΔldhA Δpan(C-D) ΔatpFH/pCECSapanD strain showed a 1.4 to 2.2-fold increase in beta-alanine per OD compared to the control (Table 8). Thus deletion of the atpFH genes leads to increased formation of beta-alanine and 3-HP in the presence of the metabolic pathway for 3-HP formation from beta-alanine.

TABLE 8

Effect of ΔatpFH on beta-alanine production

| Strain | Time point (h) | beta-alanine (mg/L per OD) |
|---|---|---|
| Control[a] | ONEX[b] | 113 |
| | 24 | 113 |
| ΔatpFH | ONEX | 247 |
| | 24 | 157 |

[a]E. coli ATCC 11303 Δpta ΔadhE ΔfrdABCD ΔldhA Δpan(C-D)/pCECSapanD
[b]ONEX = beta-alanine present in supernatants of cultures in Overnight Express before centrifugation.

While the effect of mutations designated KIppc, KIaspC, KDgltA, and ΔatpFH were determined individually, and each shown to lead to increased production of 3-HP by cells with aspartate decarboxylase, improved BAAT, and 3-HP dehydrogenase activities, the combination of two or more of these mutations is expected to further increase the amount of 3-HP production by these cells.

EXAMPLE 12

Production of Beta-Alanine

This example describes methods of producing beta-alanine, and cells that can produce beta-alanine. One skilled in the art will appreciate that although particular enzymes are described, the same enzymes from other species can be used (as well as variants of the disclosed enzymes), for example depending on the host cell in which production of beta-alanine is desired.

Beta-alanine can be generated from aspartate, for example in the presence of an aspartate decarboxylase (FIG. 1) in vitro, in vivo (such as in a cell), or combinations thereof. For example, cells (such as a microorganism) producing aspartate can be engineered to make beta-alanine by expressing nucleic acid molecules that encode for an enzyme having aspartate decarboxylase activity in the cell, for example using recombinant technologies. Exemplary aspartate decarboxylase nucleic acid molecules include those shown in SEQ ID NOS: 38 and 40, as well as variants thereof that retain the ability to encode an enzyme that can convert aspartate to beta-alanine (such as a nucleic acid encoding SEQ ID NO: 39 or 41). The cell can also have PEP carboxylase activity or pyruvate carboxylase activity (or both), and aspartate aminotransferase activity to permit the production of aspartate from PEP or pyruvate (or both). Such activity can be endogenous to the cell or exogenous (for example as supplied by an exogeous nucleic acid molecule encoding the peptide).

In a specific example, the cell includes one or more exogenous nucleic acids encoding PEP carboxylase, pyruvate carboxylase, aspartate aminotransferase, and aspartate decarboxylase, wherein expression of at least one of these nucleic acid molecules is controlled by a non-native promoter that increases expression of the nucleic acid molecule. In particular examples, such increased expression increases the amount of beta-alanine produced by the cell, for example an increase of at least 20%. Such cells can also include mutations that increase the available pool of pyruvate, such as a functional deletion of poxB, adhE, atpFH, or combinations thereof. In some examples, the cells also include mutations or nucleic acid molecules that decrease the production of citrate synthase (such as expression of SEQ ID NO: 52).

Methods of producing beta-alanine in vivo can therefore include culturing the disclosed cells under conditions sufficient for producing beta-alanine from aspartate. In a particular example, such methods of making beta-alanine include transfecting a cell with one or more exogenous nucleic acids encoding PEP carboxylase, pyruvate carboxylase, aspartate aminotransferase, and aspartate decarboxylase, and culturing the transfected cell to allow the transfected cell to make beta-alanine. The resulting beta-alanine can be isolated from the cell culture medium or extracted from the cells.

Methods of producing beta-alanine from aspartate in vitro are also provided. For example, conversion of aspartate to beta-alanine can be achieved by contacting aspartate with an enzyme having aspartate decarboxylase activity. Such conversion can also be performed by a combination of in vivo and in vitro methods.

The formation of beta-alanine during fermentation in vivo or in vitro can be analyzed using HPLC (see Example 4) or other methods (see Example 7).

EXAMPLE 13

Production of Malonyl Semialdehyde

This example describes methods of producing malonyl semialdehyde, and cells that can produce malonyl semialdehyde. In particular examples, such methods and cells can serve as a starting point for making 3-HP. One skilled in the art will appreciate that although particular enzymes are described, the same enzymes from other species can be used (as well as variant enzymes), for example depending on the host cell in which production of malonyl semialdehyde is desired.

Malonyl semialdehyde can be generated from beta-alanine via BAAT (FIG. 1) in vitro, in vivo (such as in a cell), or combinations thereof. For example, cells (such as a microorganism) producing beta-alanine (see Example 12) can be engineered to make malonyl semialdehyde by expressing one or more nucleic acid molecules that encode for an enzyme having BAAT activity in the cell, for example using recombinant technologies. Exemplary BAAT nucleic acid molecules include those shown in SEQ ID NOS: 5, 7, 9, 11, 13, 16 and 18 as well as variants thereof that retain the ability to encode an enzyme that can convert aspartate to beta-alanine (such as a nucleic acid encoding SEQ ID NO: 6, 8, 10, 12, 14, 17 or 19).

Methods of producing beta-alanine in vivo can therefore include culturing the disclosed cells under conditions sufficient for producing malonyl semialdehyde from beta-alanine.

In a particular example, such methods of making malonyl semialdehyde include transfecting a cell with one or more exogenous nucleic acids encoding PEP carboxylase, pyruvate carboxylase, aspartate aminotransferase, aspartate decarboxylase, and BAAT, and culturing the transfected cell to allow the transfected cell to make malonyl semialdehyde. The resulting malonyl semialdehyde can be used as a precursor for making other products such as 3-HP. In particular examples, malonyl semialdehyde is isolated from the cell culture medium or extracted from the cells for use.

Methods of producing malonyl semialdehyde from beta-alanine in vitro are also provided. For example, conversion of beta-alanine to malonyl semialdehyde can be achieved by contacting beta-alanine with an enzyme having BAAT activity. Such conversion can also be performed by a combination of in vivo and in vitro methods.

The formation of malonyl semialdehyde during fermentation in vivo or in vitro can be analyzed using HPLC or the Purpald® aldehyde trapping dye (see Example 1).

EXAMPLE 14

Production of 3-HP from Beta-Alanine

This example describes methods of producing 3-HP, and cells that can produce 3-HP. In particular examples, such methods and cells can serve as a starting point for making derivatives of 3-HP, such as 3-HP esters, 1,3-propanediol, and polymerized 3-HP (see Examples 14-16, respectively). One skilled in the art will appreciate that although particular enzymes are described, the same enzymes from other species can be used (as well as variant enzymes), for example depending on the host cell in which production of 3-HP is desired.

3-HP can be generated from beta-alanine via malonyl semialdehyde (FIG. 1) in vitro, in vivo (such as in a cell), or combinations thereof. For example, cells (such as a microorganism) producing malonyl semialdehyde (see Example 13) can be engineered to make 3-HP by expressing one or more nucleic acid molecules that encode for an enzyme having 3-HP dehydrogenase activity in the cell, for example using recombinant technologies. Exemplary 3-HP dehydrogenase nucleic acid molecules include those shown in SEQ ID NOS: 20, 22, 26 and 29 as well as variants thereof that retain the ability to encode an enzyme that can convert aspartate to beta-alanine (such as a nucleic acid encoding SEQ ID NO: 21, 23, 27, or 31).

Methods of producing 3-HP in vivo can therefore include culturing the disclosed cells under conditions sufficient for producing 3-HP from beta-alanine and malonyl semialdehyde. In a particular example, such methods of making 3-HP include transfecting a cell with one or more exogenous nucleic acids encoding PEP carboxylase, pyruvate carboxylase, aspartate aminotransferase, aspartate decarboxylase, BAAT, and 3-HP dehydrogenase and culturing the transfected cell to allow the transfected cell to make 3-HP. The resulting 3-HP can be used as a precursor for making other products such as 3-HP esters, polymerized 3-HP, and 1,3 propanediol. In particular examples, 3-HP is isolated from the cell culture medium or extracted from the cells for use.

Methods of producing 3-HP from malonyl semialdehyde vitro are also provided. For example, conversion of malonyl semialdehyde to 3-HP can be achieved by contacting malonyl semialdehyde with an enzyme having 3-HP dehydrogenase activity. Such conversion can also be performed by a combination of in vivo and in vitro methods.

The formation of 3-HP during fermentation in vivo or in vitro can be analyzed using the methods disclosed in US 20040076982A1 (herein incorporated by reference as to those methods).

EXAMPLE 15

Producing an Ester of 3-HP

This example describes methods of producing an ester of 3-HP, and cells that can produce an ester of 3-HP. Particular examples of 3-HP esters include, but are not limited to: methyl 3-hydroxypropionate, ethyl 3-hydroxypropionate, propyl 3-hydroxypropionate, butyl 3-hydroxypropionate, or 2-ethylhexyl 3-hydroxypropionate. One skilled in the art will appreciate that although particular enzymes are described, the same enzymes from other species can be used (as well as variant enzymes), for example depending on the host cell in which production of the 3-HP ester is desired.

An ester of 3-HP can be generated from 3-HP. For example, cells or microorganisms producing 3-HP (such as those disclosed in Example 14) can be engineered to make an ester of 3-HP by expressing genes that encode for enzymes having lipase or esterase activity (EC 3.1.1.-).

For example, cells (such as a microorganism) producing 3-HP can be engineered to make an ester of 3-HP by expressing genes that encode for enzymes having lipase or esterase activity. In a particular example, a transformed cell that produces an ester of 3-HP can include one or more nucleic acid sequences (such as an exogenous nucleic acid sequence) that encode a protein having lipase or esterase activity, and in some examples the cell further include one or more nucleic acid sequences that encode a protein having PEP carboxylase activity, pyruvate carboxylase activity, aspartate aminotransferase activity, aspartate decarboxylase activity, BAAT activity, and 3-HP dehydrogenase activity.

Methods of producing a 3-HP ester in vivo can therefore include culturing the disclosed cells under conditions sufficient for producing the 3-HP ester from 3-HP. In a particular example, such methods of making 3-HP esters include transfecting a cell with one or more exogenous nucleic acids encoding PEP carboxylase, pyruvate carboxylase, aspartate aminotransferase, aspartate decarboxylase, BAAT, 3-HP dehydrogenase, and lipase or esterase and culturing the transfected cell to allow the transfected cell to make an ester of 3-HP. The resulting 3-HP ester can be isolated from the cell culture medium or extracted from the cells for use.

Methods of producing an ester of 3-HP from 3-HP in vitro are also provided. Conversion of 3-HP to an ester of 3-HP can be achieved by contacting 3-HP with an enzyme having lipase or esterase activity to form an ester of 3-HP. These conversions can also be performed using a combination of in vivo and in vitro methods.

The formation of an ester of 3-HP during fermentation in vivo or in an in vitro assay can be analyzed using methods described in US 20040076982A1.

EXAMPLE 16

Production of 1,3-propanediol

This example describes methods of producing 1,3-propanediol, and cells that can produce 1,3-propanediol. One skilled in the art will appreciate that although particular enzymes are described, the same enzymes from other species can be used (as well as variant enzymes), for example depending on the host cell in which production of 1,3-propanediol is desired.

1,3-propanediol can be generated from 3-HP (FIG. 1). For example, cells (such as a microorganism) producing 3-HP (such as those disclosed in Example 14) can be engineered to make 1,3-propanediol by expressing nucleic acid molecules that encode for enzymes having aldehyde dehydrogenase (EC 1.2.1.-) and alcohol dehydrogenase (EC 1.1.1.1) activities.

For example, cells (such as a microorganism) producing 3-HP can be engineered to make 1,3-propanediol by expressing genes that encode for enzymes having aldehyde dehydrogenase activity (EC 1.2.1.-) and alcohol dehydrogenase activity (EC 1.1.1.1)). In a particular example, a transformed cell that produces 3-HP can include one or more nucleic acid sequences (such as an exogenous nucleic acid sequence) that encode a protein having aldehyde dehydrogenase activity (EC 1.2.1.-) and alcohol dehydrogenase activity (EC 1.1.1.1), and in some examples the cell further include one or more nucleic acid sequences that encode a protein having PEP carboxylase activity, pyruvate carboxylase activity, aspartate aminotransferase activity, aspartate decarboxylase activity, BAAT activity, and 3-HP dehydrogenase activity.

Methods of producing 1,3-propanediol in vivo can therefore include culturing the disclosed cells under conditions sufficient for producing 1,3-propanediol from 3-HP. In a particular example, such methods of making 1,3-propanediol includes transfecting a cell with one or more exogenous nucleic acids encoding PEP carboxylase, pyruvate carboxylase, aspartate aminotransferase, aspartate decarboxylase, BAAT, 3-HP dehydrogenase, aldehyde dehydrogenase activity (EC 1.2.1.-), and alcohol dehydrogenase activity (EC 1.1.1.1), and culturing the transfected cell to allow the transfected cell to make 1,3-propanediol. The resulting 1,3-propanediol can be isolated from the cell culture medium or extracted from the cells for use.

Methods of producing 1,3-propanediol from 3-HP in vitro are also provided. 3-HP can be converted to 1,3-propanediol by contacting 3-HP with enzymes having aldehyde dehydrogenase activity (EC 1.2.1.-) and alcohol dehydrogenase activity (EC 1.1.1.1). Alternatively, chemical methods of producing 1,3-propanediol from 3-HP in vitro can be used, such as the method disclosed in US 2005/0283029 by Meng, Tsobanakis, and Abraham.

The formation of 1,3-propanediol during fermentation or in an in vitro process can be analyzed using a High Performance Liquid Chromatography (HPLC). The chromatographic separation can be achieved by using a Bio-Rad 87H ion-exchange column. A mobile phase of 0.01N sulfuric acid is passed at a flow rate of 0.6 ml/min and the column maintained at a temperature of 45-65° C. The presence of 1,3-propanediol in the sample can be detected using a refractive index detector (Skraly et al., *Appl. Environ. Microbiol.* 64:98-105, 1998).

EXAMPLE 17

Producing Polymerized 3-HP

This example describes methods of producing polymerized 3-HP, and cells that can produce polymerized 3-HP. One skilled in the art will appreciate that although particular enzymes are described, the same enzymes from other species can be used (as well as variant enzymes), for example depending on the host cell in which production of polymerized 3-HP is desired.

Polymerized 3-HP can be generated from 3-HP (FIG. 1). For example, cells (such as a microorganism) producing 3-HP (such as those described in Example 14) can be engineered to make polymerized 3-HP by expressing nucleic acid molecules that encode for enzymes having esterase activity.

For example, cells producing 3-HP (such as those described in Example 14) can be engineered to make polymerized 3-HP by expressing a gene that encode for an enzyme having esterase activity. In a particular example, a transformed cell that produces polymerized 3-HP can include one or more nucleic acid sequences (such as an exogenous nucleic acid sequence) that encode a protein having esterase activity, and in some examples the cell further include one or more nucleic acid sequences that encode a protein having PEP carboxylase activity, pyruvate carboxylase activity, aspartate aminotransferase activity, aspartate decarboxylase activity, BAAT activity, and 3-HP dehydrogenase activity.

Methods of producing polymerized 3-HP in vivo can therefore include culturing the disclosed cells under conditions sufficient for producing polymerized 3-HP from 3-HP. In a particular example, such methods of making polymerized 3-HP includes transfecting a cell with one or more exogenous nucleic acids encoding PEP carboxylase, pyruvate carboxylase, aspartate aminotransferase, aspartate decarboxylase, BAAT, 3-HP dehydrogenase, and esterase activity, and culturing the transfected cell to allow the transfected cell to make polymerized 3-HP. The resulting polymerized 3-HP can be isolated from the cell culture medium or extracted from the cells for use.

Methods of producing polymerized 3-HP from 3-HP in vitro are also provided. Conversion of 3-HP to polymerized 3-HP can be achieved by contacting 3-HP with an enzyme having esterase activity to form polymerized 3-HP. These conversions can also be performed using a combination of in vivo and in vitro methods.

The formation of polymerized 3-HP during fermentation in vivo or in an in vitro assay can be analyzed using size-exclusion HPLC.

EXAMPLE 18

Peptide Synthesis and Purification

The enzymes disclosed herein, such as PEP carboxylase, pyruvate carboxylase, aspartate aminotransferase, aspartate decarboxylase, BAAT, 3-hydroxypropionate dehydrogenase, lipase, esterase, aldehyde dehydrogenase, and alcohol dehydrogenase (and variants thereof that retain the desired enzymatic activity) can be chemically synthesized by any of a number of manual or automated methods of synthesis known in the art. Such synthesized peptides can be used in an in vitro reaction to produce the desired end product.

For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. (*Solid Phase Peptide Synthesis*, IRL Press: Oxford, 1989).

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5-3 hours at RT.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

---

We claim:

1. An isolated nucleic acid molecule, comprising a nucleic acid sequence encoding a protein having at least 95% sequence identity to the protein sequence shown in SEQ ID NO: 19, wherein the amino acid corresponding to position 3 of SEQ ID NO: 19 is His, the amino acid corresponding to position 24 of SEQ ID NO: 19 is Thr, the amino acid corresponding to position 110 of SEQ ID NO: 19 is Asn, or the amino acid corresponding to position 113 of SEQ ID NO: 19 is Leu, and wherein the protein has beta-alanine aminotransferase (BAAT) activity.

2. The isolated nucleic acid molecule of claim 1, wherein the protein comprises the amino acid sequence shown in SEQ ID NO: 19.

3. The isolated nucleic acid molecule of claim 1 operably linked to a promoter sequence.

4. The isolated nucleic acid molecule of claim 1, wherein the nucleic acid sequence comprises at least 95% sequence identity to the nucleic acid sequence shown in SEQ ID NO: 18.

5. The isolated nucleic acid molecule of claim 1, wherein the nucleic acid sequence comprises SEQ ID NO: 18.

6. A vector comprising the isolated nucleic acid molecule of claim 1.

7. A recombinant nucleic acid molecule comprising the isolated nucleic acid molecule of claim 1.

8. An isolated cell transformed with the recombinant nucleic acid molecule of claim 7.

9. The isolated cell of claim 8, wherein the cell is a prokaryotic cell.

10. The isolated cell of claim 8, wherein the cell is a yeast cell.

11. The isolated cell of claim 8, wherein the isolated nucleic acid sequence comprises a nucleic acid sequence having at least 95% sequence identity to SEQ ID NO: 18, and wherein the cell produces at least 50% more malonyl semialdehyde from beta-alanine than in the presence of a native BAAT nucleic acid sequence.

12. The isolated cell of claim 11, wherein the isolated nucleic acid sequence comprises SEQ ID NO: 18.

13. The isolated cell of claim 11, wherein the cell further comprises an exogenous or an endogenous nucleic acid molecule encoding a 3-HP dehydrogenase and wherein the cell produces 3-hydroxypropionic acid (3-HP).

14. The isolated cell of claim 13, wherein the cell further comprises an exogenous nucleic acid molecule encoding a lipase or esterase and produces an ester of 3-HP.

15. The isolated cell of claim 13, wherein the cell further comprises an exogenous nucleic acid molecule encoding an esterase and produces polymerized 3-HP.

16. The isolated cell of claim 13, wherein the cell further comprises an exogenous or an endogenous nucleic acid molecule encoding an alcohol dehydrogenase, an aldehyde dehydrogenase, or both, and wherein the cell produces 1,3-propanediol.

17. The isolated cell of claim 13, wherein the nucleic acid molecule encoding a 3-HP dehydrogenase encodes a protein having at least 95% sequence identity to SEQ ID NO: 31.

18. The isolated cell of claim 13, wherein the nucleic acid molecule encoding a 3-HP dehydrogenase comprises at least 95% sequence identity to SEQ ID NO: 30.

19. The isolated cell of claim 13, wherein the cell further comprises an exogenous nucleic acid molecule encoding an aspartate decarboxylase.

20. The isolated cell of claim 19, wherein the exogenous nucleic acid molecule encoding an aspartate decarboxylase comprises a nucleic acid sequence that encodes a protein having at least 95% sequence identity to SEQ ID NO: 41.

21. The isolated cell of claim 19, wherein the exogenous nucleic acid molecule encoding an aspartate decarboxylase comprises at least 95% sequence identity to SEQ ID NO: 40.

22. The isolated cell of claim 13, wherein the cell further comprises an exogenous or an endogenous nucleic acid molecule encoding a PEP carboxylase and an exogenous or an endogenous nucleic acid molecule encoding an aspartate aminotransferase.

23. The isolated cell of claim 13, wherein the cell further comprises an exogenous nucleic acid molecule encoding a pyruvate carboxylase.

24. The isolated cell of claim 22, wherein the nucleic acid molecule encoding PEP carboxylase includes a synthetic promoter operably linked to the PEP carboxylase.

25. The isolated cell of claim 22, wherein the nucleic acid molecule encoding aspartate aminotransferase includes a synthetic promoter operably linked to the aspartate aminotransferase.

26. The isolated cell of claim 13, wherein the cell includes a pyruvate oxidase mutation (ΔpoxB) that decreases acetate formation by the cell by at least 20%.

27. The isolated cell of claim 13, wherein the cell includes an alcohol dehydrogenase mutation (ΔadhE) or an adenosine triphosphate (ATP) synthatase B chain and ATP synthatase delta chain mutation (ΔatpFH), and wherein production of 3-HP by the cell is increased by at least 20% as compared to the absence of ΔadhE or ΔaptFH.

28. The isolated cell of claim 13, wherein the cell includes an exogenous nucleic acid molecule comprising at least 95% sequence identity to SEQ ID NO: 52.

29. An isolated cell comprising an exogenous nucleic acid molecule encoding SEQ ID NO: 19, wherein expression of the nucleic acid molecule results an increase in 3-hydroxypropionic acid (3-HP) in the cell of at least 2-fold as compared to 3-HP expression in the cell in the absence of the exogenous nucleic acid molecule.

30. The isolated cell of claim 29, wherein expression of the nucleic acid molecule encoding BAAT results an increase in 3-HP in the cell of at least 2-fold as compared to 3-HP expression in the cell in the presence of an exogenous nucleic acid molecule encoding SEQ ID NO: 4.

31. The isolated cell of claim 8, wherein the cell produces malonyl semialdehyde from beta-alanine.

32. The isolated cell of claim 31, wherein the cell produces 3-HP, a 3-HP ester, polymerized 3-HP, 1,3-propanediol, or combinations thereof.

33. A method for making 3-HP, comprising:
culturing the isolated cell of claim 13 under conditions that permit the cell to produce 3-HP from malonyl semialdehyde.

34. A method for making an ester of 3-HP, comprising:
culturing the cell of claim 14 under conditions that permit the cell to produce the ester of 3-HP from 3-HP.

35. A method for making polymerized 3-HP, comprising:
culturing the cell of claim 15 under conditions that permit the cell to produce the polymerized 3-HP from 3-HP.

36. A method for making 1,3-propanediol, comprising:
culturing the cell of claim 16 under conditions that permit the cell to produce the 1,3-propanediol from 3-HP.

37. A method for making 3-HP, comprising:
purifying malonyl semialdehyde from the cell of claim 8; and
contacting the malonyl semialdehyde with a peptide comprising 3-hydroxypropionate dehydrogenase activity to form 3-HP.

38. A method for making 3-HP, comprising:
transfecting the cell of claim 8 with a nucleic acid molecule encoding a peptide comprising 3-HP dehydrogenase activity; and
culturing the transfected cell to allow the transfected cell to make 3-HP.

39. The method of claim 38, wherein the nucleic acid molecule encoding a peptide comprising 3-HP dehydrogenase activity comprises at least 95% sequence identity to SEQ ID NO: 30.

40. A method for making polymerized 3-HP, comprising:
isolating 3-HP generated using the method of claim 37; and
contacting the 3-HP with a peptide comprising esterase activity, thereby generating polymerized 3-HP.

41. A method for making a 3-HP ester, comprising:
isolating 3-HP generated using the method of claim 37; and
contacting the 3-HP with a peptide comprising lipase or esterase activity, thereby generating the 3-HP ester.

42. The method of claim 33, wherein the cell is a prokaryotic cell.

43. The isolated nucleic acid molecule of claim 1, wherein the nucleic acid sequence includes one or more substitutions which results in 1-5 conservative amino acid substitutions.

44. The isolated nucleic acid molecule of claim 1, wherein the nucleic acid sequence includes one or more substitutions which results in 1-10 conservative amino acid substitutions.

45. The isolated nucleic acid molecule of claim 1, wherein the nucleic acid sequence comprises at least 97% sequence identity to SEQ ID NO: 18.

46. The isolated nucleic acid molecule of claim 1, wherein the nucleic acid sequence comprises at least 98% sequence identity to SEQ ID NO: 18.

47. The isolated nucleic acid molecule of claim 1, wherein the nucleic acid sequence comprises at least 99% sequence identity to SEQ ID NO: 18.

48. The isolated nucleic acid molecule of claim 1, wherein the protein comprises a sequence having at least 97% sequence identity to SEQ ID NO: 19, and wherein the protein has BAAT activity.

49. The isolated nucleic acid molecule of claim 1, wherein the protein comprises a sequence having at least 98% sequence identity to SEQ ID NO: 19, and wherein the protein has BAAT activity.

50. The isolated nucleic acid molecule of claim 1, wherein the protein comprises a sequence having at least 99% sequence identity to SEQ ID NO: 19, and wherein the protein has BAAT activity.

51. The isolated nucleic acid molecule of claim 1, wherein the amino acid corresponding to position 133 of SEQ ID NO: 19 is Thr, and wherein the protein has BAAT activity.

52. The isolated nucleic acid molecule of claim 1, wherein the amino acid corresponding to position 3 of SEQ ID NO: 19 is His and wherein the protein has beta-alanine aminotransferase (BAAT) activity.

53. The isolated nucleic acid molecule of claim 1, wherein the amino acid corresponding to position 24 of SEQ ID NO: 19 is Thr and wherein the protein has beta-alanine aminotransferase (BAAT) activity.

54. The isolated nucleic acid molecule of claim 1, wherein the amino acid corresponding to position 110 of SEQ ID NO: 19 is Asn and wherein the protein has beta-alanine aminotransferase (BAAT) activity.

55. The isolated nucleic acid molecule of claim 1, wherein the amino acid corresponding to position 113 of SEQ ID NO: 19 is Leu, and wherein the protein has beta-alanine aminotransferase (BAAT) activity.

* * * * *

UNITED STATES PATENT AND TRADEMARK OFFICE
CERTIFICATE OF CORRECTION

| | | |
|---|---|---|
| PATENT NO. | : 8,030,045 B2 | Page 1 of 4 |
| APPLICATION NO. | : 12/310503 | |
| DATED | : October 4, 2011 | |
| INVENTOR(S) | : Jessen et al. | |

It is certified that error appears in the above-identified patent and that said Letters Patent is hereby corrected as shown below:

On the Title Page:

Item (56) References Cited, under Other Publications:

Second column, line 22, "specificty" should be --specificity--.

Second column, line 23, "Methytransferase" should be --Methyltransferase--.

Second column, line 26, "polymorhisms" should be --polymorphisms--.

Second column, line 40, "Q05881" should be --Q0S881--.

In the Specification:

Column 1, line 59, "aminotransferase" should be --aminotransferases--.

Column 2, line 18, "allow" should be --allowing--.

Column 2, line 67, "molecules" should be --molecule--.

Column 3, line 9, "result in" should be --that result in--.

Column 4, line 53, "shown" should be --shown in--.

Column 5, line 34, "atpFHgenes" should be --*atpFH* genes--.

Column 5, line 58, "dehydrogenase" should be --dehydrogenase activity--.

Column 6, line 15, "AAA2342" should be --AAA2342,--.

Column 6, line 21, "For example." should be --For example,--.

Column 6, line 22, the "." should be a --,--.

Column 6, line 49, ")." should be --),--.

Column 6, line 51, ")." should be --),--.

Column 6, line 52, ")." should be --),--.

Column 6, line 67, "blotting" should be --blotting.--.

Column 7, line 35, "L2001" should be --L200I--.

Signed and Sealed this
Twentieth Day of March, 2012

David J. Kappos
*Director of the United States Patent and Trademark Office*

Column 8, line 44, "He" should be --Ile--.

Column 8, line 46, "Tip" should be --Trp--.

Column 8, line 49, "locations in" should be --locations--.

Column 8, line 60, "or" should be --of--.

Column 9, line 12, "enhance," should be --enhance--.

Column 9, line 30, "herein" should be --herein,--.

Column 9, line 31, "cell" should be --cell,--.

Column 10, line 63, "18)." should be --18.--.

Column 10, line 66, "in M" should be --mM--.

Column 11, lines 55-56, "molecule" should be --molecules--.

Column 12, line 55, "peptide, side" should be --peptide side--.

Column 13, line 50, "in is" should be --is--.

Column 14, line 38, "1994," should be --1994.--.

Column 15, line 35, "Indentified" should be --Identified--.

Column 16, line 16 "multiple, nucleic" should be --multiple nucleic--.

Column 17, line 52, "example." should be --example,--.

Column 18, line 23, "retain" should be --retains--.

Column 18, line 26, the "." should be a --,--.

Column 19, line 49, "on" should be --one--.

Column 19, line 66, "enhances expresses" should be --enhances expression--.

Column 19, line 67, "a increase" should be --an increase--.

Column 20, line 9, "derivates" should be --derivatives--.

Column 20, line 52, "1152; can" should be --1152 can--.

Column 21, line 29, "example." should be --example,--.

Column 21, line 32, "Cold Spring, Harbor" should be --Cold Spring Harbor--.

Column 21, line 33, "Ch. 15," should be --Ch. 15.--.

Column 21, line 34, "usage, bias" should be --usage bias--.

Column 21, line 58, "identify" should be --identity--.

Column 22, line 16, "Thus." should be --Thus,--.

Column 22, line 53, "of" should be --or--.

Column 22, line 62, "a downstream" should be --downstream--.

Column 22, line 63, "derivates" should be --derivatives--.

Column 23, line 11, "carboxlase" should be --carboxylase--.

Column 24, line 12, "increased" should be --increase--.

CERTIFICATE OF CORRECTION (continued)
U.S. Pat. No. 8,030,045 B2

Column 24, line 31, "combination" should be --combinations--.

Column 24, line 48, "example." should be --example,--.

Column 24, line 52, "cell, in" should be --cell. In--.

Column 25, line 40, "expresses" should be --expressed--.

Column 25, line 54, "or and" should be --or--.

Column 26, line 38, "front" should be --from--.

Column 27, line 59, "1.3" should be --1,3--.

Column 29, line 26, "*Thermosynecliococcus*" should be --*Thermosynechococcus*--.

Column 30, line 26, "NC002516." should be --NC002516,--.

Column 30, line 28, "NP_252259." should be --NP_252259,--.

Column 33, line 13, "sequence, can" should be --sequence can--.

Column 33, line 26, "regulate, the" should be --regulate the--.

Column 33, line 41, "enzyme, is" should be --enzyme is--.

Column 34, line 8, "Harbour" should be --Harbor--.

Column 34, line 63, "~M" should be --$\mu$M--.

Column 35, line 41, "dCTP," should be --dCTP.--.

Column 36, line 33, "three, colonies" should be --three colonies--.

Column 36, line 63, "TD" should be --ID--.

Column 37, line 17, "scrapped" should be --scraped--.

Column 37, line 38, "30 C" should be --30°C--.

Column 38, line 32, the "." should be a --,--.

Column 38, line 49, "HCL" should be --HCl--.

Column 38, line 62, "protein" should be --protein.--.

Column 41, line 29, "pET28B" should be --pET28b--.

Column 42, line 2, the "." should be a --,--.

Column 42, line 31, "HCL" should be --HCl--.

Column 43, line 4, "pET28B" should be --pET28b--.

Column 43, line 58, "plnt" should be --pInt--.

Column 45, line 32, "HCL" should be --HCl--.

Column 47, line 2, "negative," should be --negative--.

Column 47, line 3, "following;" should be --following:--.

Column 47, line 6, "15.0:" should be --15.0;--.

Column 47, line 9, the "." should be a --,--.

Column 47, line 56, "al 30°C" should be --at 30°C--.

CERTIFICATE OF CORRECTION (continued)
U.S. Pat. No. 8,030,045 B2

Column 48, line 48, "these, observations" should be --these observations--.

Column 48, line 61, "in when" should be --when--.

Column 49, line 59, "4.000" should be --4,000--.

Column 50, lines 12-13, "a increase," should be --an increase--.

Column 50, line 67, "Ppmmsb31" should be --PpmmsB31--.

Column 51, line 17, "hours." should be --hours,--.

Column 51, in Table 5, "Ppmmsb31" should be --PpmmsB31--.

Column 52, line 12, "trains" should be --strains--.

Column 52, line 17, "Ppmmsb31" should be --PpmmsB31--.

Column 53, line 9, "of the of" should be --of the--.

Column 53, line 61, "hours." should be --hours,--.

Column 54, in Table 6, "Ppmmsb31" should be --PpmmsB31--.

Column 54, line 45, "How" should be --flow--.

Column 55, line 31, "0.1" should be --1--.

Column 55, line 36, "pH 8.1%" should be --pH 8, 1%--.

Column 57, line 3, "exogeous" should be --exogenous--.

Column 58, line 63, "vitro" should be --*in vitro*--.

Column 59, line 33, "include" should be --includes--.

Column 60, line 15, "1))." should be --1).--.

Column 60, line 20, "include" should be --includes--.

Column 60, line 29, "includes" should be --include--.

Column 61, line 9, "encode" should be --encodes--.

Column 61, line 13, "include" should be --includes--.

Column 61, line 22, "includes" should be --include--.

In the Claims:

Column 119, line 8, claim 29, "results an" should be --results in an--.

Column 119, line 13, claim 30, "results an" should be --results in an--.